(12) United States Patent
Dervan et al.

(10) Patent No.: US 7,935,530 B2
(45) Date of Patent: May 3, 2011

(54) POLYAMIDES WITH TAIL STRUCTURES CAPABLE OF BINDING DNA

(75) Inventors: Peter B. Dervan, San Marino, CA (US); Claire S. Jacobs, San Marino, CA (US); Nicholas G. Nickols, Van Nuys, CA (US); Daniel A. Harki, Pasadena, CA (US)

(73) Assignee: California Institute of Technology, Pasedena, CA (US)

( * ) Notice: Subject to any disclaimer, the term of this patent is extended or adjusted under 35 U.S.C. 154(b) by 107 days.

(21) Appl. No.: 11/998,446

(22) Filed: Nov. 28, 2007

(65) Prior Publication Data

US 2008/0269138 A1    Oct. 30, 2008

Related U.S. Application Data

(60) Provisional application No. 60/861,756, filed on Nov. 29, 2006.

(51) Int. Cl.
*C12N 15/00* (2006.01)
*A61K 38/04* (2006.01)

(52) U.S. Cl. .......................... 435/440; 530/328
(58) Field of Classification Search .................. None
See application file for complete search history.

(56) References Cited

U.S. PATENT DOCUMENTS

| | | | |
|---|---|---|---|
| 5,998,140 A | 12/1999 | Dervan | |
| 6,090,947 A | 7/2000 | Dervan | |
| 6,143,901 A | 11/2000 | Dervan | |
| 6,303,312 B1 | 10/2001 | Dervan | |
| 6,472,537 B1 | 10/2002 | Baird | |
| 6,506,906 B1 * | 1/2003 | Dervan | 548/312.4 |
| 6,545,162 B1 | 4/2003 | Dervan | |
| 6,555,692 B1 | 4/2003 | Dervan | |
| 6,559,125 B1 | 5/2003 | Dervan | |
| 6,635,417 B1 | 10/2003 | Dervan | |
| 6,660,255 B1 | 12/2003 | Gottesfeld | |
| 6,673,940 B1 | 1/2004 | Dervan | |
| 6,958,240 B1 | 10/2005 | Baird | |
| 7,049,061 B1 | 5/2006 | Baird | |
| 7,087,378 B1 | 8/2006 | Baird | |
| 7,452,730 B2 | 11/2008 | Dervan | |
| 2003/0109448 A1 | 6/2003 | Crowley | |
| 2005/0026174 A1 | 2/2005 | Dervan | |

(Continued)

FOREIGN PATENT DOCUMENTS

WO    WO 97/30975    8/1997

(Continued)

OTHER PUBLICATIONS

Foister et al., Shape Selective Recognition of T.A Base Pairs by Hairpin Polyamides Containing N-Terminal 3-Methoxy (and 3-Chloro) Thiophene Residues, Bioorganic & Medicinal Chemistry 11 (2003) 4333-4340.*

(Continued)

*Primary Examiner* — Mark Staples
(74) *Attorney, Agent, or Firm* — Stahl Law Firm

(57) ABSTRACT

The present invention relates to polyamides with a tail comprising a linker and an end-group. A preferred end-group is isophthalic acid and derivatives thereof. Polyamides of the invention are capable of entering the nucleus of cells. Polyamides of the invention are capable of selectively binding DNA. The invention also relates to methods of using the polyamides in therapy and research.

20 Claims, 35 Drawing Sheets

U.S. PATENT DOCUMENTS

Figure 1:
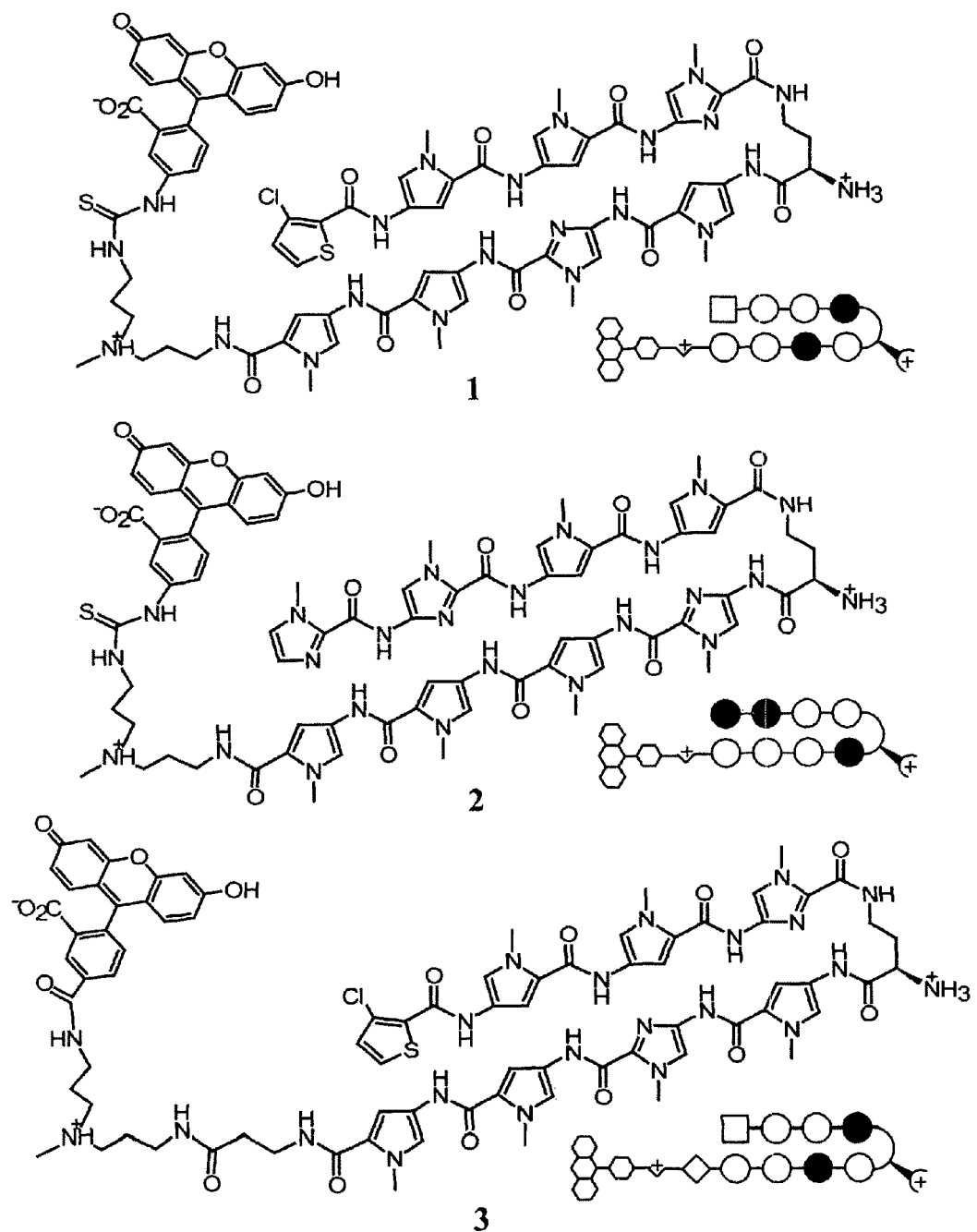

| | | |
|---|---|---|
| 2006/0014163 A1 | 1/2006 | Dervan |
| 2006/0019972 A1 | 1/2006 | Dervan |
| 2006/0025429 A1 | 2/2006 | Dervan |
| 2006/0270727 A1 | 11/2006 | Melander |

FOREIGN PATENT DOCUMENTS

| | | |
|---|---|---|
| WO | WO 98/35702 | 8/1998 |
| WO | WO 98/37066 | 8/1998 |
| WO | WO 98/45284 | 10/1998 |
| WO | WO 98/49142 | 11/1998 |
| WO | WO 98/50058 | 11/1998 |
| WO | WO 98/37087 | 8/1999 |
| WO | WO 03/041128 | 5/2003 |

OTHER PUBLICATIONS

Anjana et al., Activation Specificity of Arsonate-Reactive T-Cell Clones, J. ExP. Med. © The Rockefeller University Press • 0022-1007/84/02/0479/16, vol. 159 Feb. 1984 479-494.*

Almarsson et al., 1993, "Molecular mechanics calculations of the structures of polyamide nucleic acid DNA duplexes and triple helical hybrids," Proc. Natl. Acad. Sci. USA 90:7518-7522.

Baird et al., 1996, "Solid Phase Synthesis of Polyamides Containing Imidazole and Pyrrole Amino Acids," J. Am. Chem. Soc. 118:6141-6146.

Best et al., 2003, "Nuclear localization of pyrrole-imidazole polyamide-fluorescein conjugates in cell culture," Proc. Natl. Acad. Sci. USA 100(21):12063-12068.

Burnett et al., 2006, "DNA sequence-specific polyamides alleviate transcription inhibition associated with long GAA•TTC repeats in Friedrich's ataxia," Proc. Natl. Acad. Sci. USA 103(31):11497-11502.

Cherny et al., 1993, "DNA unwinding upon strand-displacement binding of a thymine-substituted polyamide to double-stranded DNA," Proc. Natl. Acad. Sci. USA 90:1667-1670.

Chiang et al., 2000, "Targeting the Ets Binding Site of the HER2/neu Promoter with Pyrrole-Imidazole Polyamides," J. Biol. Chem. 275(32):24246-24254.

Coull et al., 2002, "Targeted Derepression of the Human Immunodeficiency Virus Type 1 Long Terminal Repeat by Pyrrole-Imidazole Polyamides," J. Virology 76(23):12349- 12354.

Dervan, 2001, "Molecular Recognition of DNA by Small Molecules," Bioorganic & Medicinal Chem. 9:2215-2235.

Dickinson et al., 1998, "Inhibition of RNA polymerase II transcription in human cells by synthetic DNA-binding ligands," Proc. Natl. Acad. Sci. USA 95:12890-12895.

Dickinson et al., 2004, "Arresting Cancer Proliferation by Small-Molecule Gene Regulation," Chemistry & Biology 11: 1583-1594.

Dudouet et al., 2003, "Accessibility of Nuclear Chromatin by DNA Binding Polyamides," Chemistry & Biology 10:859-867.

Edelson et al., 2004, "Influence of structural variation on nuclear localization of DNA-binding polyamde-fluorophore conjugates," Nucleic Acids Res. 32(9):2802-2818.

Ehley et al., 2002, "Promoter Scanning for Transcription Inhibition with DNA-Binding Polyamides," Molecular and Cellular Biology 22(6):1723-1733.

Gottesfeld et al., 2001, "Sequence-specific Recognition of DNA in the Nucleosome by Pyrrole-Imidazole Polyamides," J. Mol. Biol. 309:615-629.

Gygi et al., 2002, "Use of fluorescent sequence-specific polyamides to discriminate human chromosomes by microscopy and flow cytometry," Nucleic Acids Res. 30(13):2790-2799.

Hsu et al., 2007, "Completion of a Programmable DNA-Binding Small Molecule Library," Tetrahedron 63(27):6146-6151.

Hurley, 2002, "DNA and its associated processes as targets for cancer therapy," Nature Reviews 2:188-200.

Kelly et al., 1996, "Binding site size limit of the 2:1 pyrrole-imidazole polyamide-DNA motif," Proc. Natl. Acad. Sci. USA 93:6981-6985.

Lacy et al., 2002, "Recognition of T•G mismatched base pairs in DNA by stacked imidazole-containing polyamides: surface plasmon resonance and circular dichroism studies," Nucleic Acids Res. 30(8):1834-1841.

Lacy et al., 2004, "Energetic basis for selective recognition of T•G mismatched base pairs in DNA by imidazole-rich polyamides," Nucleic Acids Res. 32(6):2000-2007.

Marques et al., 2002, "Toward an Understanding of the Chemical Etiology for DNA Minor-Groove Recognition by Polyamides," Helvetica Chimica Acta 85:4485-4517.

Melander et al., 2004, "Regulation of gene expression with pyrrole-imidazole polyamides," J. Biotechnology 112:195-220.

Neamati et al., 1998, "Highly Potent Synthetic Polyamides, Bisdistamycins, and Lexitropsins as Inhibitors of Human Immunodeficiency Virus Type 1 Integrase," Molecular Pharmacology 54:280-290.

Nickols et al., 2006, "Improved nuclear localization of DNA-binding polyamides," Nucleic Acids Res. 35(2):363-370.

Nickols et al., 2007, "Modulating Hypoxia-Inducible Transcription by Disrupting the HF-1DNA Interface," ACS Chemical Biology 2(8):561-571.

Nickols et al., 2007, "Suppression of androgen receptor-mediated gene expression by a sequence-specific DNA-binding polyamide," Proc. Natl. Acad. Sci. USA 104(25):10418-10423.

O'Hare et al., "DNA sequence recognition in the minor groove by crosslinked polyamides: The effect of N-terminal head group and linker length on binding affinity and specificity," Proc. Natl. Acad. Sci. USA 99(1):72-77.

Olenyuk et al., 2004, "Inhibition of vascular endothelial growth factor with a sequence-specific hypoxia response element antagonist," Proc. Natl. Acad. Sci. USA 101(48):16768-16773.

Philips et al., 2005, "DNA Damage Effects of a Polyamide-CBI Conjugate in SV40 Virions," Mol. Pharmacol. 67:877-882.

Pilch et al., 1996, "Binding of a hairpin polyamide in the minor groove of DNA: Sequence-specific enthalpic discrimination," Proc. Natl. Acad. Sci. USA 93:8306-8311.

Sazani et al., 2001, "Nuclear antisense effects of neutral, anionic and cationic oligonucleotide analogs," Nucleic Acids Res. 29(19):3965-3974.

Schaal et al., 2003, "Inhibition of human papilloma virus E2 DNA binding protein by covalently linked polyamides," Nucleic Acids Res. 31(4):1282-1291.

Trauger et al., 1996, "Extension of Sequence-Specific Recognition in the Minor Groove of DNA by Pyrrole-Imidazole Polyamides to 9-13 Base Pairs," J. Am. Chem. Soc. 118:6160-6166.

Tsai et al., 2006, "Unanticipated differences between α- and 65-diaminobutyric acid-linked hairpin polyamide-alkylator conjugates," Nucleic Acids Res. 35(1):307-316.

Urbach et al., 2001, "Toward rules for 1:1 polyamide:DNA recognition," Proc. Natl. Acad. Sci. USA 98(8):4343-4348.

Urbach et al., 2002, "Structure of a 62 -Alanine-linked Polyamide Bound to a Full Helical Turn of Purine Tract DNA in the 1:1 Motif," J. Mol. Biol. 320:55-71.

Wang et al., 2003, "DNA crosslinking and biological activity of a hairpin polyamide-chlorambucil conjugate," Nucleic Acids Res. 31(4):1208-1215.

Warren et al., 2006, "Defining the sequence-recognition profile of DNA-binding molecules," Proc. Natl. Acad. Sci. USA 103(4):867-872.

White et al., 1996, "Effects of the A•T/T•A Degeneracy of Pyrrole-Imidazole Polyamide Recognition in the Minor Groove of DNA," Biochemistry 35:12532-12537.

Wurtz et al., 2002, "Inhibition of DNA Binding by NF-κB with Pyrrole-Imidazole Polyamides," Biochemistry 41:7604-7609.

Smith, 1996, "Nucleic Acid Models," Prog. Polym. Sci., 21:209-253.

Suckling, 2004, "Minor groove binders 1998-2004," Expert Opinion Ther. Patents 14(12):1693-1724.

* cited by examiner

A 4-15

16-27

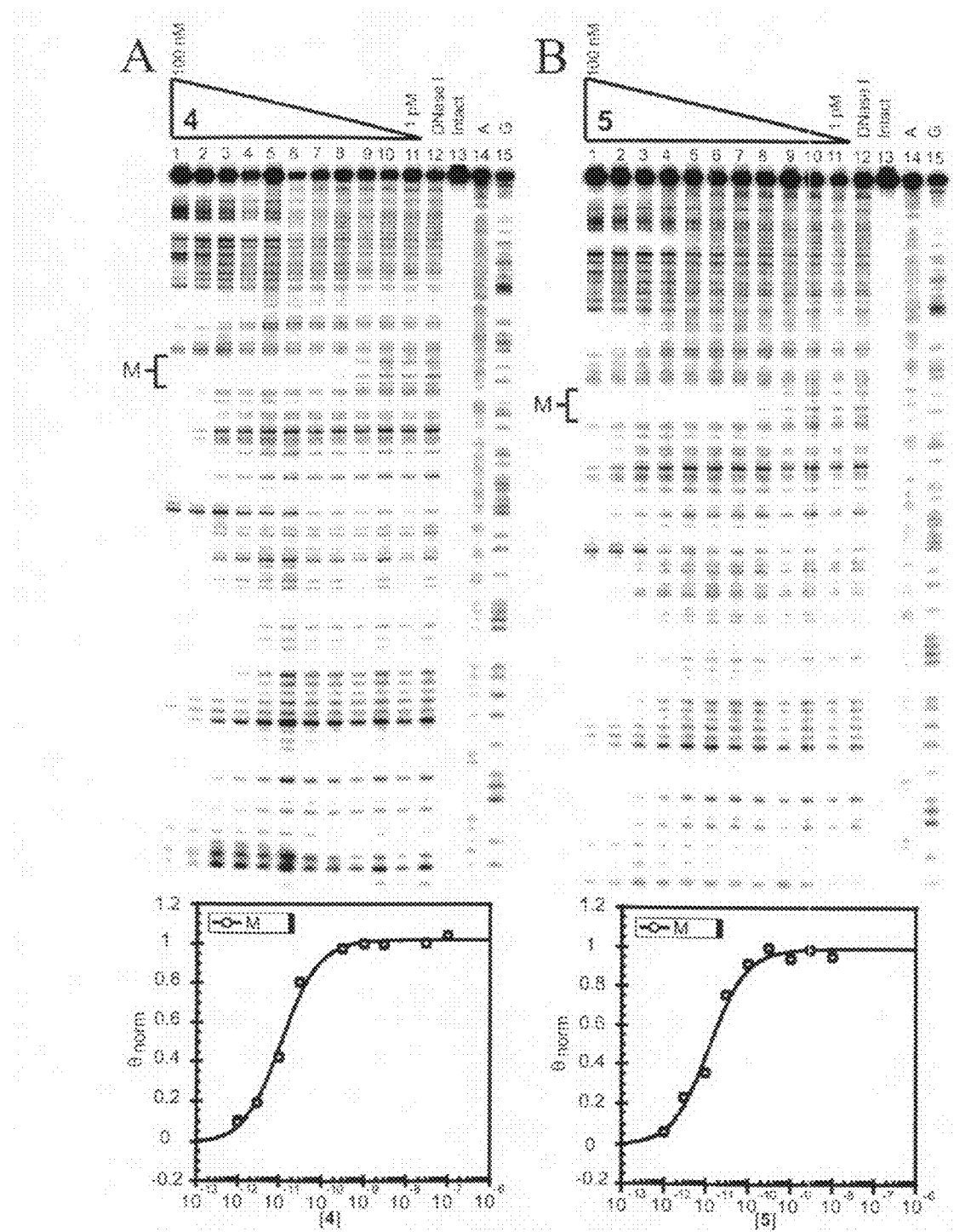
Figure 8A-B

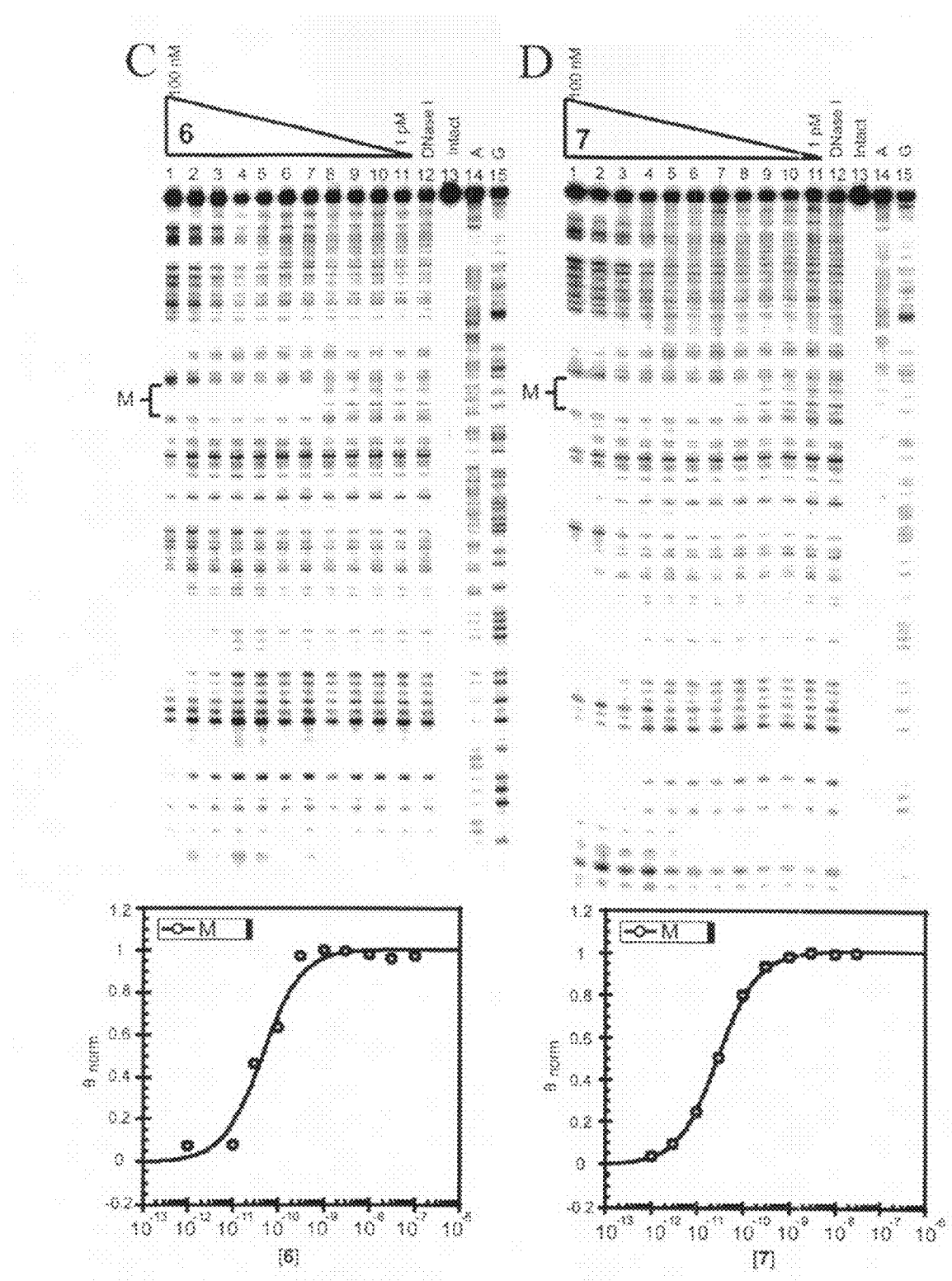
Figure 8C-D

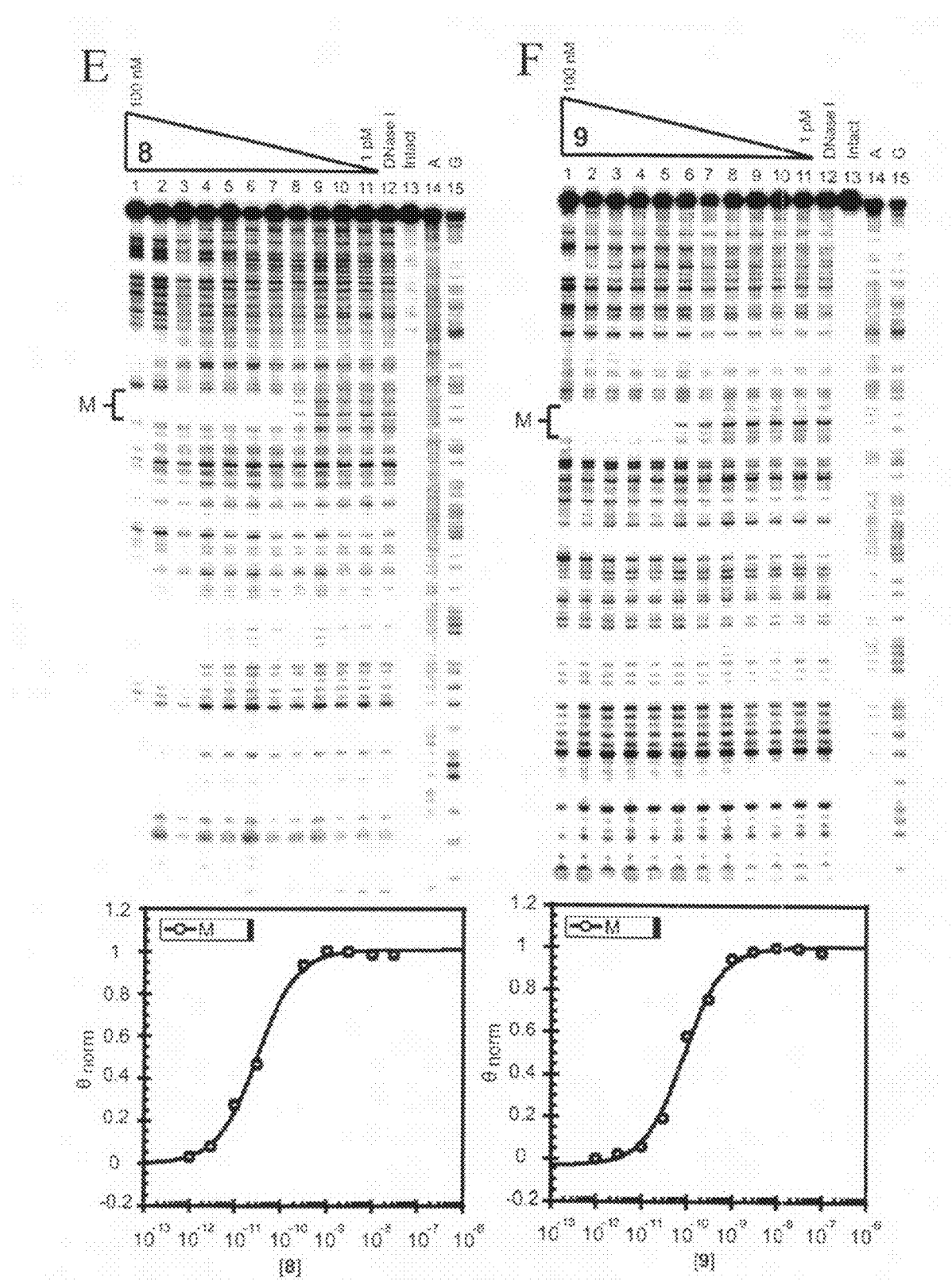
Figure 8E-F

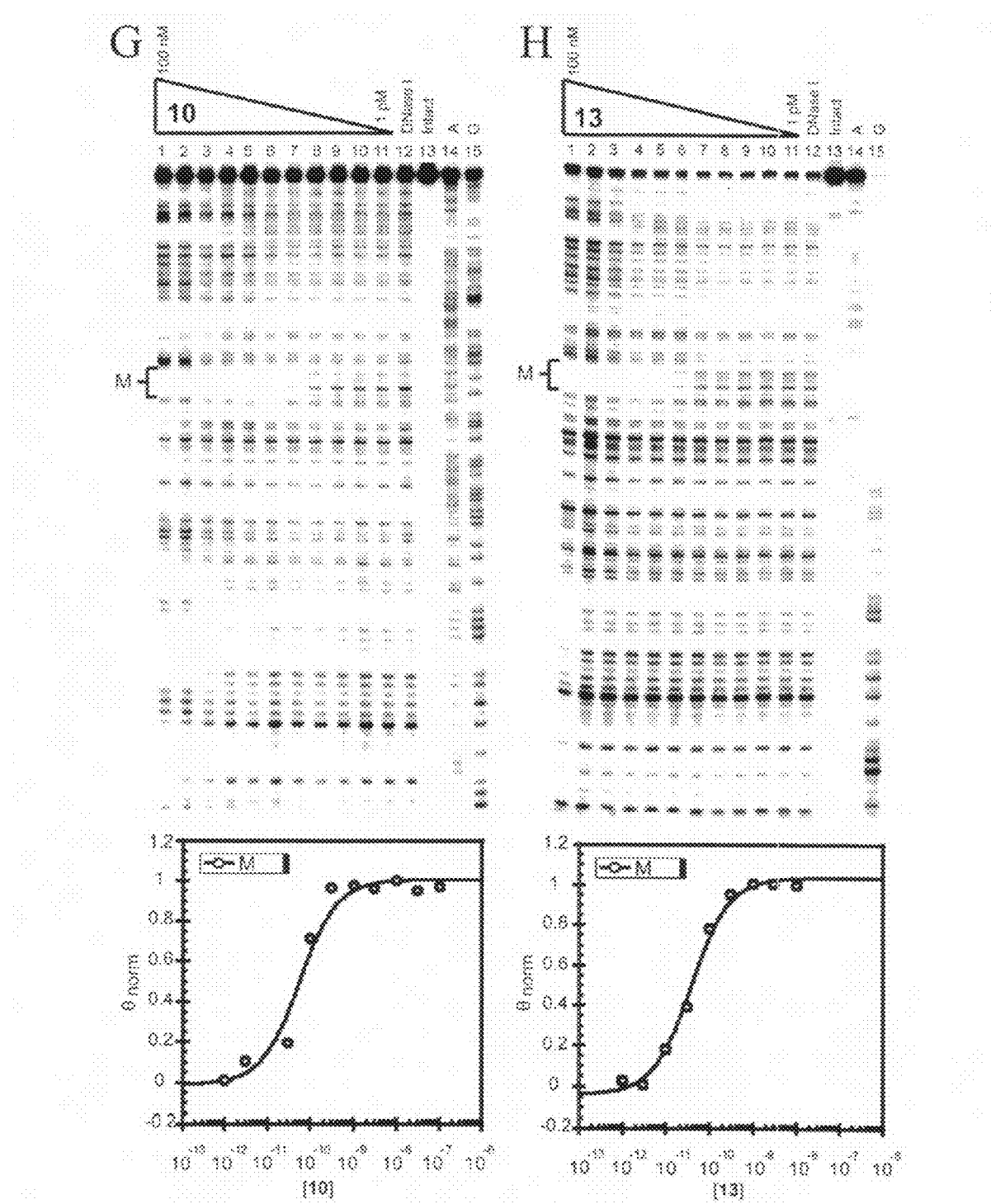
Figure 8G-H

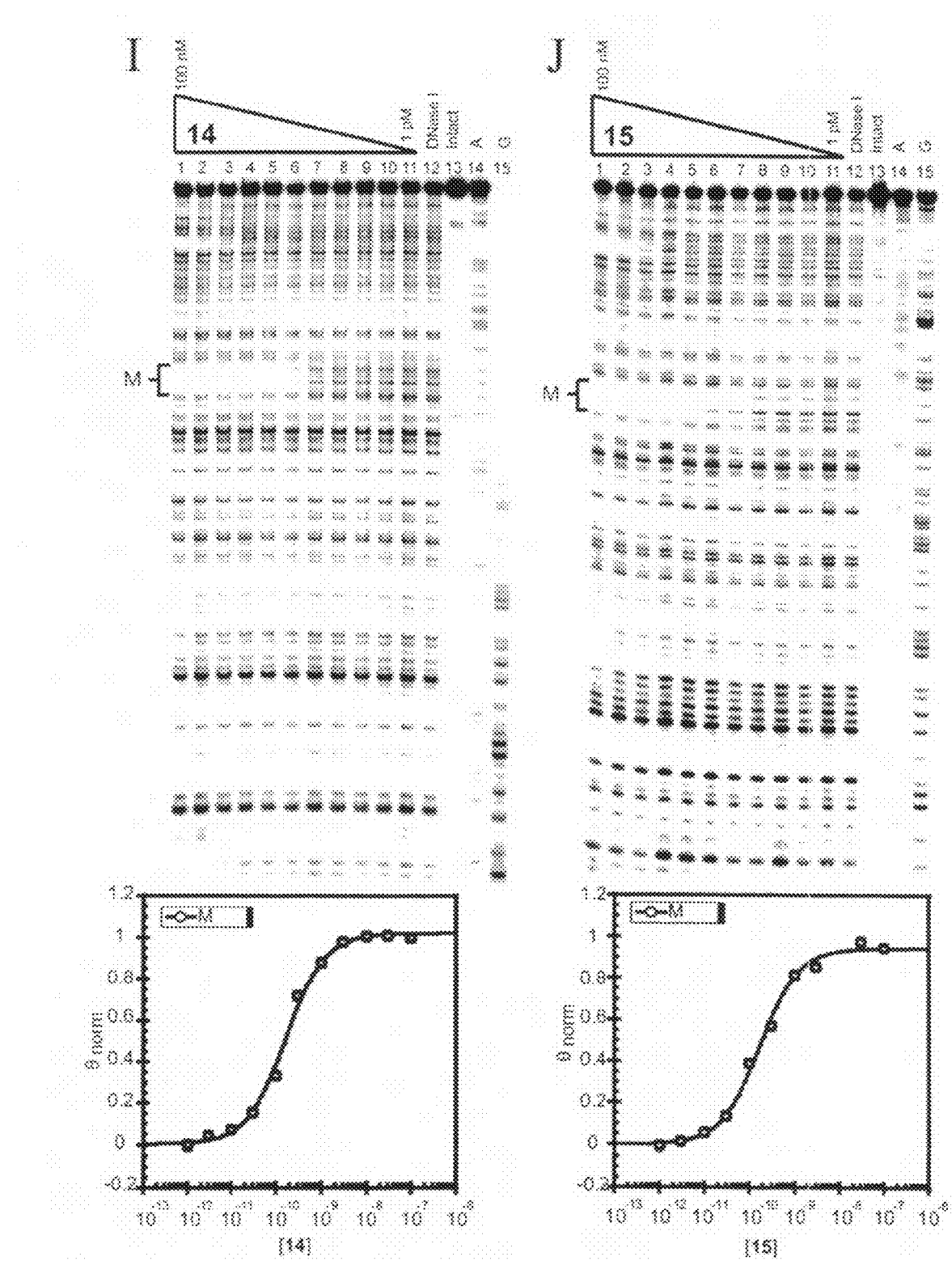
Figure 8I-J

A.

B.   R =
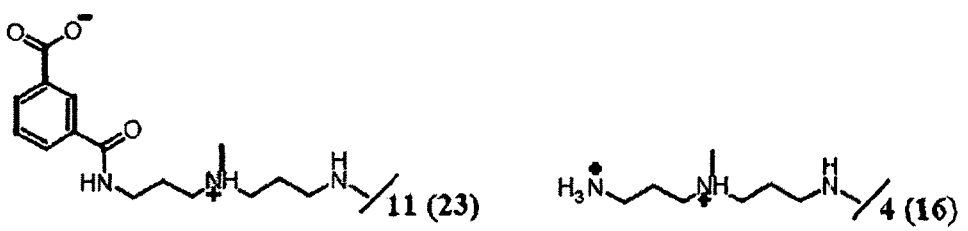
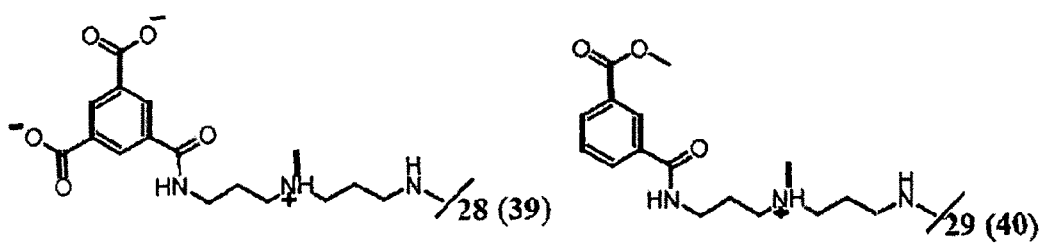
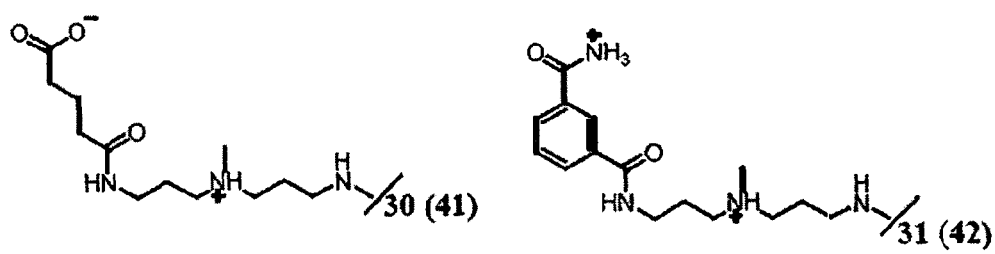
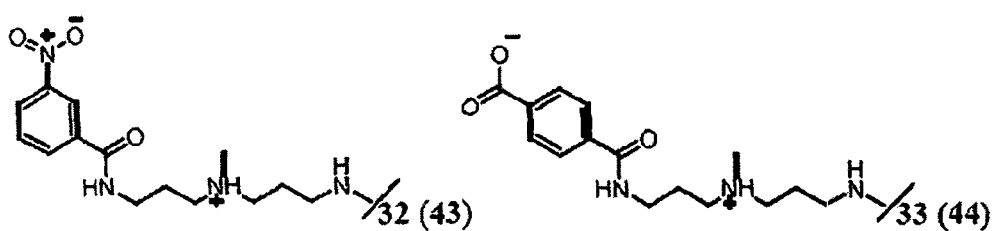
Figure 11B

C. R =
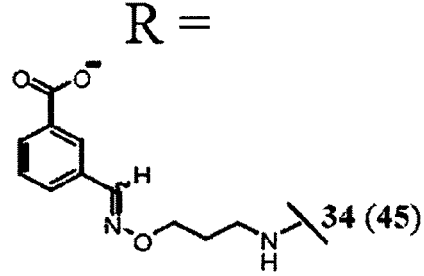
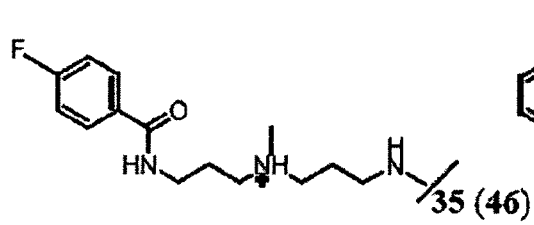 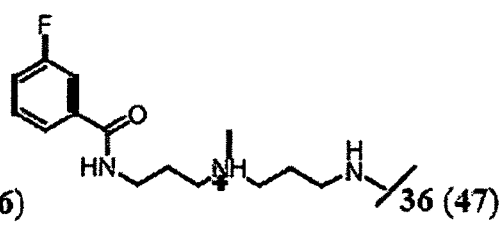
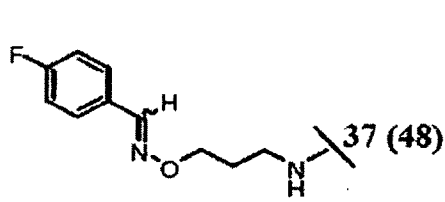 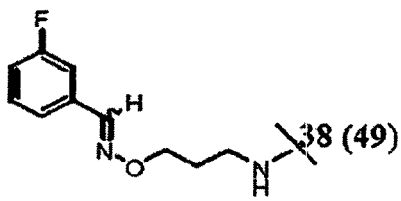
Figure 11C

Figure 13B:
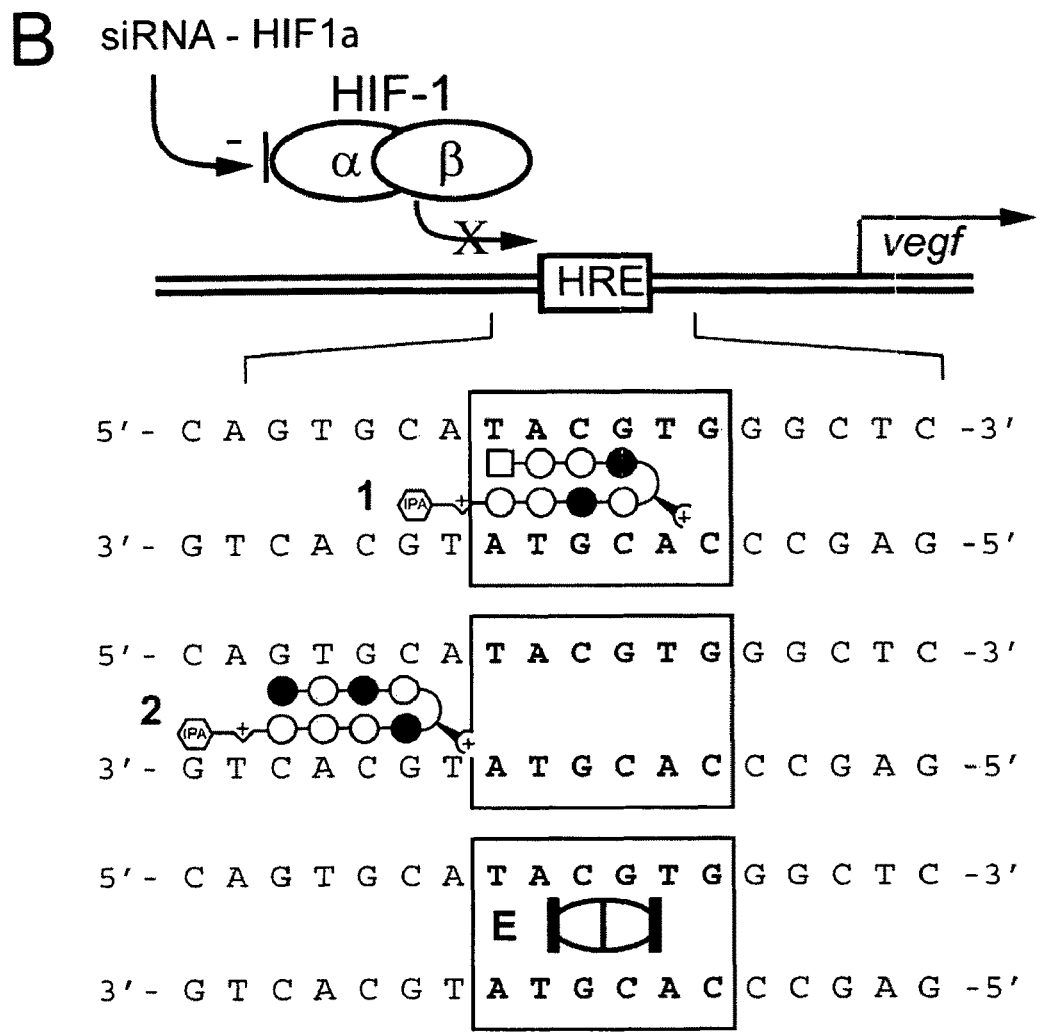

A
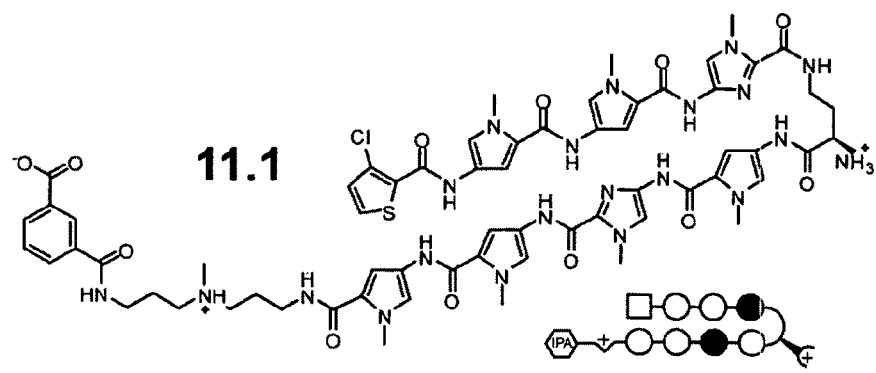
11.1
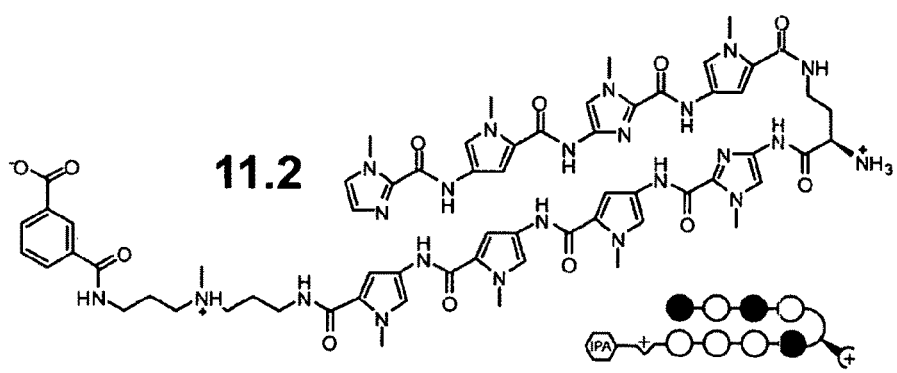
11.2
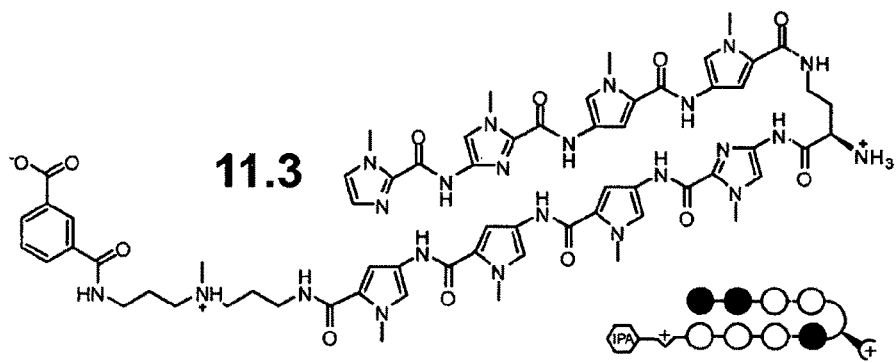
11.3
Echinomycin (E)
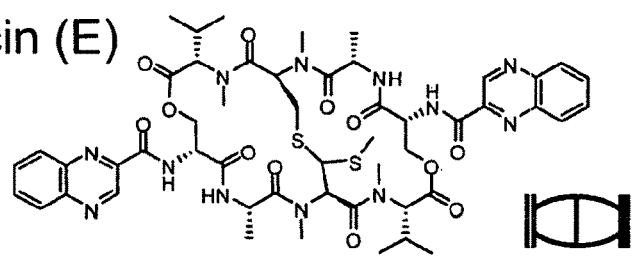
Figure 13A

Fold Change

| | | Treatment | – | R | E | 1 |
|---|---|---|---|---|---|---|
| | | DFO | – | + | + | + |
| ANGPT1 | | | -2.02 | -2.24 | -1.35 | -3.26 |
| CA12 | | | -5.62 | -4.09 | -6.48 | -5.44 |
| SERPINE1 | | | -2.72 | -9.68 | -2.41 | -7.4 |
| IGFBP3 | | | -46.12 | -26.11 | -100 | -7.13 |
| CA9 | | | -4.08 | -12.03 | -7.58 | -2.23 |
| VEGF | | | -2.94 | -5.61 | -34.16 | -1.83 |
| HIG2 | | | -14.83 | -12.1 | -100 | -2.44 |
| FLT1 | | | -2.81 | -5.13 | -3.79 | -1.45 |
| CP | | | -1.91 | -3.89 | -4.33 | -2.11 |
| EDN2 | | | -4.32 | -7.52 | -5.51 | -5.88 |
| TFR2 | | | -3.4 | -3.24 | -2.07 | -1.86 |
| TGFA | | | -10.22 | -11.03 | -23.46 | -4.46 |
| EDN1 | | | -2.23 | -2.1 | -10.41 | -2.23 |
| AK3 | | | -3.94 | -14.26 | -5.03 | -1.12 |
| BNIP3L | | | -3.27 | -8.54 | -4.03 | -1.04 |
| ADM | | | -3.57 | -3.80 | -13.61 | -1.10 |
| NDRG1 | | | -5.8 | -8.8 | -10.8 | -1.23 |
| E2IG5 | | | -3.21 | -5.36 | -5.41 | -1.18 |
| LOX | | | -19.36 | -10.79 | -19.41 | -1.62 |
| TGFB3 | | | -1.62 | -1.59 | -1.73 | -1.11 |
| PFKFB3 | | | -2.49 | -4.6 | -25.18 | 1.09 |
| PFKFB4 | | | -8.26 | -13.29 | -86.46 | 1.21 |
| BNIP3 | | | -2.34 | -4.92 | -7.15 | 1.1 |
| HK1 | | | -1.90 | -1.96 | -2.84 | -1.15 |
| LDHA | | | -1.81 | -1.85 | -16.18 | -1.06 |
| EGLN1 | | | -3.75 | -4.47 | -27.34 | 1.03 |
| EGLN3 | | | -4.05 | -6.97 | -73.59 | -1.08 |
| PGK1 | | | -1.7 | -3.21 | -2.15 | -1.12 |
| CDKN1A | | | -3.99 | -2.03 | -88.94 | 1.56 |
| TFRC | | | -1.88 | -1.40 | -1.50 | 1.08 |
| HMOX1 | | | -1.75 | -1.10 | -11.93 | 1.51 |

Figure 16C

SEQUENCE LISTING

```
<160> NUMBER OF SEQ ID NOS: 33

<210> SEQ ID NO 1
<211> LENGTH: 18
<212> TYPE: DNA
<213> ORGANISM: Human

<400> SEQUENCE: 1
cagtgcatac gtgggctc                                                  18

<210> SEQ ID NO 2
<211> LENGTH: 36
<212> TYPE: DNA
<213> ORGANISM: Human

<400> SEQUENCE: 2
agactccaca gtgcatacgt gggctccaac aggtcc                              36

<210> SEQ ID NO 3
<211> LENGTH: 36
<212> TYPE: DNA
<213> ORGANISM: Human

<400> SEQUENCE: 3
acataattga ggaacaacgt ggaattagtg tcatag                              36

<210> SEQ ID NO 4
<211> LENGTH: 20
<212> TYPE: DNA
<213> ORGANISM: Human

<400> SEQUENCE: 4
agggcagaat catcacgaag                                                20

<210> SEQ ID NO 5
<211> LENGTH: 21
<212> TYPE: DNA
<213> ORGANISM: Human

<400> SEQUENCE: 5
gggtactcct ggaagatgtc c                                              21

<210> SEQ ID NO 6
<211> LENGTH: 22
<212> TYPE: DNA
<213> ORGANISM: Human

<400> SEQUENCE: 6
ctcatttgga attttgccga tt                                             22

<210> SEQ ID NO 7
<211> LENGTH: 22
<212> TYPE: DNA
<213> ORGANISM: Human

<400> SEQUENCE: 7
ccgagtgaag atcccctttt ta                                             22
```

```
<210> SEQ ID NO 8
<211> LENGTH: 14
<212> TYPE: DNA
<213> ORGANISM: Human

<400> SEQUENCE: 8
agcgtacgtg cctc                                                         14

<210> SEQ ID NO 9
<211> LENGTH: 14
<212> TYPE: DNA
<213> ORGANISM: Human

<400> SEQUENCE: 9
gcgggacgtg acgc                                                         14

<210> SEQ ID NO 10
<211> LENGTH: 14
<212> TYPE: DNA
<213> ORGANISM: Human

<400> SEQUENCE: 10
gacgcacgtg ggca                                                         14

<210> SEQ ID NO 11
<211> LENGTH: 14
<212> TYPE: DNA
<213> ORGANISM: Human

<400> SEQUENCE: 11
ggcggacgtg cggg                                                         14

<210> SEQ ID NO 12
<211> LENGTH: 14
<212> TYPE: DNA
<213> ORGANISM: Human

<400> SEQUENCE: 12
ctcacacgtg ggtt                                                         14

<210> SEQ ID NO 13
<211> LENGTH: 14
<212> TYPE: DNA
<213> ORGANISM: Human

<400> SEQUENCE: 13
gccgcacgtg ccac                                                         14

<210> SEQ ID NO 14
<211> LENGTH: 14
<212> TYPE: DNA
<213> ORGANISM: Human

<400> SEQUENCE: 14
gggctacgtg caga                                                         14

<210> SEQ ID NO 15
<211> LENGTH: 14
<212> TYPE: DNA
<213> ORGANISM: Human

<400> SEQUENCE: 15
ggtgtacgtg caga                                                         14
```

<210> SEQ ID NO 16
<211> LENGTH: 14
<212> TYPE: DNA
<213> ORGANISM: Human

<400> SEQUENCE: 16
gtgagacgtg cggc                                                         14

<210> SEQ ID NO 17
<211> LENGTH: 14
<212> TYPE: DNA
<213> ORGANISM: Human

<400> SEQUENCE: 17
tgccgacgtg cgct                                                         14

<210> SEQ ID NO 18
<211> LENGTH: 14
<212> TYPE: DNA
<213> ORGANISM: Human

<400> SEQUENCE: 18
gctgtacgtg catt                                                         14

<210> SEQ ID NO 19
<211> LENGTH: 14
<212> TYPE: DNA
<213> ORGANISM: Human

<400> SEQUENCE: 19
tgcatacgtg ggct                                                         14

<210> SEQ ID NO 20
<211> LENGTH: 14
<212> TYPE: DNA
<213> ORGANISM: Human

<400> SEQUENCE: 20
gaacaacgtg gaat                                                         14

<210> SEQ ID NO 21
<211> LENGTH: 14
<212> TYPE: DNA
<213> ORGANISM: Human

<400> SEQUENCE: 21
aggcaacgtg cagc                                                         14

<210> SEQ ID NO 22
<211> LENGTH: 20
<212> TYPE: DNA
<213> ORGANISM: Human

<400> SEQUENCE: 22
agggcagaat catcacgaag                                                   20

<210> SEQ ID NO 23
<211> LENGTH: 21
<212> TYPE: DNA
<213> ORGANISM: Human

<400> SEQUENCE: 23
gggtactcct ggaagatgtc c                                                 21

```
<210> SEQ ID NO 24
<211> LENGTH: 22
<212> TYPE: DNA
<213> ORGANISM: Human

<400> SEQUENCE: 24
ctcatttgga attttgccga tt                                              22

<210> SEQ ID NO 25
<211> LENGTH: 22
<212> TYPE: DNA
<213> ORGANISM: Human

<400> SEQUENCE: 25
ccgagtgaag atcccctttt ta                                              22

<210> SEQ ID NO 26
<211> LENGTH: 21
<212> TYPE: DNA
<213> ORGANISM: Human

<400> SEQUENCE: 26
cagcaacatg ggaaacagaa t                                               21

<210> SEQ ID NO 27
<211> LENGTH: 21
<212> TYPE: DNA
<213> ORGANISM: Human

<400> SEQUENCE: 27
tagagtcagc cacaaccaag g                                               21

<210> SEQ ID NO 28
<211> LENGTH: 18
<212> TYPE: DNA
<213> ORGANISM: Human

<400> SEQUENCE: 28
cctttgggtt ttgccaga                                                   18

<210> SEQ ID NO 29
<211> LENGTH: 18
<212> TYPE: DNA
<213> ORGANISM: Human

<400> SEQUENCE: 29
ccaagtttgt ggagctga                                                   18

<210> SEQ ID NO 30
<211> LENGTH: 19
<212> TYPE: DNA
<213> ORGANISM: Human

<400> SEQUENCE: 30
aaaagggcgc tctgtgagt                                                  19

<210> SEQ ID NO 31
<211> LENGTH: 18
<212> TYPE: DNA
<213> ORGANISM: Human

<400> SEQUENCE: 31
gctgactgtg gggtgtcc                                                   18
```

```
<210> SEQ ID NO 32
<211> LENGTH: 19
<212> TYPE: DNA
<213> ORGANISM: Human

<400> SEQUENCE: 32
cccctaagtc gggaaggtt                                              19

<210> SEQ ID NO 33
<211> LENGTH: 20
<212> TYPE: DNA
<213> ORGANISM: Human

<400> SEQUENCE: 33
gtccgtctgc gagggtacta                                             20
```

POLYAMIDES WITH TAIL STRUCTURES CAPABLE OF BINDING DNA

This application claims the benefit of U.S. Provisional Application No. 60/861,756, filed Nov. 29, 2006, which is incorporated herein by reference in its entirety.

The U.S. Government has certain rights in this invention pursuant to Grant No. GM051747 awarded by the National Institutes of Health.

1.0 FIELD OF THE INVENTION

The present invention relates to polyamides with tail structures. Polyamides of the invention are capable of entering a cell and the nucleus of the cell to bind DNA. Polyamides of the invention can be used in therapy, diagnostics and as research tools.

2.0 BACKGROUND

Gene regulation plays key roles in many aspects of disease and development. The human genome project and other sequencing efforts have provided much information on the identity of genes. Functional studies have examined how genes affect physiological and pathological processes. Living organisms use various mechanisms to regulate gene expression and thereby affect the onset and progression of many diseases as well as multiple processes observed under non-disease conditions. The ability to modulate gene expression would provide a means of adjusting physiological processes in disease and non-disease conditions, especially where the modulation of gene expression can be aimed at select genes of interest. Of particular interest are compounds capable of modulating gene expression in cultured cells, in animals, in plants, and/or in humans.

Among compounds capable of modulating gene expression are polyamides, which have been used for that purpose in cells and animals. Polyamides have been shown to bind DNA at specific sequences, thus allowing them to modulate a gene linked to those sequences while not or not significantly interfering with the expression of other genes. Moreover, polyamides can be designed to recognize a DNA sequence of interest, thus allowing drug design aimed at modulating the expression of genes involved in a disease or phenotype of interest. While the sequence-specific DNA binding ability of polyamides has been recognized, it has been difficult to facilitate delivery of polyamides to their target sequence, while maintaining their DNA binding abilities. Target delivery of polyamides is believed to involve uptake of the polyamides into cells and their nuclei, and it is further aided by their ability to sufficiently remain in the nuclei to allow binding of the polyamides to their target sequence.

The entry of molecules into cells and their nuclei is generally believed to inversely correlate with the size of the molecules. Polyamides are large and complex molecules when compared to typical molecules known to enter cells and their nuclei with ease. Polyamides were therefore traditionally designed to minimize their size to facilitate entry into cells and their nuclei. Polyamides that were limited to structures needed for DNA binding, however, were found to have limited abilities to enter cells and especially their nuclei. Polyamides linked to the large fluorophore fluorescein, by contrast, were found to have significantly enhanced capabilities to enter cells and nuclei. This finding seemed surprising given that the fluorescein molecule carries two negative charges under physiological conditions and includes four six-rings, thus considerably increasing the size of the polyamide.

The addition of fluorescein to polyamides, however, has certain disadvantages. For example, the fluorescein moiety is not considered necessary for DNA binding but rather was found to lessen the affinity of polyamides for their target DNA. Also, the conversion of polyamides to polyamide-fluorescein conjugates requires additional synthesis steps and thus increases the cost of polyamides and their use.

Thus, new polyamide derivates are needed that have a high DNA binding affinity and that are capable of entering cells and their nuclei. The current invention provides such polyamides.

3.0 SUMMARY OF THE INVENTION

The present invention relates to polyamides with a tail structure (tail-polyamides) and their use. A tail-polyamide of the invention has a tail structure comprising a linker and an end-group. An end-group of a tail-polyamide of the invention, in certain embodiments, has a structural element that resembles a part or parts of fluorescein. An end-group in certain embodiments is isophthalic acid; phthalic acid; terephthalic acid; benzamide; morpholine; N,N-dimethylbenzamide; N,N-bis(trifluoromethyl)benzamide; fluorobenzene; (trifluoromethyl)benzene; nitrobenzene; methyl benzoate; phenyl acetate; phenyl 2,2,2-trifluoroacetate; phenyl dihydrogen phosphate; 2H-pyran; 2H-thiopyran; biotin; benzene; benzoic acid; isonicotinic acid; or nicotinic acid.

The invention comprises tail-polyamides capable of entering a cell and the nucleus of the cell. In certain preferred embodiments, a tail-polyamide has a tail structure that enhances the ability of the polyamide to enter a cell and/or the nucleus of the cell when compared to the polyamide without the tail structure. A tail-polyamide is preferably capable of entering a cell of one type or more than one type. In certain embodiments, tail-polyamides are useful for modulating gene expression in a cell in culture or in a cell in an animal, a plant or a human. In certain other embodiments, tail-polyamides are useful for modulating gene expression in a patient to ameliorate a disease symptom.

The invention further provides methods of using a tail-polyamide as a research tool and for therapeutic methods in humans, animals, and/or plants. Methods of the current invention preferably comprise administering a tail-polyamide of the invention to a cell, a human, an animal and/or a plant to modulate the expression of a gene and/or to modulate physiological processes linked to the expression of a gene.

4.0 BRIEF DESCRIPTION OF THE DRAWINGS

FIG. 1: Structures of polyamide-fluorescein conjugates 1-3. Polyamides 1 and 3 target the sequence 5'-WTWCGW-3', while polyamide 2 targets the sequence 5'-WGGWCW-3'. Polyamide 3 differs from 1 and 2 in the linker region between the polyamide core sequence and the fluorescein moiety. Open circles designate N-methylpyrrole, closed circles designate N-methylimidazole, squares designate 3-chlorothiophene and diamonds designate β-alanine.

Figure 2:
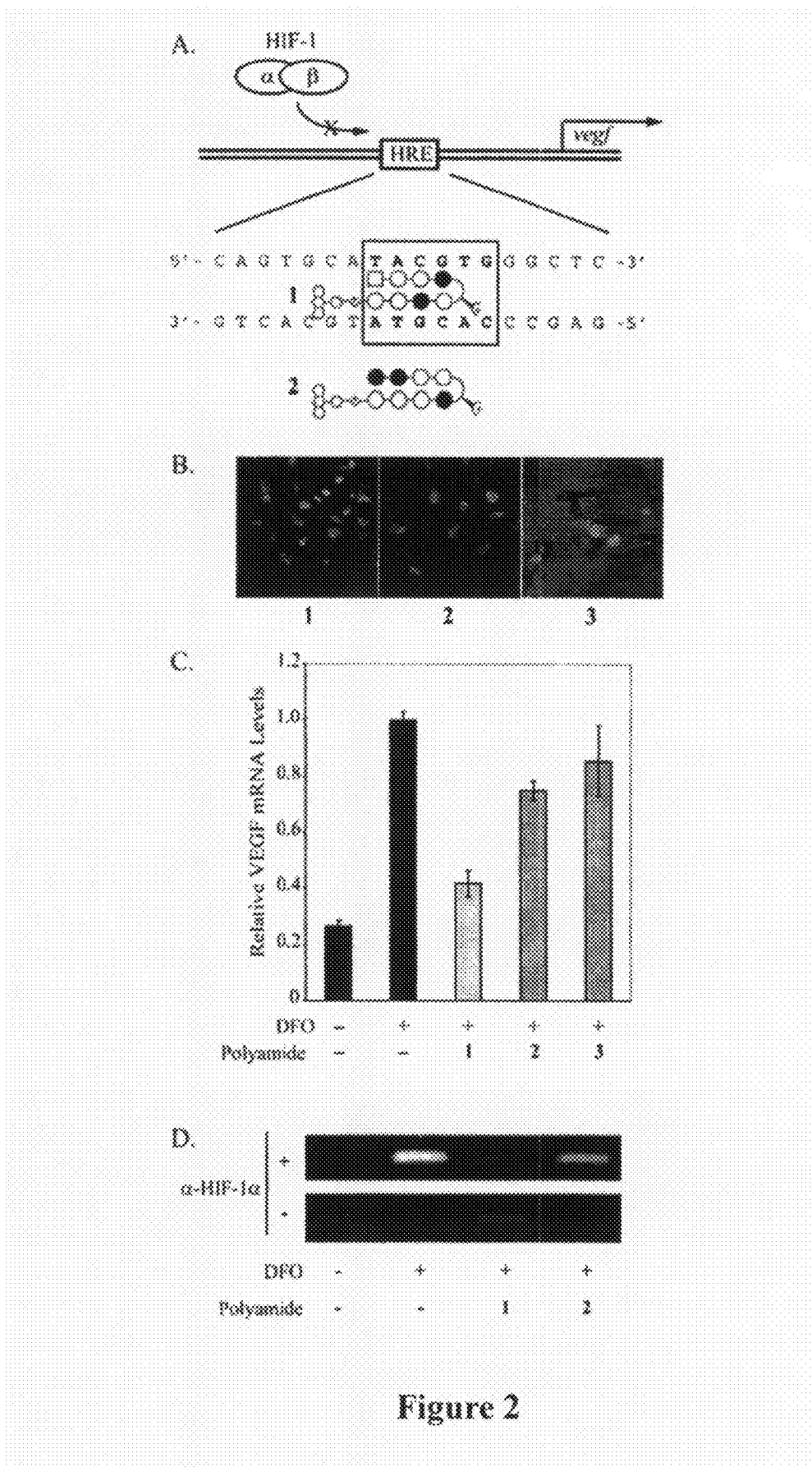

FIG. 2: (A) Schematic illustration of polyamide 1 binding to the VEGF HRE (SEQ ID NO:1). (B) Uptake of polyamides 1-3 in HeLa cells. Polyamides 1 (left) and 2 (center) localize in the nucleus while polyamide 3 (right) localizes in the nucleus to a limited extent but is largely extracellular. (C) Induction of VEGF mRNA by the hypoxia mimetic deferoxamine (DFO) in the presence of polyamides 1-3 measured by quantitative real-time PCR. Polyamide 1 inhibits the expression of DFO-induced VEGF expression. Polyamides 2 and 3 have a more modest effect. (D) Chromatin immunoprecipitation assays using HeLa cells with anti-HIF1□ or mock antibody treatment are consistent with inhibition of HIF-1 binding to the VEGF HRE in the presence of polyamide 1, and, to a more modest degree, 2. Concentrations of polyamides are 1 μM.

Figure 3A:
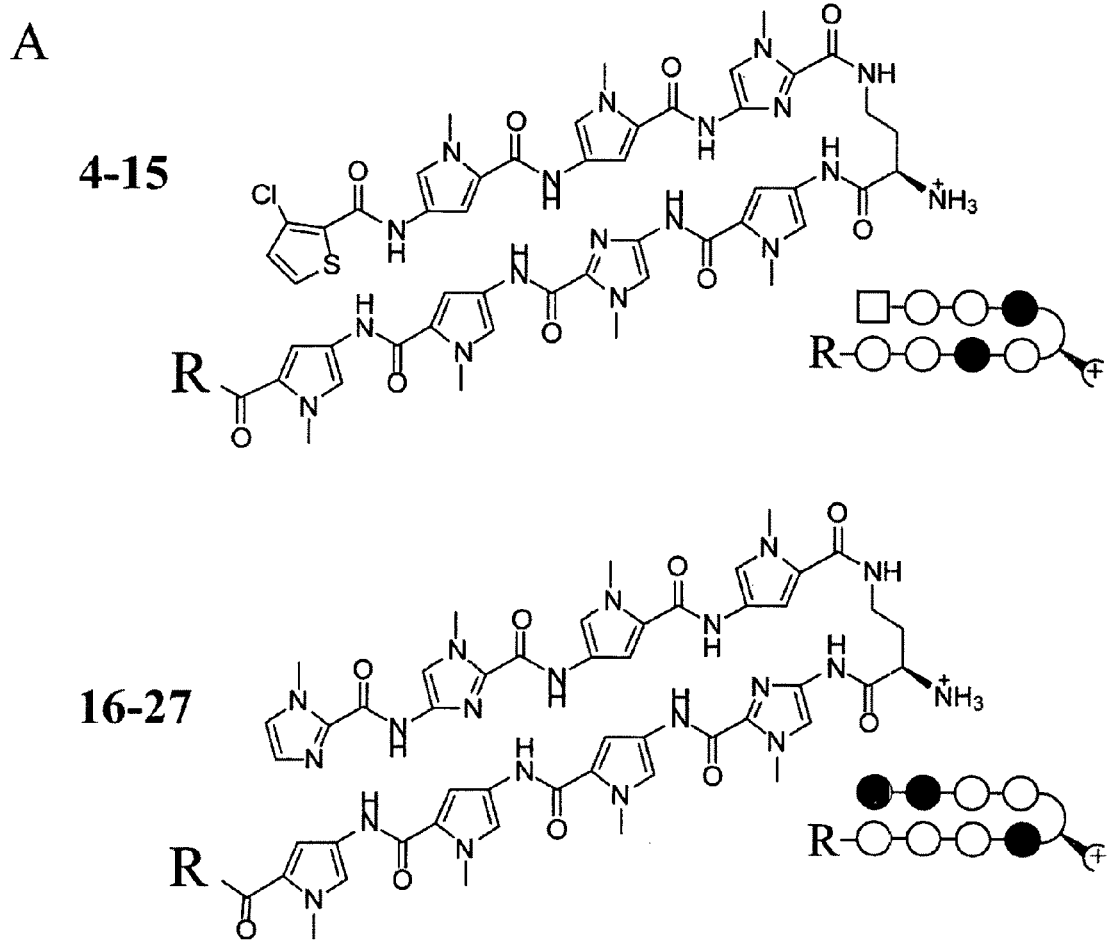
Figure 3B:
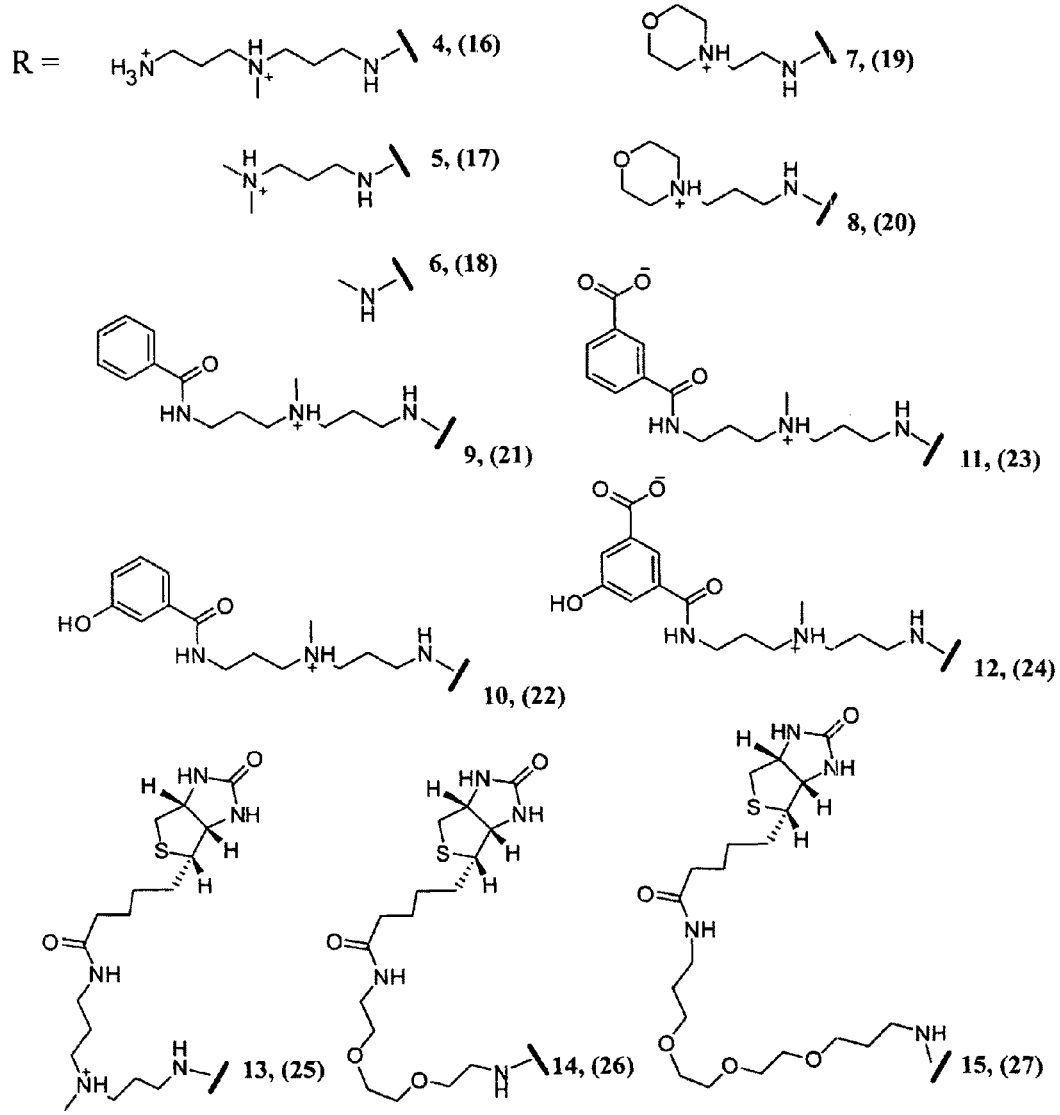

FIG. 3: Structures of polyamides 4-27. Polyamides 4-15 target 5'-WTWCGW-3' DNA sequences; 16-27 target 5'-WGGWCW-3'.

Figure 4A:
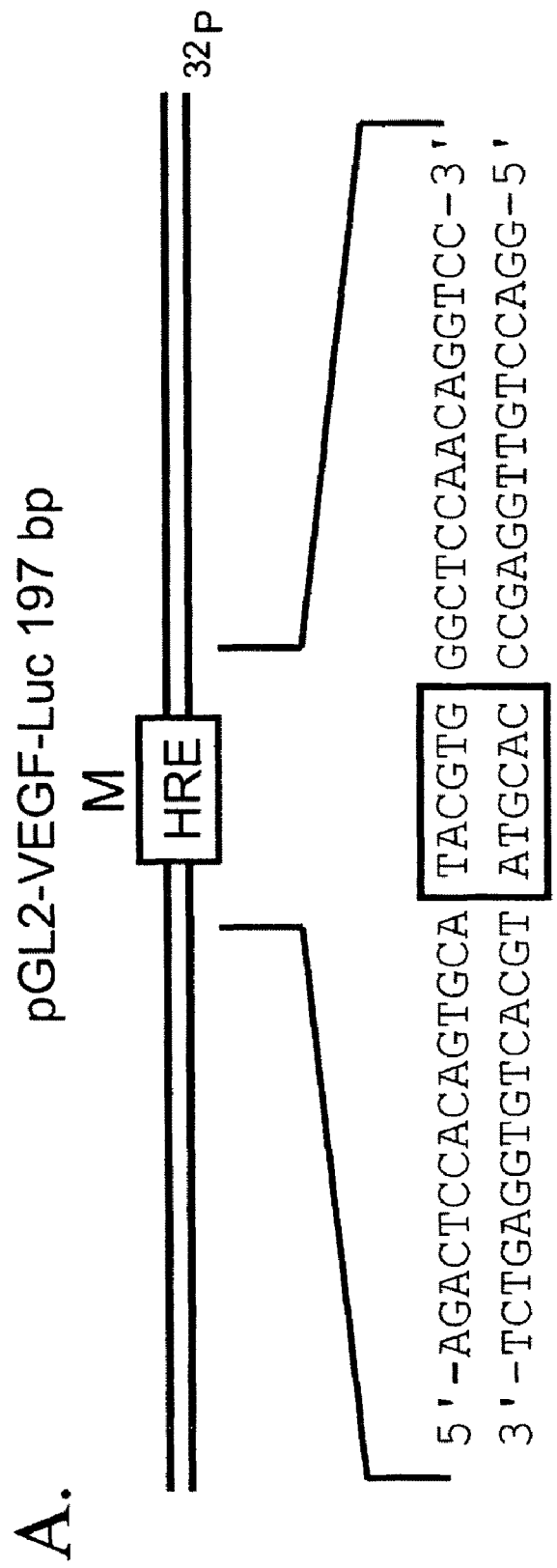
Figure 4B:
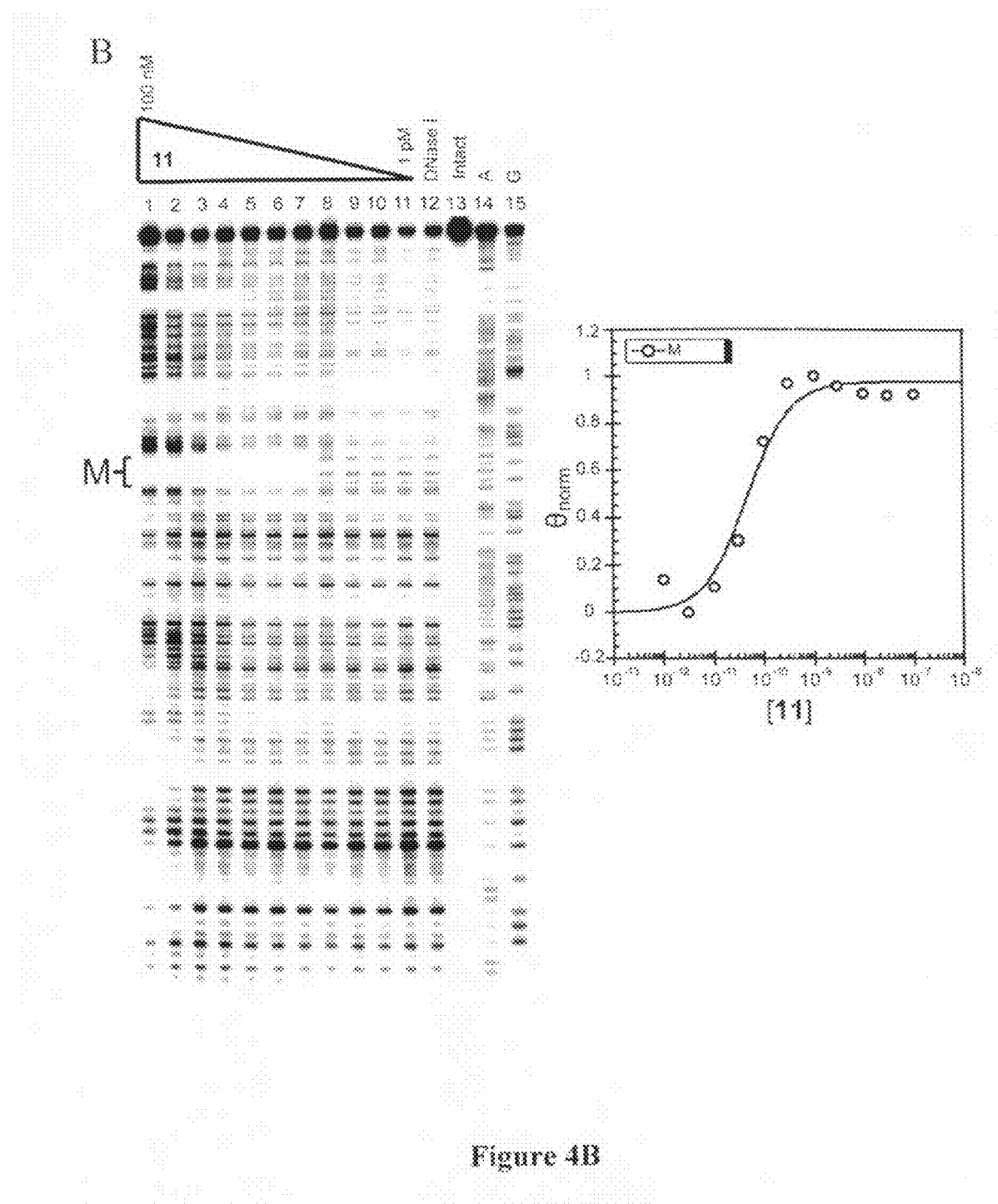
Figure 4C:
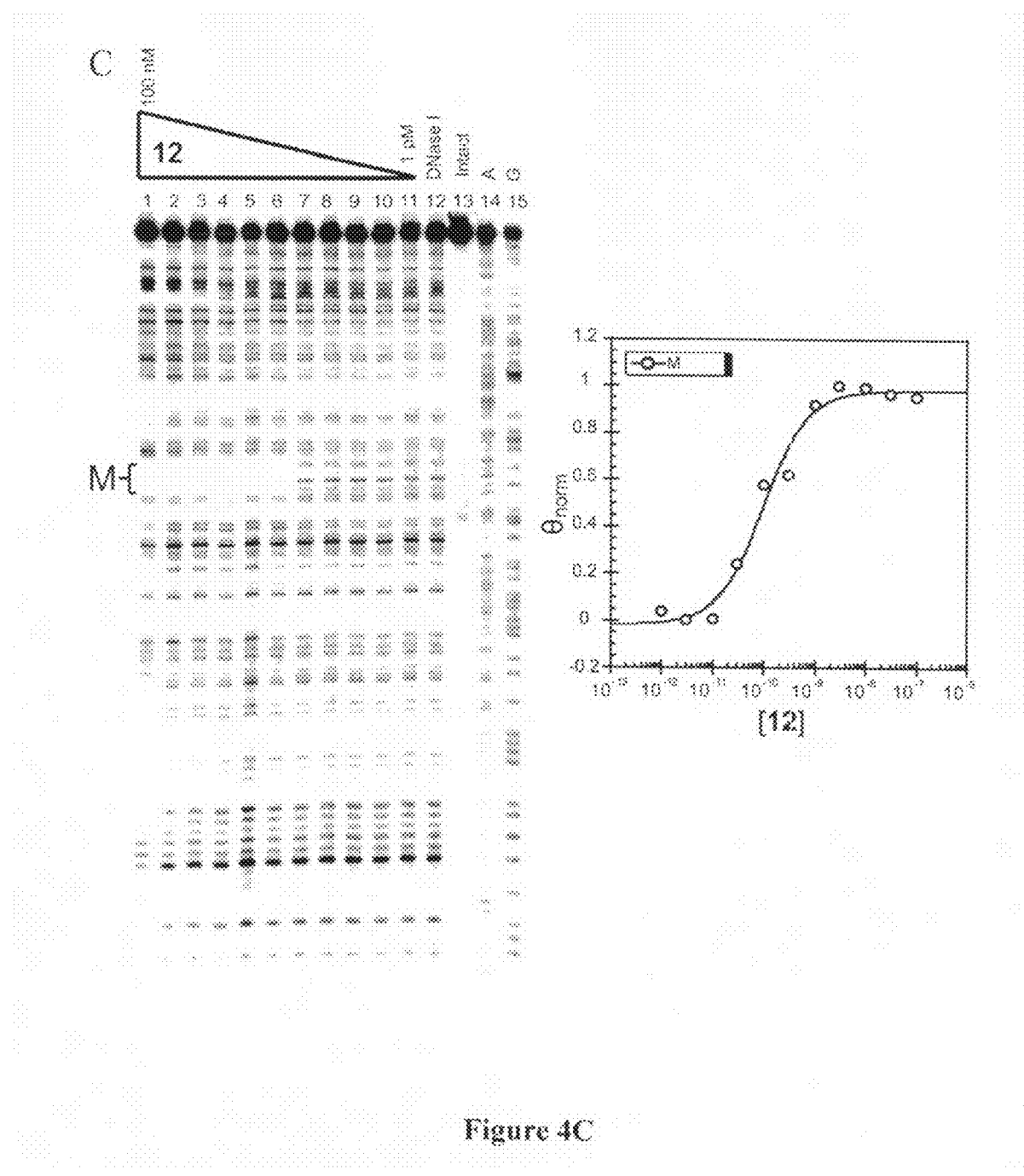

FIG. 4: Plasmid sequence and DNA-binding properties of polyamides 11 and 12. (A) Illustration of plasmid pGL2-VEGF-Luc. The HRE match binding site M is indicated by the box (SEQ ID NO:2). (B and C) Quantitative DNase I footprint titration experiments for polyamides 11 (B) and 12 (C) on the 197 bp, 5'-end-labeled PCR product of plasmid pGL2-VEGF-Luc: lanes 1-11, 100 nM, 30 nM, 10 nM, 3 nM, 1 nM, 300 pM, 100 pM, 30 pM, 10 pM, 3 pM and 1 pM polyamide, respectively; lane 12, DNase I standard; lane 13, intact DNA; lane 14, A reaction; lane 15, G reaction. Each footprinting gel is accompanied by a binding isotherm for polyamides binding the match site M (below).

Figure 5:
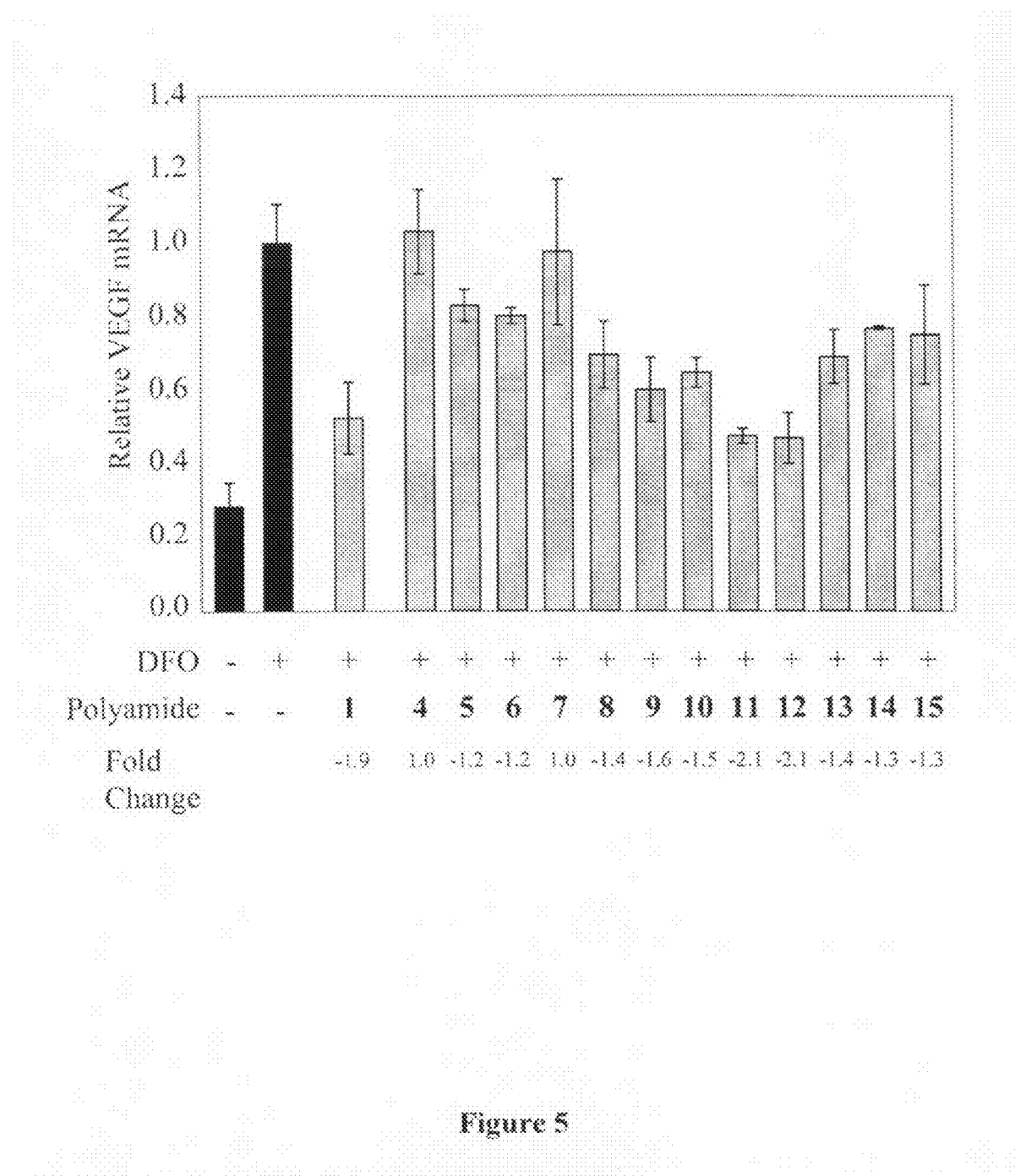

FIG. 5: Induction of VEGF mRNA by the hypoxia mimetic deferoxamine (DFO) in the presence of polyamides 1 and 4-15 measured by quantitative real-time PCR. Concentrations of polyamides are 1 μM.

Figure 6:
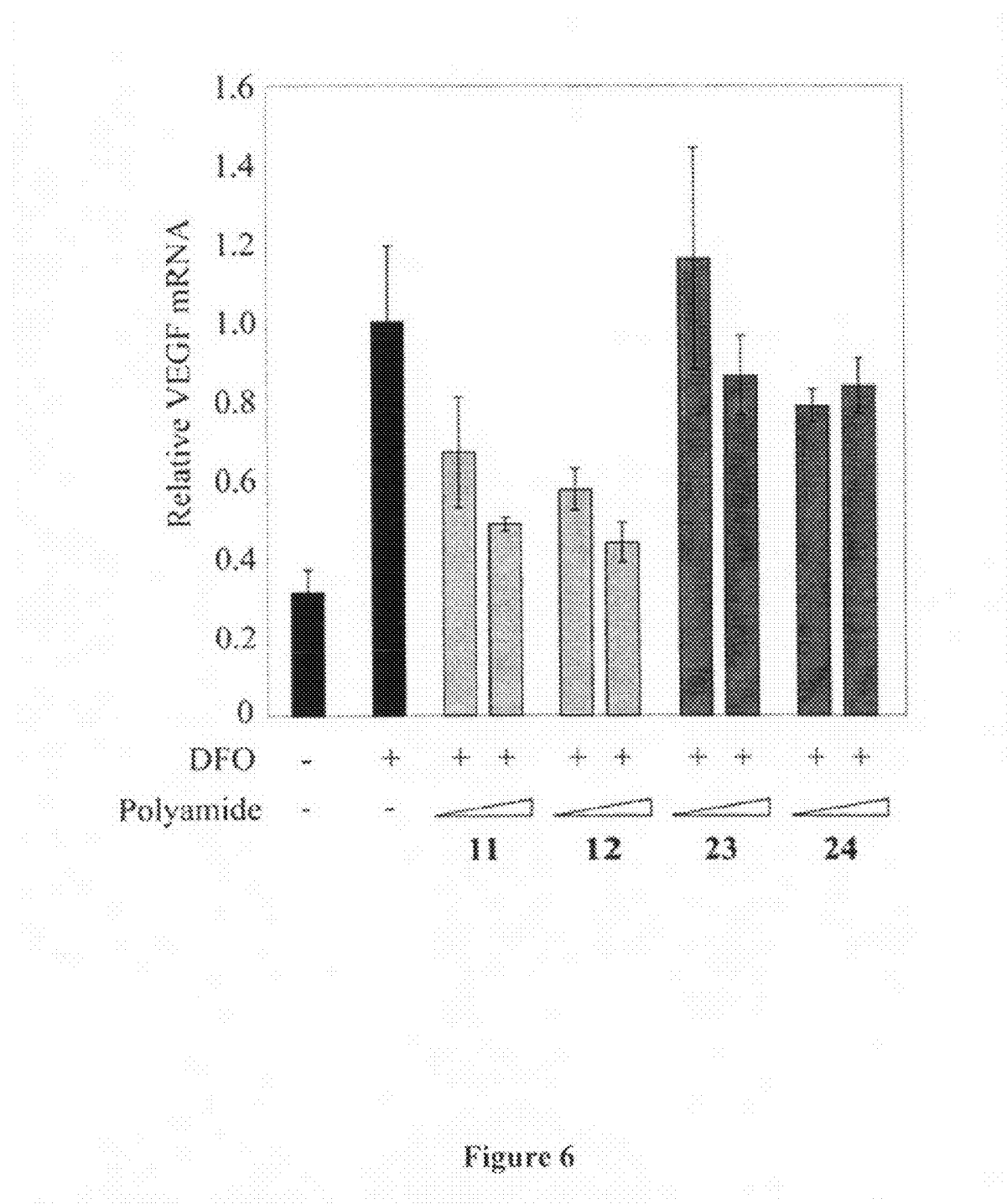

FIG. 6: Induction of VEGF mRNA by the hypoxia mimetic deferoxamine (DFO) in the presence of polyamides 11, 12, 23 and 24 measured by quantitative real-time PCR. Polyamides 11 and 12, which bind the 5'-ATACGT-3' sequence found in the VEGF HRE, show inhibition of DFO-induced VEGF expression. Polyamides 23 and 24, which target 5'-WGGWCW-3', have a more modest effect. Concentrations of polyamides are 0.2 and 1 μM.

Figure 7:
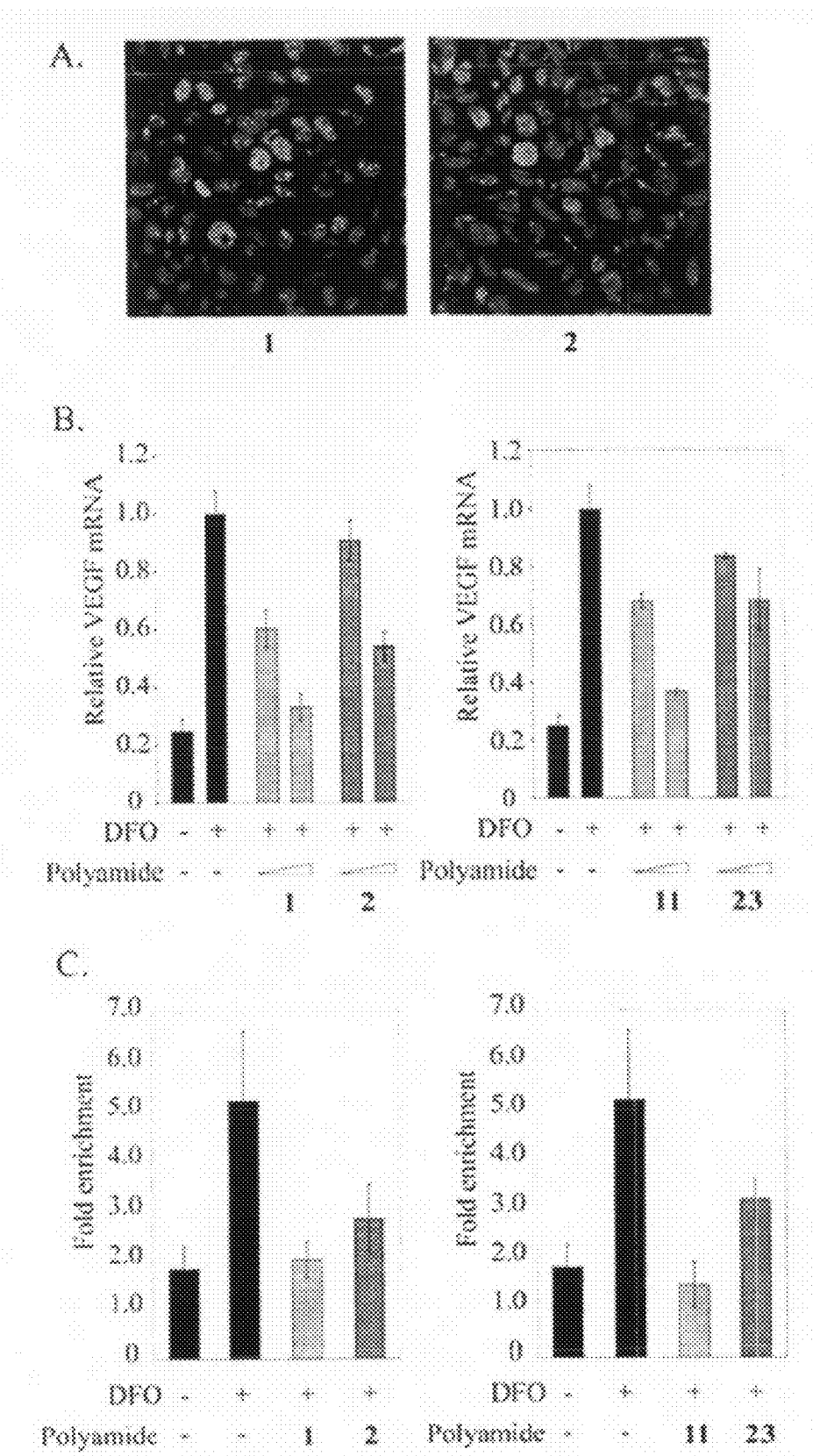

FIG. 7: (A) Uptake of polyamides 1 (left) and 2 (right) in U251 cells. (B) Induction of VEGF mRNA by the hypoxia mimetic deferoxamine (DFO) in the presence of polyamides 1, 2, 11 and 23 in U251 cells measured by quantitative real-time PCR. Concentrations of polyamides are 0.2 and 1 μM. (C) Chromatin immunoprecipitation assays with anti-HIF1α or mock antibody treatment expressed as fold-enrichment (specific/mock) of a 120 bp sequence at the VEGF HRE measured by real-time PCR. Concentrations of polyamides are 1 μM.

FIG. 8: (A-J): Quantitative DNase I footprint titration experiments for polyamides 5, 6, 7, 8, 9, 10, 13, 14, and 15 on the 197 bp, 5'-end-labeled PCR product of plasmid pGL2-VEGF-Luc: lanes 1-11, 100 nM, 30 nM, 10 nM, 3 nM, 1 nM, 300 pM, 100 pM, 30 pM, 10 pM, 3 pM and 1 pM polyamide, respectively; lane 12, DNase I standard; lane 13, intact DNA; lane 14, A reaction; lane 15, G reaction. Each footprinting gel is accompanied by a binding isotherms (below) for the HRE match binding site, indicated by M.

Figure 9:
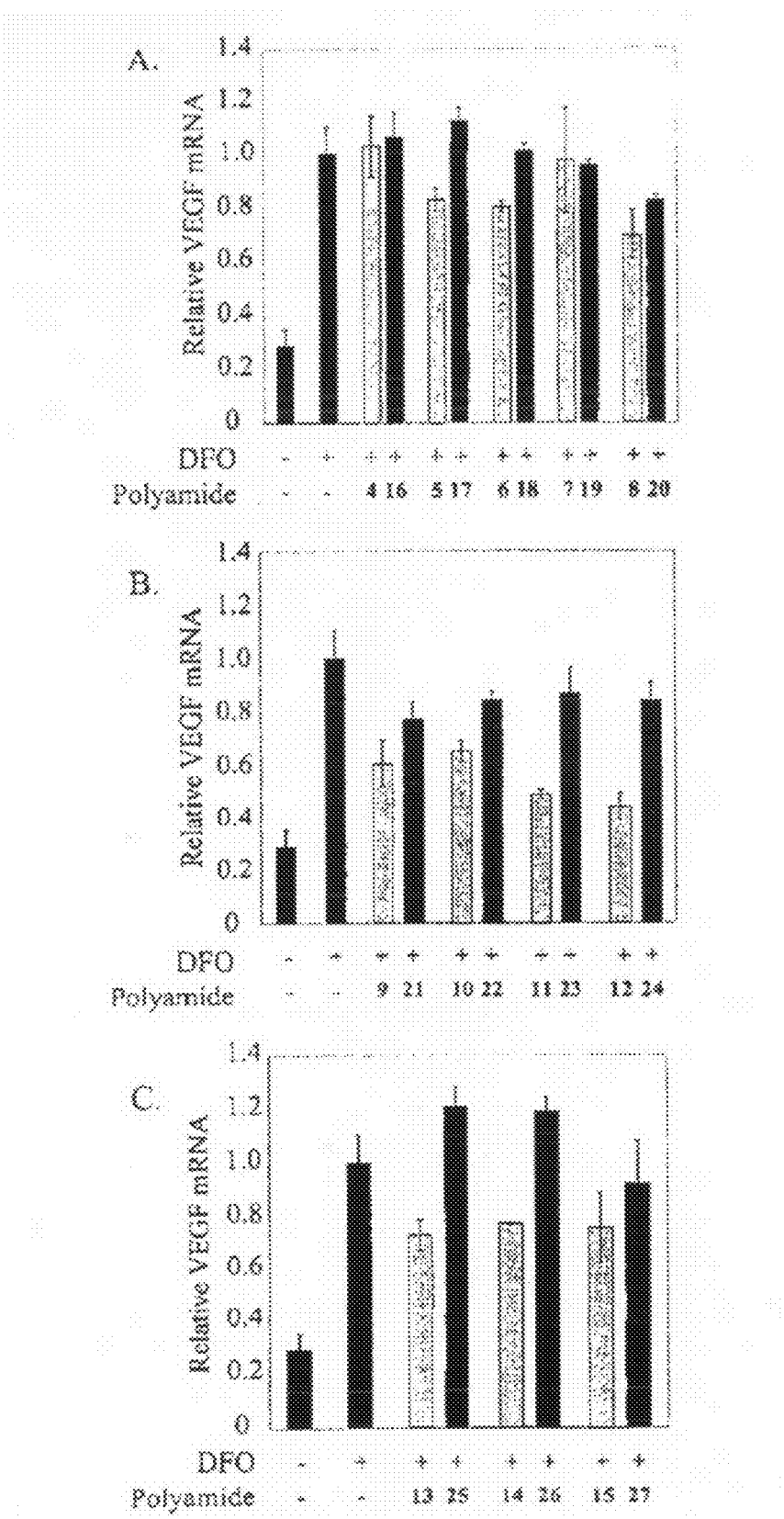

FIG. 9: (A) Induction of VEGF mRNA by the hypoxia mimetic deferoxamine (DFO) in the presence of polyamides 4-8 and 16-20 measured by quantitative real-time PCR. All concentrations are 1 μM. (B) As in (A) except for polyamides 9-12 and 21-24. (C) As in (A) except for polyamides 13-15 and 25-27.

Figure 10:
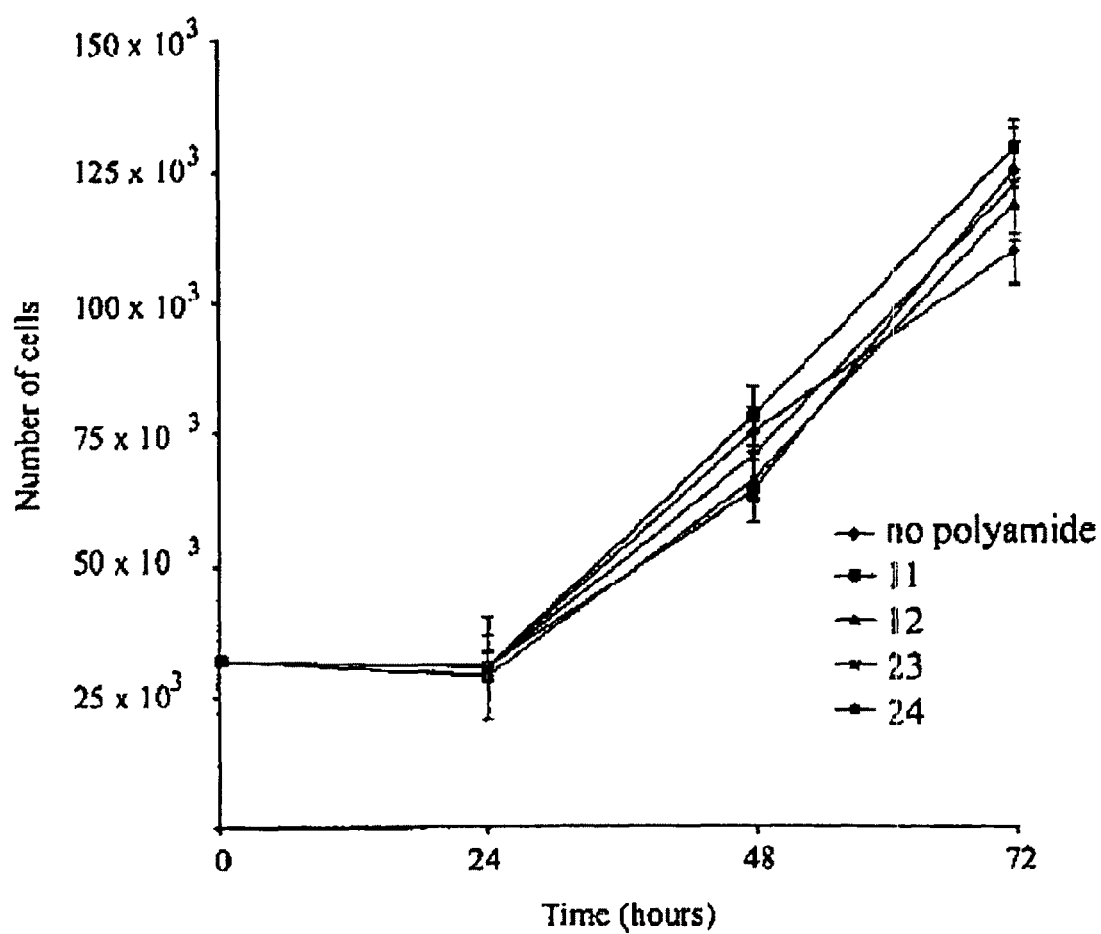

FIG. 10: HeLa cell growth in the presence of polyamides 11, 12, 23, and 24 at 1 μM as a function of time. Cells were counted at 24 hour intervals using a hemacytometer.

Figure 11A:
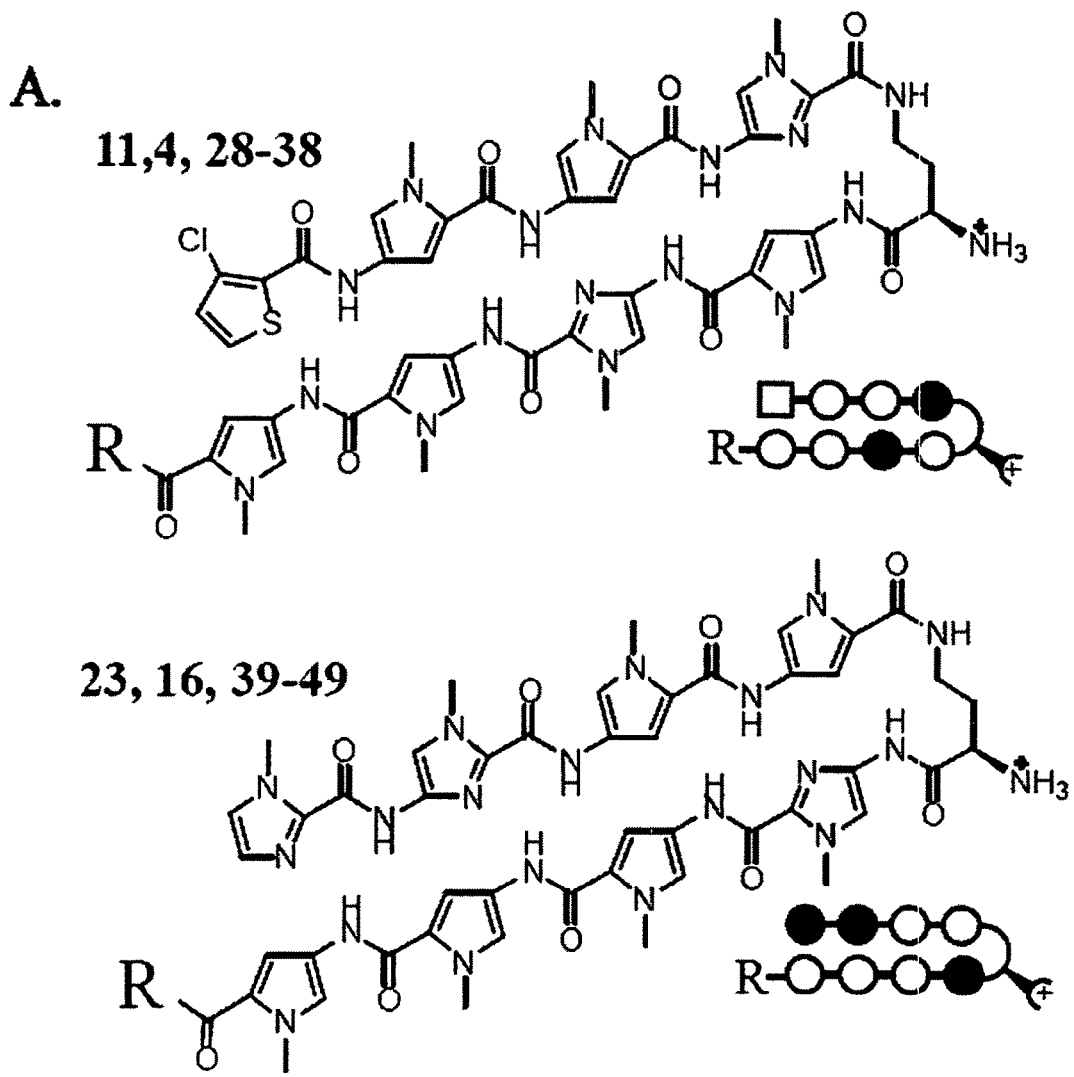

FIG. 11: Structures of polyamides 4, 11, 28-38 and 16, 23, 39-49. Polyamides 4, 11, 28-38 target 5'-WTWCGW-3' DNA sequences; 16, 23, 39-49 target 5'-WGGWCW-3'.

Figure 12A:
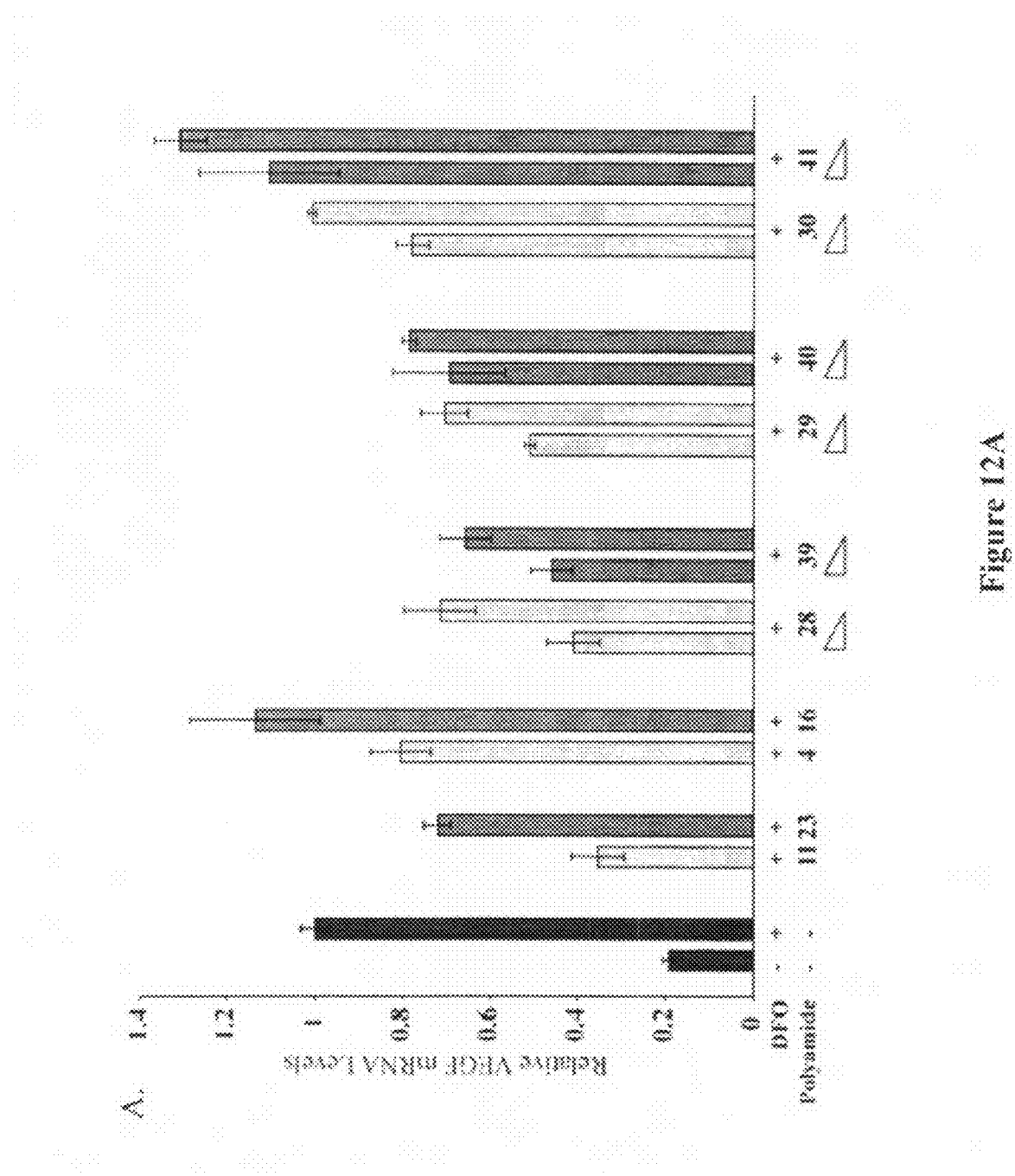
Figure 12B:
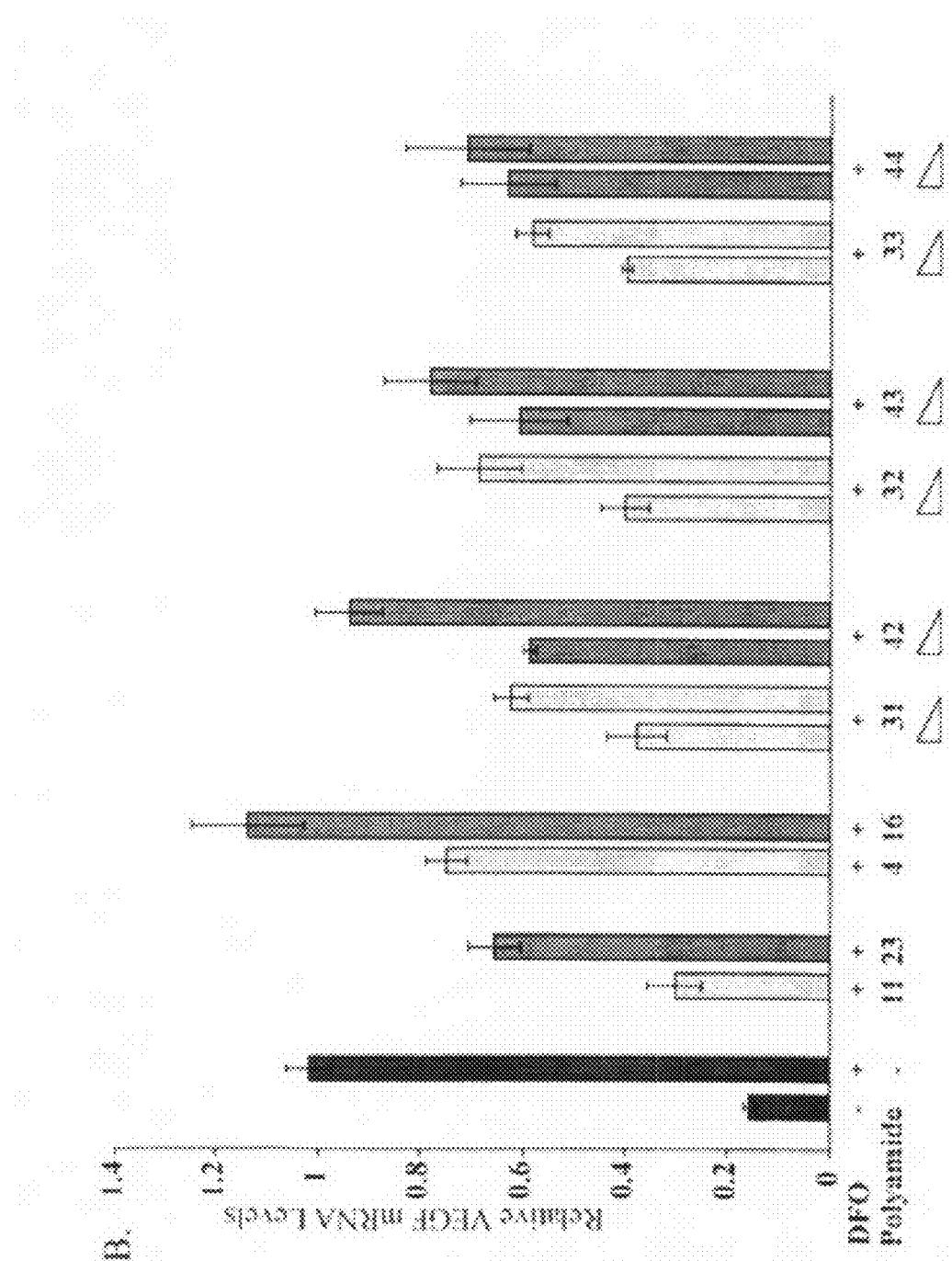
Figure 12C:
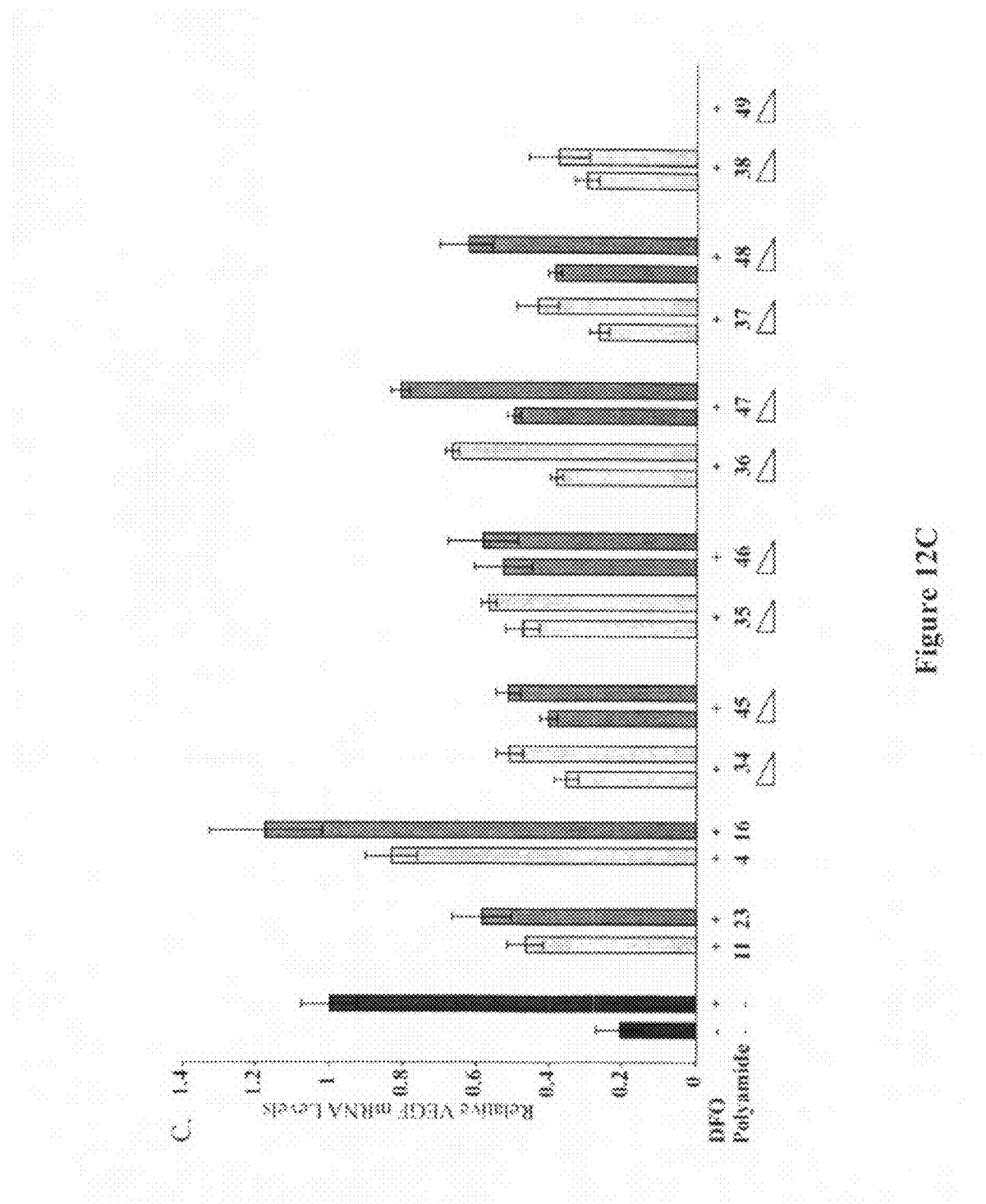

FIG. 12: (A) Induction of VEGF mRNA by the hypoxia mimetic deferoxamine (DFO) in the presence of polyamides 11, 4, 28-30, and their respective mismatch congeners, 23, 16, 39-41 in U251 cells measured by quantitative real-time PCR. Concentrations of polyamides are 0.2 and 1 μM. (B) Induction of VEGF mRNA by the hypoxia mimetic deferoxamine (DFO) in the presence of polyamides 11, 4, 31-33, and their respective mismatch congeners, 23, 16, 42-44 in U251 cells measured by quantitative real-time PCR. Concentrations of polyamides are 0.2 and 1 μM. (C) Induction of VEGF mRNA by the hypoxia mimetic deferoxamine (DFO) in the presence of polyamides 11, 4, 34-38, and the mismatch congeners, 23, 16, 45-49 in U251 cells measured by quantitative real-time PCR. Concentrations of polyamides are 0.2 and 1 μM.

FIG. 13. Structures of molecules used in this study. a) Structures of polyamides 11.1-11.3 and echinomycin. Imidazole, pyrrole and chlorothiophene monomer units are represented, respectively, by closed circles, open circles and squares. b) Three approaches to inhibiting HIF-1 induced gene expression: sequence-specific small molecule binding to the HRE (SEQ ID NO:1) by a polyamide or echinomycin, and reduction in HIF-1α mRNA using siRNA.

FIG. 14. Quantitative DNase I footprint titration experiments for polyamides 1-3 and echinomycin. a) Illustration of pGL2-VEGF-Luc and partial sequence containing the VEGF HRE (SEQ ID NO:2) and putative binding sites for polyamides 11.1, 11.2 and echinomycin. b) Quantitative DNase I footprint titration experiments for polyamides 11.1, 11.2, 11.3, and echinomycin, E, on the 5'-end-labeled PCR product of plasmid pGL2-VEGF-Luc. For polyamides 11.1, 11.2, and 11.3: lanes 1-11, 100 nM, 30 nM, 10 nM, 3 nM, 1 nM, 300 pM, 100 pM, 30 pM, 10 pM, 3 pM and 1 pM polyamide, respectively; lane 12, DNAse I standard; lane 13, intact DNA; lane 14, A reaction; lane 15, G reaction. For echinomycin, E: lanes 1-11, 10 μM, 3 μM, 1 μM, 300 nM, 100 nM, 30 nM, 10 nM, 3 nM, 1 nM, 300 pM, 100 pM echinomycin, respectively; lanes 12-15 as above. Polyamide 1 and echinomycin have $K_a=2.6(\pm 0.4)\times 10^{10}$ M$^{-1}$ and $K_a=8.4(\pm 2.1)\times 10^6$ M$^{-1}$, respectively, at the VEGF HRE. Polyamide 11.2 has $K_a=3.2(\pm 0.6)\times 10^9$ M$^{-1}$ for the site 5'-AGTGCA-3' immediately 5' to the VEGF HRE. Polyamide 11.3 has $K_a=8.0(\pm 1.0)\times 10^8$ M$^{-1}$ for the VEGF HRE. c) Illustration of pCSJ-FLT1 and partial sequence containing the FLT1 HRE (SEQ ID NO:3) and putative binding sites for polyamides 11.1 and echinomycin. d) Quantitative DNase I footprint titration experiments for polyamides 11.1, 11.2, 11.3, and echinomycin, E, on the 5' end-labeled PCR product of plasmid pCSJ-FLT1. Lane assignments for gels shown in d) are as described for b). Polyamide 11.1 and echinomycin have $K_a=2.7(\pm 0.2)\times 10^9$ M$^{-1}$ and $K_a=2.9(\pm 0.7)\times 10^7$ M$^{-1}$, respectively, at the FLT1 HRE. Polyamide 11.2 has $K_a=2.2(\pm 0.8)\times 10^8$ at this site. Polyamide 11.3 does not bind the FLT1 HRE with a measurable $K_a$.

Figure 15:
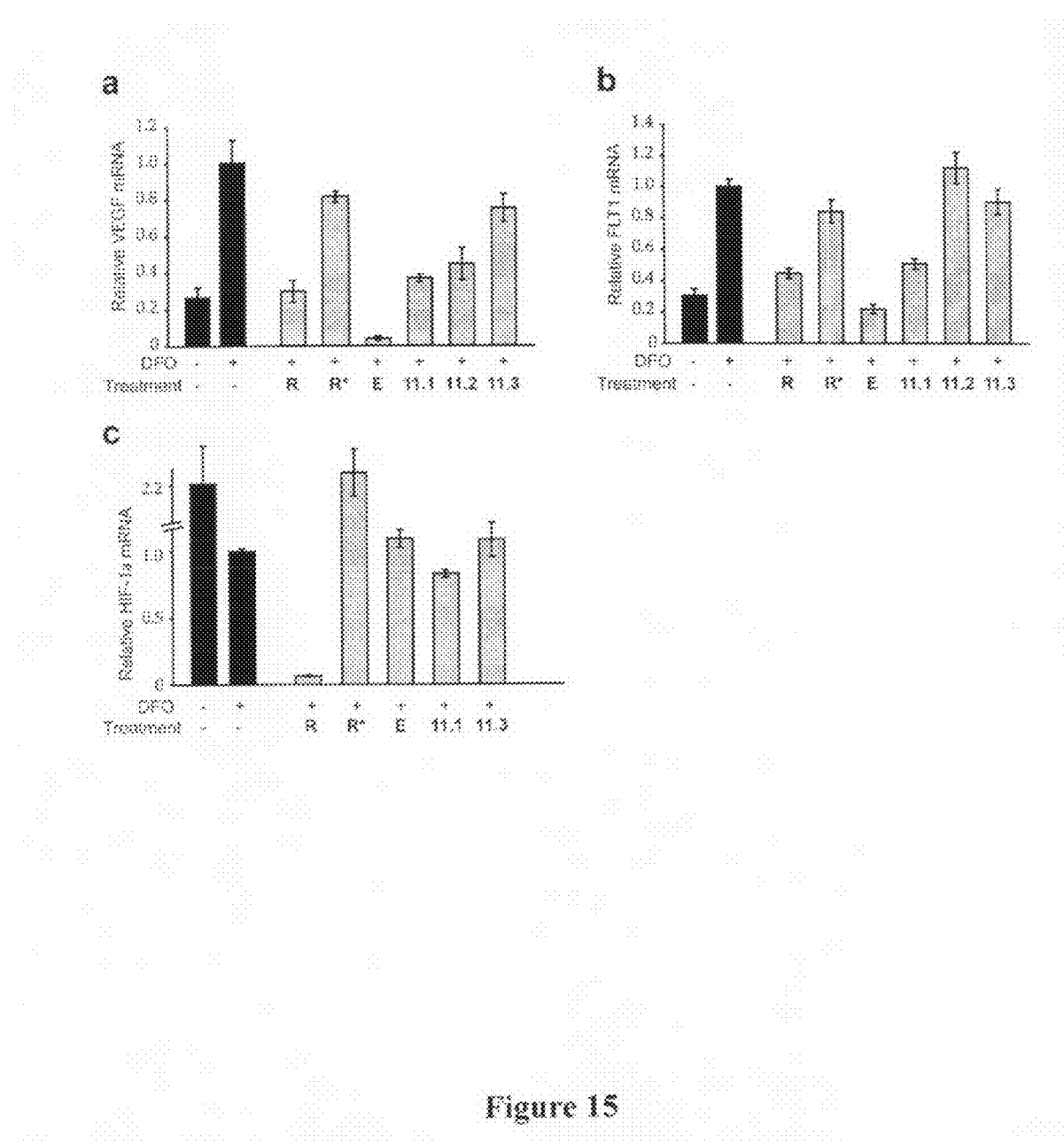

FIG. 15. Quantitative real-time PCR measurements. a) Induction of VEGF mRNA by the hypoxia mimetic deferoxamine (DFO) measured by quantitative real-time PCR: HIF-1α siRNA R; mismatch control siRNA, R*; echinomycin (100 nM), E; and polyamides 11.1, 11.2, and 11.3 (10 μM). Treatment with siRNA, 11.1, or 11.2 decrease VEGF mRNA levels to near non-induced levels. Echinomycin potently inhibits VEGF mRNA to below non-induced levels. Polyamide 11.3 has a more modest effect. b) Induction of FLT1 mRNA by DFO measured by quantitative real-time PCR: HIF-1α siRNA R; mismatch control siRNA, R*; echinomycin (100 nM), E; and polyamides 11.1, 11.2, and 11.3 (1 μM). The siRNA, echinomycin, and 11.1 decrease FLT1 mRNA levels. Polyamides 11.2 and 11.3 have minimal or no effect. c) Measurement of HIF-1α mRNA by quantitative real-time PCR: HIF-1α siRNA; mismatch control siRNA, R*; echinomycin (100 nM), E; and polyamides 11.1, 11.3 (1 μM). Treatment with siRNA decreases HIF-1α mRNA by more than 95%.

Figure 16A:
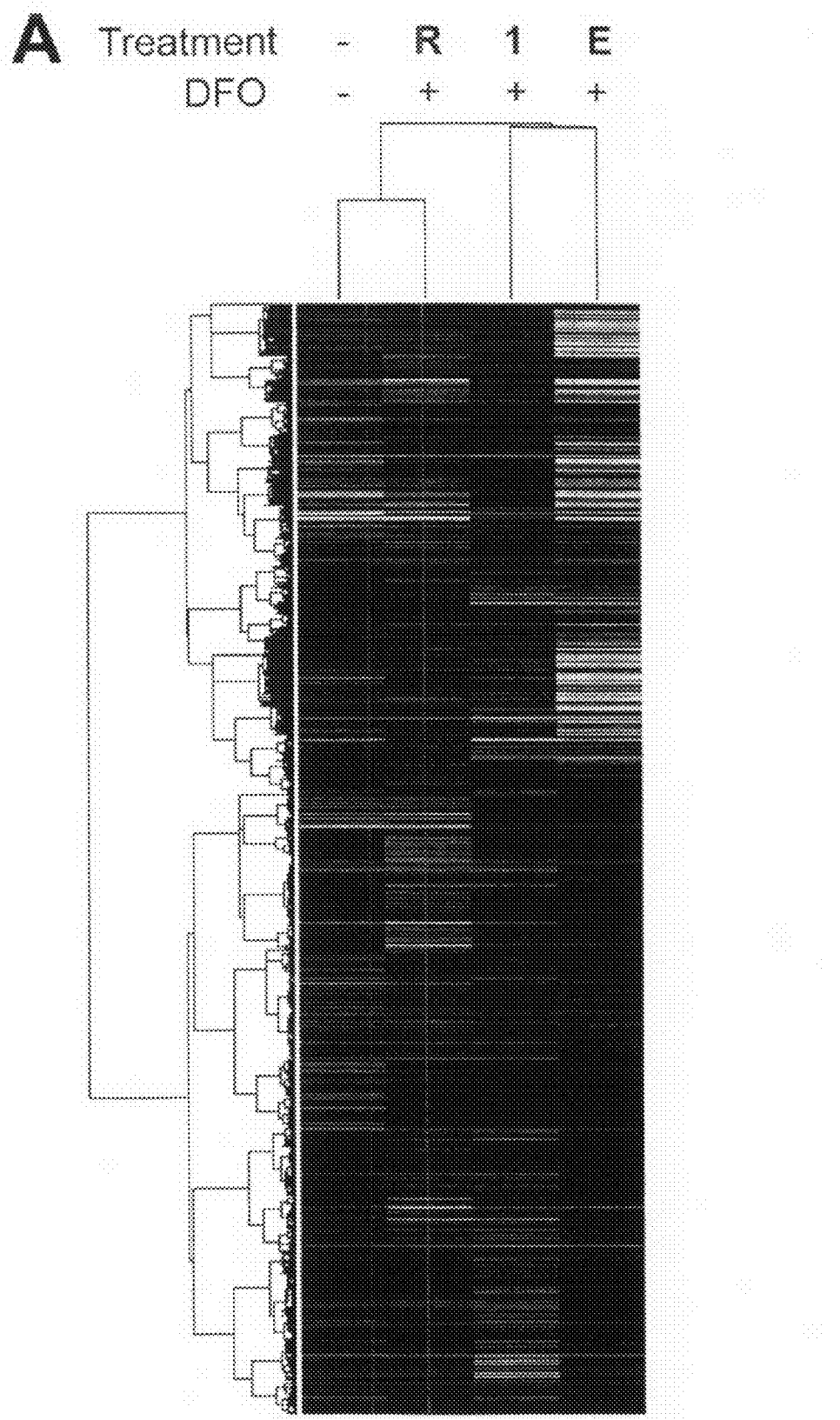
Figure 16B:
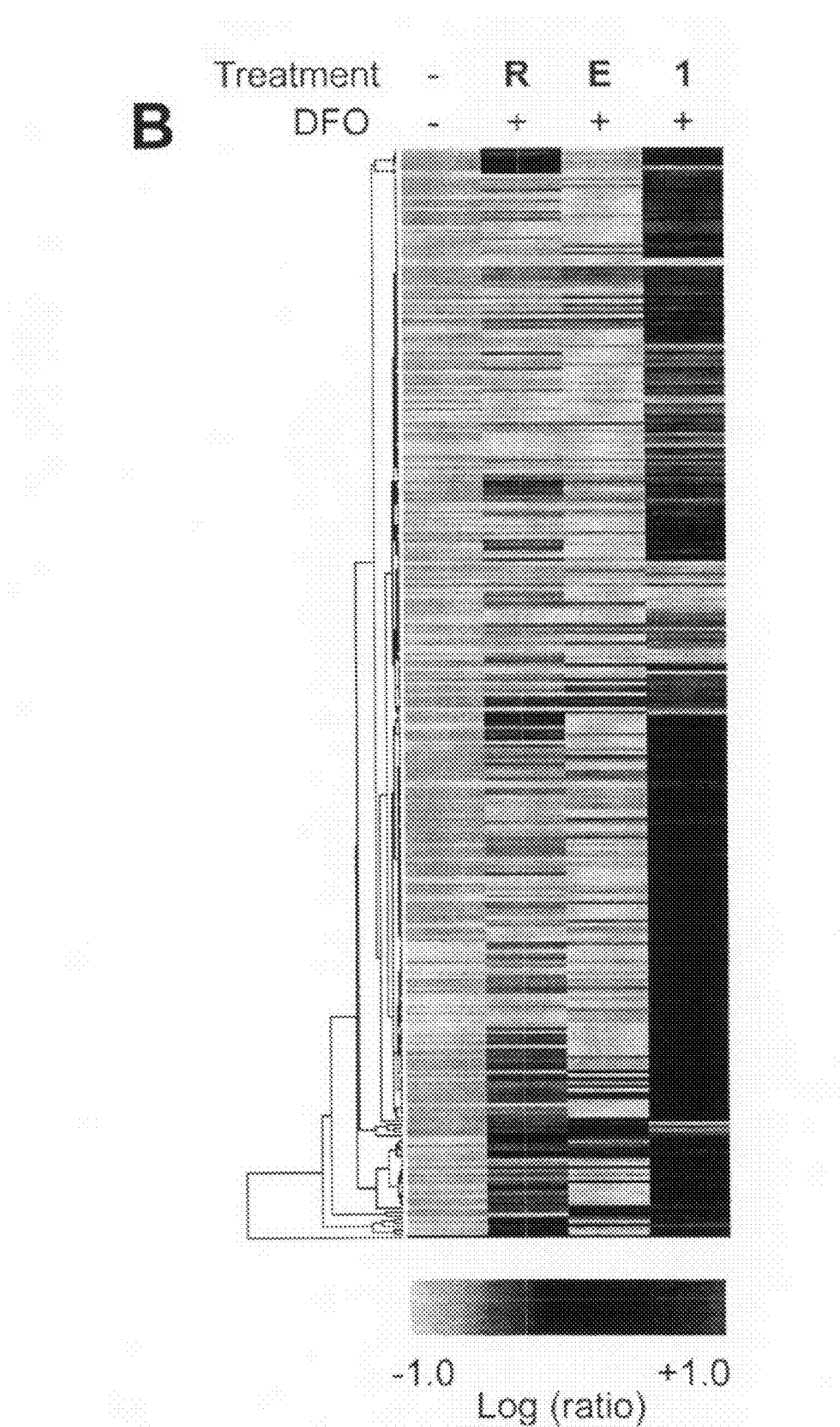
Figure 16D:
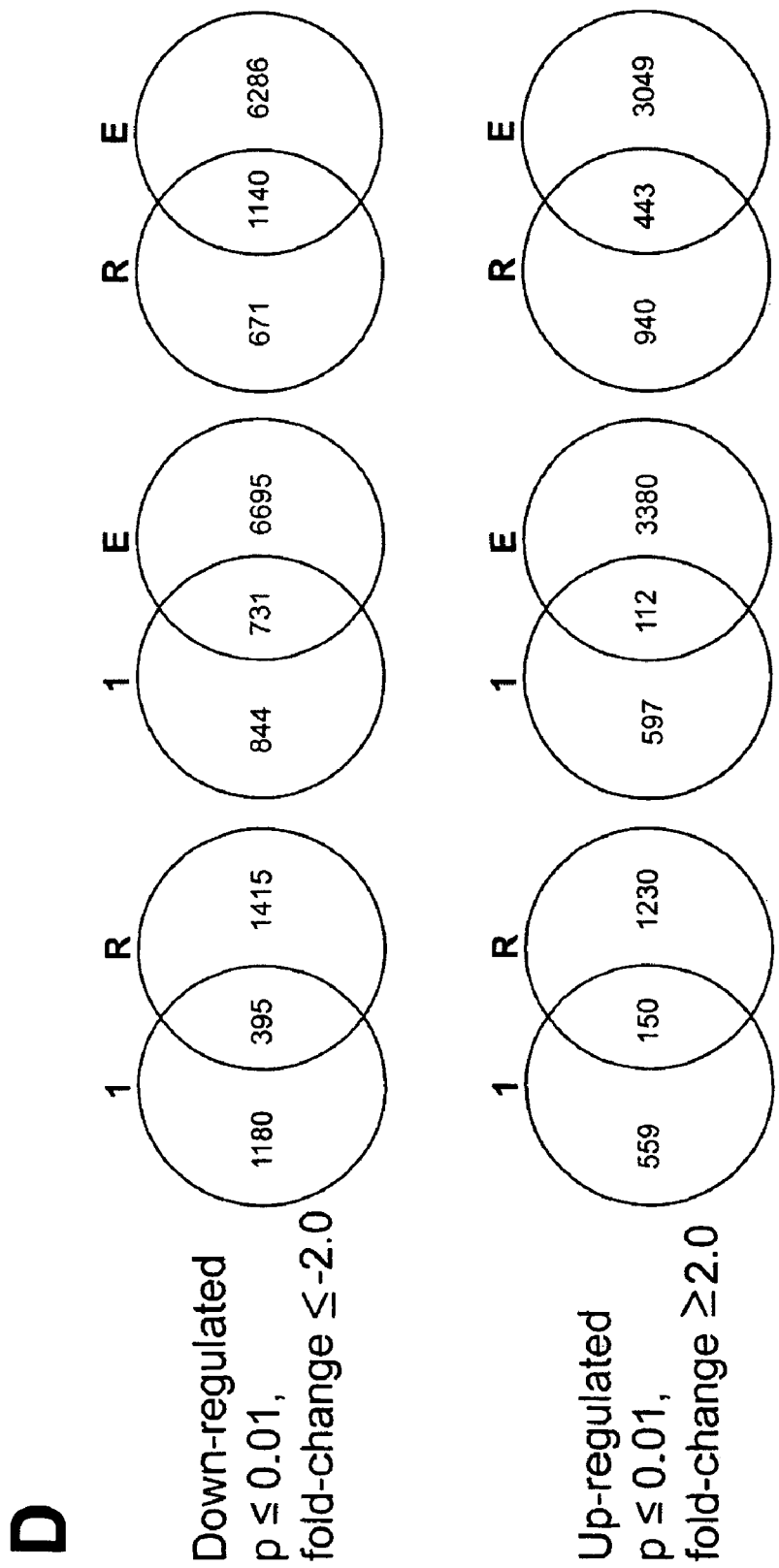

FIG. 16. Microarray analysis of gene expression. a) Divisive clustering analysis over all interrogated transcripts for DFO-induced cells: HIF-1α siRNA, R; echinomycin (100 nM), E; and polyamides 11.1 (10 µM) (designated as 1 in FIG. 16). b) Agglomerative clustering analysis over all 297 transcripts induced by DFO at least 4-fold ($p \leq 0.01$). Of this transcript set, HIF-1α siRNA inhibited 244, echinomycin inhibited 263, and polyamide 11.1 inhibited 69 by $\geq$2-fold ($p \leq 0.01$). c) Effects of the indicated treatments on a panel of genes previously characterized as direct targets of HIF-1 and also induced by DFO at least 1.5-fold ($p \leq 0.01$) in this experiment. Treatments reported are an error-weighted average from three experiments. d) Ven diagrams representing transcripts commonly down- and up-regulated (|fold-change|$\geq$2.0, $p \leq 0.01$) by 11.1 and HIF-1α siRNA, by 11.1 and echinomycin, and by HIF-1α siRNA and echinomycin. Numbers inside the intersections represent transcripts affected by both treatments.

Figure 17:
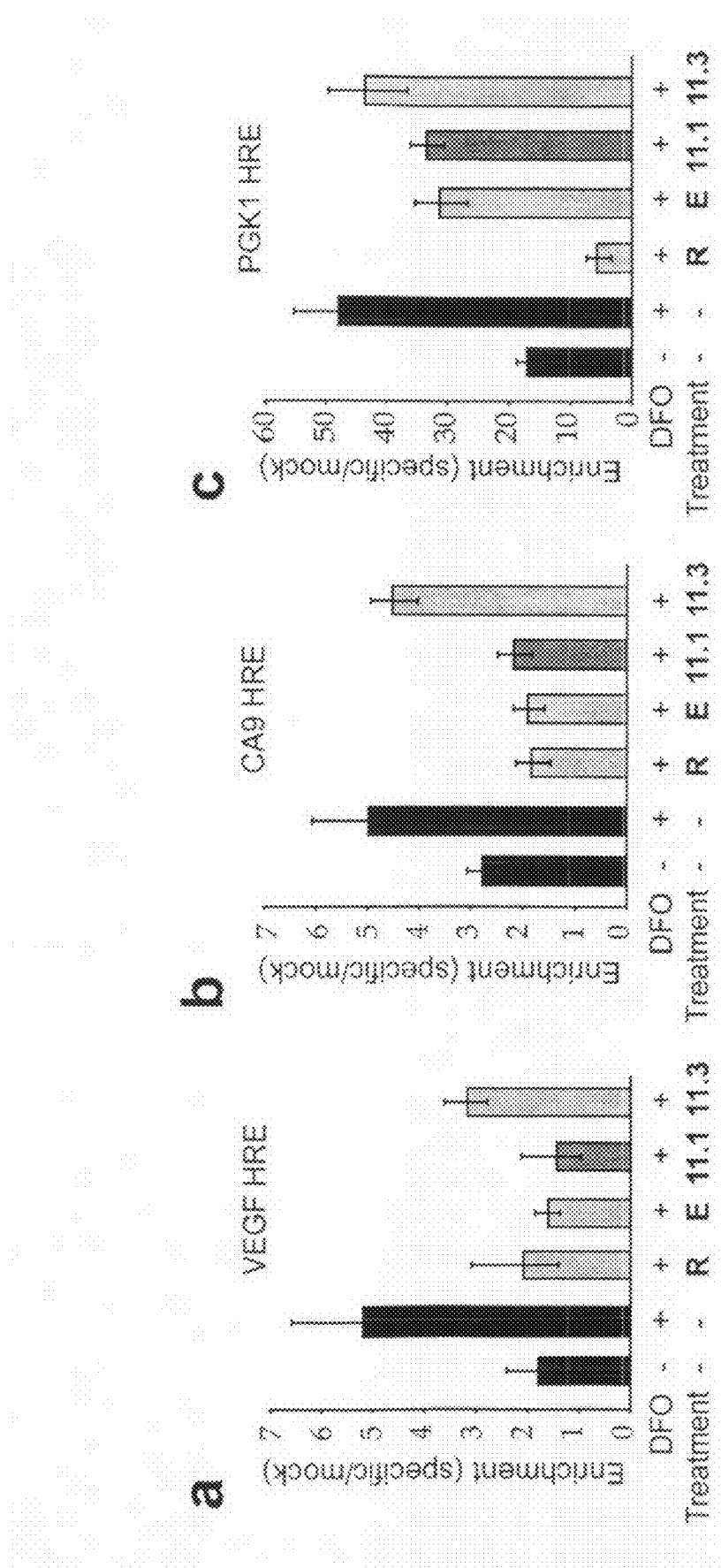

FIG. 17. Chromatin immunoprecipitation at three HREs. a) Chromatin immunoprecipitation of HIF-1α at the VEGF HRE following DFO treatment: HIF-1α siRNA, R; echinomycin (100 nM), E; and polyamides 11.1 and 11.3 (1 µM). Occupancy is decreased in the presence of R, E, and 11.1, but only modestly affected by 11.3. Chromatin immunoprecipitation of HIF-1α at the CA9 HRE (b), and PGK1 HRE (c).

5.0 DETAILED DESCRIPTION OF THE INVENTION

The present invention relates to polyamides with a tail structure, referred to herein as a tail-polyamide, and their use. A tail structure of a tail-polyamide of the invention, in certain embodiments, comprises a linker and an end-group. The structure of a tail-polyamide of the invention can be illustrated as A-B-C, with A representing an end-group of the tail, B representing a linker of the tail, and C representing a polyamide. An end-group of a tail-polyamide of the invention in certain embodiments has a structural element that resembles a part or parts of fluorescein.

A tail-polyamide according to certain embodiments is capable of entering a cell and the nucleus of the cell and preferably a living cell and the nucleus thereof. In certain preferred embodiments, a tail-polyamide has a tail structure that enhances the ability of the polyamide to enter a cell and/or the nucleus of the cell when compared to the polyamide without the tail structure. A tail-polyamide is preferably capable of entering a cell of one type or more than one type. In certain embodiments, tail-polyamides are useful for modulating gene expression in a cell in culture or in a cell in an animal, a plant or a human. In certain other embodiments, tail-polyamides are useful for modulating gene expression in a patient to ameliorate a disease symptom.

5.1 Tail Structures of Tail-Polyamides of the Invention

A tail structure of a tail-polyamide, in certain embodiments, comprises an end-group and a linker. In certain other embodiments, a tail structure includes a structure that resembles a structural element of fluorescein, for example, a benzene ring, a carboxylic acid, a methyl-, ethyl-, propyl-, butyl-, pentyl-, or hexyl-group, or any other structural element of fluorescein.

5.1.1 End-Groups of Tail Structures of the Invention

An end-group of a tail-polyamide of the invention, in certain embodiments, has a structural element that resembles a part or parts of fluorescein. An end-group in certain embodiments is a cyclic hydrocarbon, for example, an aromatic or an aliphatic cyclic hydrocarbon with a 5-ring or a 6-ring. In certain other embodiments, an end-group is an aromatic or non-aromatic heterocyclic organic compound with a 5-ring or a 6-ring of carbons and 1, 2 or 3 non-carbons, for example, nitrogen, oxygen and/or sulfur, or a mixture of nitrogen, oxygen and/or sulfur. An end-group in certain embodiments is isophthalic acid; phthalic acid; terephthalic acid; benzamide; morpholine; N,N-dimethylbenzamide; N,N-bis(trifluoromethyl)benzamide; fluorobenzene; (trifluoromethyl) benzene; nitrobenzene; methyl benzoate; phenyl acetate; phenyl 2,2,2-trifluoroacetate; phenyl dihydrogen phosphate; 2H-pyran; 2H-thiopyran; biotin; benzene; benzoic acid; isonicotinic acid; or nicotinic acid.

In certain other embodiments, an end-group is pyrimidine; furan; pyran; 2H-pyrrole; pyrazole; isothiazole; isoxazole; pyridine; pyrazine; pyridazine; piperidine; piperazine; pyrrolidine; pyrroline; imidazolidine; imidazoline; pyrazolidine; pyrazoline; or furazan. In certain other embodiments, an end-group is naphthoic acid; purine; indolizine; isoindole; indole; 3H-indole; indazole; 1H-Indazole; indoline; isoindoline; isobenzofuran; quinolizine; 4H-quinolizine; isoquinoline; quinoline; phthalazine; naphthyridine; quinoxaline; quinazoline; cinnoline; pteridine; isochroman; chroman; or chromene. In certain other embodiments, an end-group is xanthene; 4aH-carbazole; carbazole; carboline; phenanthridine; acridine; perimidine; phenanthroline; phenazine; or phenoxazine.

In certain other embodiments, the end-group is one of the above with substitution of one or more hydrogens at a ring (e.g., a 6-ring), for example, with substitution of 1, 2, 3, 4 or 5 hydrogens (up to the maximum number). In certain embodiments, multiple hydrogens are substituted with the same substituent, and in certain other embodiments, multiple hydrogens (e.g., 2, 3, 4, or 5) are substituted with different substituents (independently chosen substituents). In certain embodiments, a substitution of a hydrogen in an end-group with a six-ring may be in ortho-, meta-, and/or para-position. In certain other embodiments, substituents that may substitute for a hydrogen in an end-group may be one or more of the following: alkyl; $C_{1-2}$ alkyl; $C_{1-3}$ alkyl; $C_{1-4}$ alkyl; methyl; ethyl; propyl; an alkyl, $C_{1-2}$ alkyl, $C_{1-3}$ alkyl, $C_{1-4}$ alkyl, methyl, ethyl or propyl with one or more hydrogens (for example, 1, 2, 3, 4, 5, 6 or more hydrogens up to the maximum number) substituted with one or more of the substituents listed herein; a halide; fluorine; chlorine; bromine; iodine; mono-, di- and/or tri-halide (i.e., fluorine, chlorine, bromine and/or iodine) alkyl, $C_{1-2}$ alkyl, $C_{1-3}$ alkyl, $C_{1-4}$ alkyl, $C_{1-6}$ alkyl, $C_{1-10}$ alkyl, methyl, ethyl or propyl; tri-halide methyl; trifluoromethyl; trichloromethyl; tribromomethyl; triiodomethyl; hydroxyl; carboxyl; oxygen; amino; amide; dimethylamino; diethylamino; carboxamide; amino, amide, dimethylamino, diethylamino, carboxamide with one or more hydrogens (for example, 1, 2, 3, 4, 5, 6 or more hydrogens up to the maximum number) substituted with one or more of the substituents listed herein; methoxy; methylthio; mesyl; acetyl; acetylamino; allyl; ethoxy; tert-butyl; tert-butoxy; carbamoyl; formylamino; nitro; R, wherein R can be either the ortho, meta or para positions and can be H, OH, F, Cl, Br, I, $NO_2$, $NH_2$, $CF_jH_k$, $OCF_jH_k$, COOH, $CONH_2$; or CONR'R", where R' and R" are independently selected from H, methyl, ethyl, $CF_jH_k$, $C_2F_nH_m$, F, Cl, Br, I, CN, $CF_3$, $CCl_3$, $CBr_3$, $Cl_3$, $NO_2$, $COOCF_jH_k$, $(OPO_3)_2$—, $OCOCH_3$, $OCOCF_jH_k$, OMe, OEt, $OCF_jH_k$, $NH_2$, $NR_1R_2$ (where $R_1$ and $R_2$ may be H or alkyl groups); where j+k=3 and n+m=5, n or m may be 0.

As used herein, an "alkyl" refers to hydrocarbyl groups with one or more carbons and hydrogen bound to the carbon and which may be substituted. In a substituted alkyl, one or more (e.g., 2, 3, 4, 5, 6, 7, 8 or more) hydrogens are substituted with a substituent discussed herein. In a non-substituted alkyl, no hydrogen was substituted. In certain embodiments, a carbon may be substituted with N, O or S, and the N, O or S may be linked to a substituent discussed herein. Where more than one carbon is present, they are linked to each other to form a chain that may be straight and/or branched and the carbons may be linked together by one or more (e.g., 2, 3, 4 or 5) covalent single, double and/or triple bonds.

An end-group may be synthesized by any method known to those of skill in the art. Methods of synthesizing organic compounds that are useful in synthesizing an end-group are discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are incorporated herein by reference in their entirety.

5.1.2 Linkers of Tail Structures of the Invention

A linker of a trail structure of a tail-polyamide of the invention, in certain embodiments, connects an end-group to a polyamide. In certain embodiments, a linker may be an alkyl, a $C_{1-2}$ alkyl, a $C_{1-3}$ alkyl, a $C_{1-4}$ alkyl, a $C_{1-5}$ alkyl, a $C_{2-3}$ alkyl, a $C_{2-4}$ alkyl, a $C_{2-5}$ alkyl, a $C_{2-12}$ alkyl, a $C_{4-8}$ alkyl, a methyl, an ethyl, a propyl, a butyl, a pentyl, an amino alkyl, a bi-amino alkyl, a tri-amino alkyl, any of the alkyls listed here with one or more substitution of a hydrogen with a substituent listed above for end-groups. In certain other embodiments, any linker molecule maybe used to form a dimer, trimer, tetramer, or higher oligomer or polymer, to form a larger (e.g., longer) linker. Such dimers, trimers, tetramers, or higher oligormers or polymers, may be formed using one linker molecule (to form a homo-dimer, homo-trimer, homo-tetramer, etc.), or a mixture of more than one linker molecule (e.g., two, three, four, five, six or more different linker molecules) to form heterogenous linkers. In any dimer, trimer, tetramer, or higher oligomer or polymer linker, any linker molecule unit may be modified by substituting a hydrogen with a substituent listed above for end-groups. Different linker molecule units may be modified in the same way or in different ways.

A linker in certain embodiments maybe one of the following (with n=0 to 8):

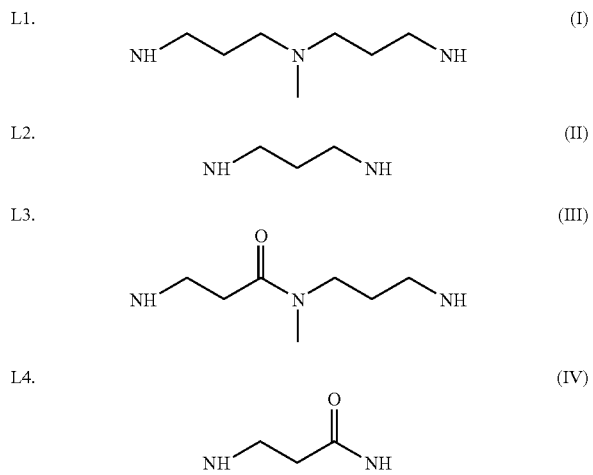

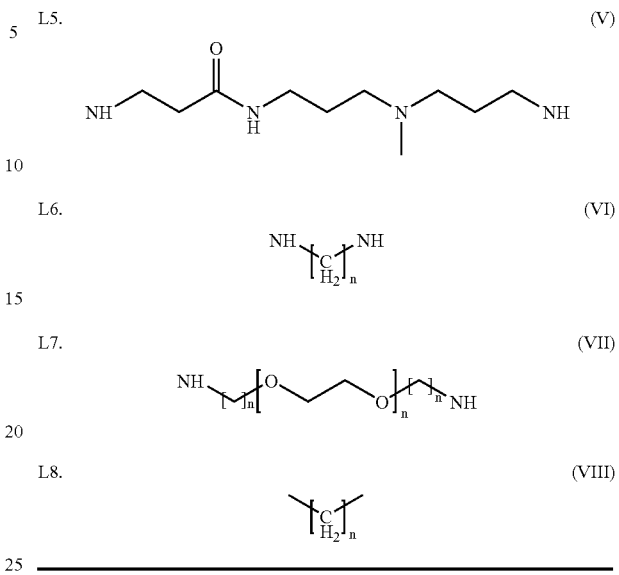

A linker may be synthesized by any method known to those of skill in the art. Methods of synthesizing organic compounds that are useful in synthesizing a linker are discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are incorporated herein by reference in their entirety.

5.1.3 Combinations of End-Groups and Linkers

An end-group of a tail-polyamide of the invention is preferably attached to a linker and the linker to the polyamide moiety. An end-group may be attached to a linker in any manner that secures or substantially secures the end-group to the linker during use of the tail-polyamide, for example, in cells or in an animal, a human, or a plant. In certain preferred embodiments, an end-group is attached to a linker through a covalent bond, for example, an ester bond, an amide bond, a polar covalent bond, a nonpolar covalent bond, a thiourea linkage, an oxime linkage, or any other type of covalent bond. In certain other embodiments, an end-group is attached to a linker in any manner that is of about equal strength to a covalent bond or at least about half as strong as a covalent bond, for example, an ionic bond, through complex formation, a hydrogen bond, or any other bond that is at least about half as strong as a covalent bond.

Examples of attaching an end-group to a linker through an amide bond are the following (wherein R and $R_1$ maybe any one, two or three substituents discussed for end-groups above and linked to the ring structure by covalent bond):

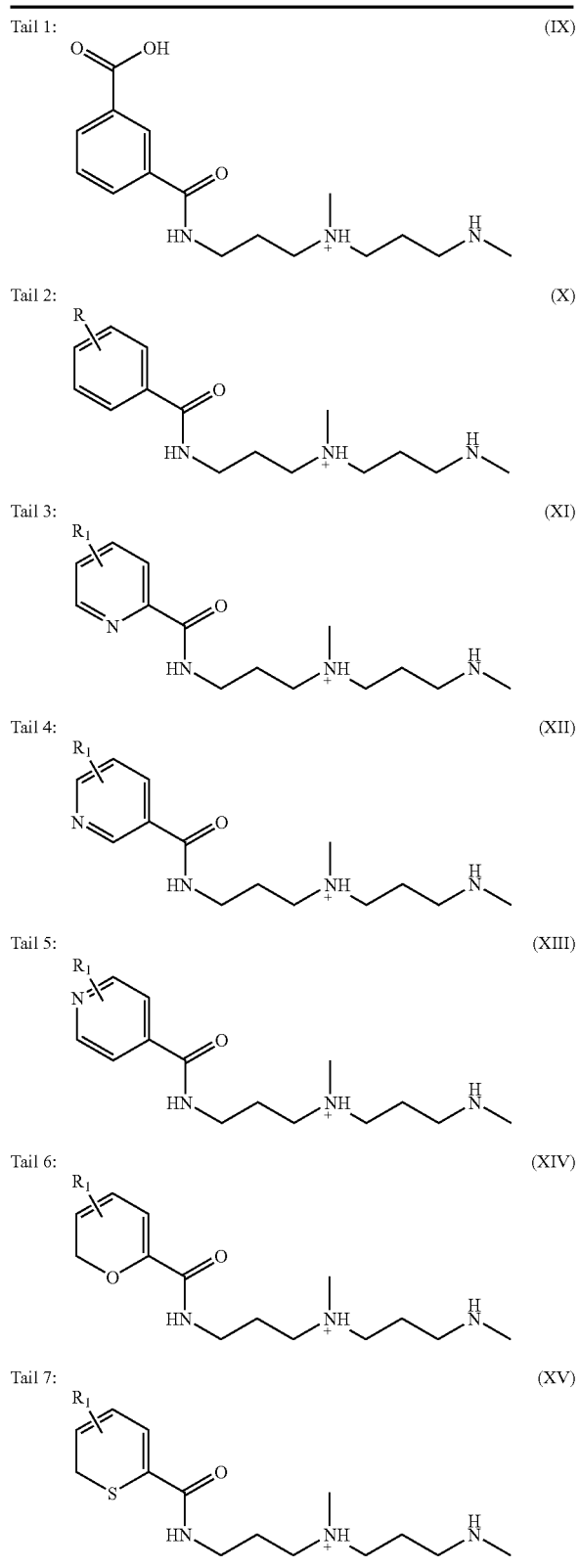

A molecule comprising an end-group and a linker may be synthesized by any method known to those of skill in the art. Methods of synthesizing organic compounds that are useful in synthesizing such a molecule are discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are incorporated herein by reference in their entirety.

5.2 Polyamide Moieties of Tail-Polyamides of the Invention

A tail-polyamide of the invention includes a polyamide moiety. A polyamide of a tail-polyamide does not contain a fluorescein moiety.

The term "polyamide" refers to polymers of linkable units chemically bound by amide (i.e., CONH) linkages; optionally, polyamides include chemical probes conjugated therewith. The term "linkable unit" refers to five-membered heterocycle, imidazoles, pyrroles, methylimidazoles, methylpyrroles, thiophene, fused six-membered cyclic monomer, and straight and branched chain aliphatic functionalities (e.g., methylene, ethylene, propylene, butylene, and the like) which optionally contain one or more nitrogen substituents, and chemical derivatives thereof. Linkable units of a polyamide of the invention may be linked, for example, by a linking element. The polyamides of tail-polyamides of the invention comprise methylimidazole carboxamides, methylpyrrole carboxamides, aliphatic amino acids, aliphatic desamino amino acids, aliphatic descarboxy amino acids. In certain embodiments, the polyamides of the invention comprise linkable units selected from the group consisting of Im, Py, β, and Dp, linked by amide bonds. Linkable units may be linked through a linking element. The term "Im" in a polyamide refers to 1-methyl-1H-imidazole, resulting for example from synthesis using 4-amino-1-methyl-1H-imidazole-2-carboxylic acid, or, in the case of N-terminal Im, 1-methyl-1H-imidazole-2-carboxylic acid, by methods well known in the art. The term "Py" refers to 1-methyl-1H-pyrrole, resulting for example from synthesis using 4-amino-1-methyl-1H-pyrrole-2-carboxylic acid, or, in the case of N-terminal Py, 1-methyl-1H-pyrrole-2-carboxylic acid. The term "β" refers to O-alanine (i.e., 3-aminopropanoic acid). The term "Dp" refers to dimethylaminopropylamine.

The term "chemical derivatives" refers to one or more independently chosen substitutions (e.g., 1, 2, 3, 4 or 5 substituents) with $R_p$ at any atom available to produce a stable compound, where $R_p$ can be halide, F, Cl, Br, I, OH, $CH_3$, $OCH_3$, COOH, N, NH, $NH_2$, $NH_3$, methyl monohalide, methyl bihalide, methyl trihalide, ethyl, ethoxy, propyl, propoxy, butyl, butoxy, CN, ethyl halide, ethyl bihalide, ethyltrihalide, S, O.

In certain embodiments, a polyamide of a tail-polyamide of the invention has the formula: —$X_1 X_2 \ldots X_m$-L-$X_{(m+1)} \ldots X_{(2m-1)} X_{2m}$—, wherein each $X_1$, $X_2$, $X_m$, $X_{(m+1)}$, $X_{(2m-1)}$, and $X_{2m}$ is independently a monomer element (or linkable unit), L is an optional linking element, and m falls in the range of 1 up to 10. In certain embodiments, a polyamide of the above formula includes binding pairs $X_1/X_{2m}$, $X_2/X_{(2m-1)}$, . . . , $X_m/X_{(m+1)}$. In certain other embodiments, a polyamide of the invention has the formula: —$(X_n$-$L_o)_p X_q$—, wherein n and q are independently chosen integers from 1 to 10, o is an independently chosen integer from 0 to 3, and p is an independently chosen integer from 1 to 3, and wherein X is a linkable unit that is independently chosen for each integer of n, p and q, and L is a linking element that is independently chosen for each o and p.

The phrase "linking element" refers to an optionally substituted aliphatic moiety comprising 2 to 12 carbon atoms which links, joins, attaches, or connects two oligomeric backbone chains, preferably of equal length. Representative linking elements which can be used in the present compounds include $C_{2-6}$-alkane and aliphatic amino acids (connecting the chains via the amino and carboxyl terminal ends). For instance, exemplary linkers include aminopropylene, —$CH_2CH_2CH_2$—, β-alanine, gamma-aminobutyric acid, or diaminobutyric acid (DAB). Preferred linkers include gamma-aminobutyric acid and diaminobutyric acid (e.g., R-2,4-diaminobutyric acid).

The phrase "five-membered heterocycle" refers to a cyclic ring of five atoms, wherein at least one atom of the ring is a heteroatom. The five-membered heterocycle can be aromatic or non-aromatic. An example of a five-membered heterocycle is

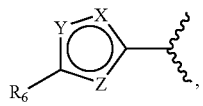

wherein each of X, Y and Z is independently —$CR_2$, N, —$NR_3$, O, or S and $R_6$, wherein $R_6$ is independently H, halogen, NO, N-acetyl, CHO, benzyl, $C_1$-$C_{12}$ alkyl, or a covalent bond; and wherein each of $R_2$ and $R_3$ is independently H, halogen, —OH, —OMe, —SH, —CN, —OAc, —$NH_2$, —NHAc, $C_1$-$C_6$ alkyl. For instance, representative five-membered heterocycles include N-methylpyrrole (Py), N-methyl imidazole (Im), 3-hydroxypyrrole (Hp), furan (Fr), 5-methylthiazole (Nt), 1-methyl-1H-pyrazole (Pz), 3-hydroxythiopene (Ht), pyrrole, triazole, thiophene, oxazole, and the like. Preferred five-membered heterocycles include N-methylpyrrole (Py), 1-methyl-1H-pyrazole (Pz), 1H-pyrrole (Nh), N-methyl imidazole (Im), 5-methylthiazole (Nt), furan (Fr), 3-hydroxypyrrole (Hp), 3-hydroxythiopene (Ht), 4-methylthiazole (Th), 3-methylthiophene (Tn), and thiophene (Tp).

Monomer elements contemplated for use in the practice of the present invention include optionally substituted pyrrole carboxamide monomer, optionally substituted imidazole carboxamide monomer, optionally substituted C—C linked heteromonocyclic/heterobicyclic moiety, and β-alanine. In the context of the present invention, the optionally substituted pyrrole carboxamide monomers have the structure:

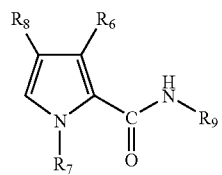

wherein: $R_6$ is selected from the group consisting of H, $CH_3$, $C_1$, $CF_3$, OH and $NH_2$; $R_7$ is selected from the group consisting of H, $C_{1-10}$ alkyl; $R_8$ is selected from the group consisting of hydrogen and a covalent bond; and $R_9$ is a covalent bond.

Further in the context of monomer elements of the present invention, optionally substituted imidazole carboxamide monomers have the structure:

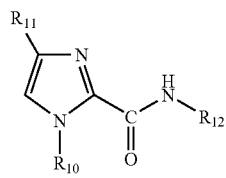

wherein: $R_{10}$ is selected from the group consisting of $C_{1-10}$ alkyl; $R_{11}$ is selected from the group consisting of hydrogen and a covalent bond; and $R_{12}$ is a covalent bond.

The phrase "fused six-membered cyclic monomer" or "fused six-membered ring" refers to a ring of six atoms which is fused to another ring structure. Preferably, at least one atom in either ring structure is a heteroatom. Fused six-membered rings include 6-5 ring systems wherein both rings are aromatic. An example of a fused six-membered ring is

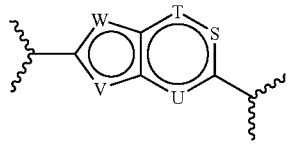

wherein each of S, T, and U is independently —$CR_1$ or N and each of V and W is independently —$CR_2$, N, —$NR_3$, O, or S, wherein each $R_1$ is independently H, halogen, —OH, —OMe, —OAc, —$NH_2$, —NHAc, —$CH_3$, —SH, —$NO_2$, —CHO, —$SO_2H$, —$S(O)NH_2$, —C≡C)$(CN)_3$, —CN, acetyl, $C_1$-$C_6$-alkyl; and each of $R_2$ and $R_3$ is independently H, halogen, —OH, —OMe, —SH, —CN, —OAc, —$NH_2$, —NHAc, $C_1$-$C_6$-alkyl. For instance, representative fused six-membered rings include benzimidazole (Bi), imidazo[4,5-b]pyridine (Ip), and hydroxybenzimidazole (Hz). Preferred fused six-membered cyclic monomers, include benzimidazole (Bi), imidazo[4,5-b]pyridine (Ip), and hydroxybenzimidazole (Hz), structures of which are shown below:

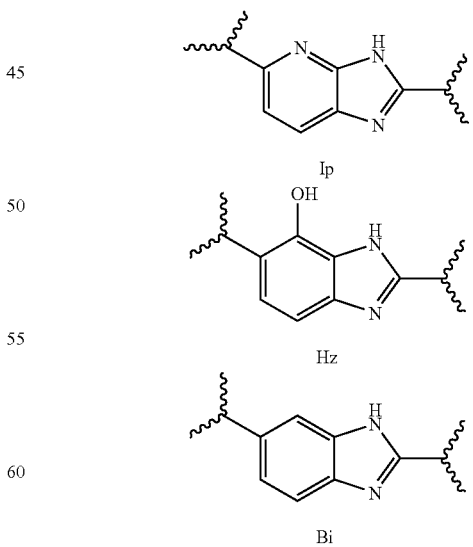

Further in the context of the present invention, optionally substituted C—C linked heteromonocyclic/heterobicyclic moieties have the structure

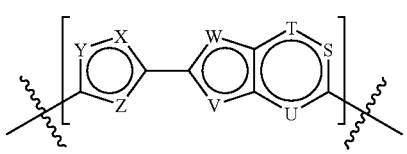

wherein: each of S, T, and U is independently —CR$_{13}$ or N; each of V, W, X, Y and Z is independently —CR$_{14}$, N, —NR$_{15}$, O, or S; and each R$_{13}$ is independently H, halogen, —OH, —OMe, —OAc, —NH$_2$, —NHAc, —CH$_3$, —SH, —NO$_2$, —CHO, —SO$_2$H, —S(O)NH$_2$, —(C═C)(CN)$_3$, —CN, acetyl, C$_{1-6}$ alkyl; and each of R$_{14}$ and R$_{15}$ is independently H, halogen, —OH, —OMe, —SH, —CN, —OAc, —NH$_2$, —NHAc, C$_{1-6}$ alkyl.

Each monomer element can be attached to another monomer element, first terminus, second terminus or optional linking element by a connectivity denoted as B, wherein B is independently

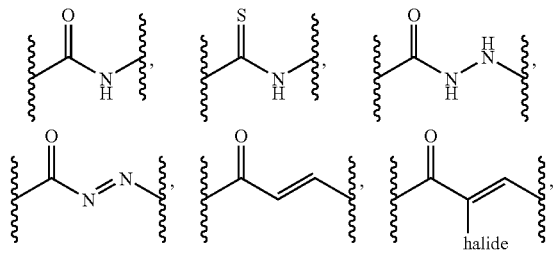

or a direct bond. The connectivity between each monomer element in the present backbone oligomers may be the same or different throughout the backbone oligomer. Preferable connectivity for monomer elements of the invention are the amide bond, —C(═O)NH—, which gives rise to polyamide backbone oligomers and the direct bond.

In certain embodiments, a polyamide of a tail-polyamide of the invention is a 6-ring polyamide, or a 7-ring, 8-ring, 9-ring, 10-ring, 11-ring, 12-ring, 13-ring, 14-ring, 15-ring, 16-ring, 17-ring, 18-ring, 19-ring, 20-ring, or higher ring polyamide. In certain preferred embodiments, a polyamide of a tail-polyamide of the invention is a (10-20)-ring polyamide.

In the nomenclature of polyamides, the sequence of constituent linkable units is recited, wherein the connecting linkage is an amide linkage. For example, the term "ImPyDp" refers to the chemical structure N-(5-(3-(dimethylamino)propylcarbamoyl)-1-methyl-1H-pyrrol-3-yl)-1-methyl-1-1H-imidazole-2-carboxamide. By analogy to a peptide, the Im linkable unit of "ImPyDp" is considered to reside at the "N-terminal" of the polyamide, whereas the Dp occupies the "C-terminal" position.

In certain embodiments, a polyamide of the current invention has a motif referred to as a "hairpins," "H-pins," "overlapped," "slipped," "cyclic," "tandem," and/or "extended" polyamide motifs. Specifically, hairpin polyamides are those wherein the carboxy terminus of one amino acid polymer is linked via a linker molecule, typically aminobutyric acid or a derivative thereof to the amino terminus of the second polymer portion of the polyamide. Indeed, the linker amino acid γ-aminobutyric acid (γ), when used to connect first and second polyamide polymer portions, or polyamide subunits, C→N in a "hairpin motif," enables construction of polyamides that bind to predetermined target sites in dsDNA with more than 100-fold enhanced affinity relative to unlinked polyamide subunits. (See, for example, Turner, et al. (1997), J. Am. Chem. Soc., 119: 7636-7644; Trauger, et al. (1997), Angew. Chemie. Int. Ed. Eng., 37:1421-1423; Turner, et al. (1998), J. Am. Chem. Soc., 120: 6219-6226; and Trauger et al. (1998), J. Am. Chem. Soc., 120:3534-3535). Paired β-alanine residues (β/β), restore the curvature of the dimer for recognition of larger binding sites and in addition, code for AT/TA base pairs. (Trauger, J. W., Baird, E. E., Mrksich, M. & Dervan, P. B. (1996), J. Am. Chem. Soc. 118, 6160-6166; Swalley, S. E., Baird, E. E. & Dervan, P. B. (1997), Chem.-Eur. J. 3, 1600-1607; and Trauger, J. W., Baird, E. E. & Dervan, P. B. (1998), J. Am. Chem. Soc. 120, 3534-3535. Eight ring hairpin polyamides can bind a 6 base pair match sequence at subnanomolar concentrations with good sensitivity to mismatch sequences. Dervan, P. B. et al. (1999), Curr. Opin. Chem. Biol. 3: 688-693. Moreover, eight-ring hairpin polyamides (comprised of two four amino acid polymer portions linked C→N) have been found to regulate transcription and permeate a variety of cell types in culture (See Gottesfield, J. M. et al. (1997), Nature, 387:202-205 (1997).

An H-pin polyamide motif, i.e., wherein two paired, antiparallel polyamide subunits are linked by a linker covalently attached to an internal polyamide pair, have also been reported. Another polyamide motif that can be formed between linked or unlinked polyamide subunits is an "extended" motif, wherein one of the polyamide subunits comprises more amino acids than the other, and thus has a single-stranded region. See U.S. Ser. No. 08/607,078. In contrast, an "overlapped" polyamide is one wherein the antiparallel polyamide subunits completely overlap, whereas in a "slipped" binding motif, the two subunits overlap only partially, with the C-terminal portions not associating with the N-terminal regions of the other subunit. See U.S. Ser. No. 08/607,078.

Hairpin polyamide-dye conjugates enter the nucleus of cultured SW620 cancer cells and other cell lines in culture. (Best et al. (2003) Proc. Natl. Acad. Sci. USA 100, 12063-68). Polyamide-chlorambucil conjugates blocked transcription by mammalian RNA polymerase II when the conjugates were targeted to the coding regions of genes, both in vitro and in cell culture, similar to the results reported for polyamide-duocarmycin conjugates. (Shinohara K et al. (2003) J. Am. Chem. Soc.; Oyoshi T et al., (2003) J Am Chem Soc 125, 4752-4). Polyamides, such as PI-polyamides, which are useful alone, or as conjugates, can be prepared as described (see U.S. Pat. No. 6,559,125, which is incorporated herein by reference).

Polyamides that form hairpin turns bind to predetermined sequences in the minor groove of DNA with affinities and specificities comparable to naturally occurring DNA binding proteins (Trauger et al., Id.; Swalley et al., 1997, J. Am. Chem. Soc. 119:6953-6961; Turner et al., 1997, J. Am. Chem. Soc. 119:7636-7644). Sequence specificity is determined by a code of oriented side-by-side pairings of the polyamides (Wade et al., 1992, J. Am. Chem. Soc. 114, 8783-8794; Mrksich et al., 1992, Proc. Natl. Acad. Sci. U.S.A. 89:7586-7590; Wade et al., 1993, Biochemistry 32, 11385-11389; Mrksich et al., 1993, J. Am. Chem. Soc. 115:2572-2576; White et al., 1997a, Chem. Biol. 4:569-578; White et al., 1997b, J. Am. Chem. Soc. 119:8756-8765). An Im/Py pairing targets a G-C base pair, while a Py/Im pair recognizes C0G. The Py/Py pair is degenerate and targets both AFT and T-A base pairs (Pelton et al., 1989, Proc. Natl. Acad. Sci. USA 86:5723-5727; Chen et al., 1994, Nature Struct. Biol. 1:169-175; White et al., 1996, Biochemistry 35:12532-12537). The validity of these pairing rules is supported by a variety of polyamide structural motifs which have been characterized by footprinting, affinity cleaving, 2-D NMR, and x-ray methods. As well known in the art, the term "footprinting" refers to a technique for identifying the site on DNA bound by some agent (i.e., protein or polyamide) by virtue of the protection of backbone phosphate DNA bonds against attack by nuclease, or to protection against chemical modification of the DNA bases, afforded by the agent.

The phrase "hairpin oligomer backbone" refers to two chains of monomer elements that are linked to each other by a covalent linking element. In a hairpin oligomer backbone, the linker which covalently links the two chains imparts an overall U-turn shape to the oligomer backbone. Hairpin oligomers are well known in the art and are described, for example, in Church et al., Biochemistry 29: 6827, 1990, and He et al., JACS 115: 7061, 1993.

Polyamides may also be linked in tandem. In certain embodiments, a unit of a first polyamide is linked to a second polyamide, for example, through an amino acid linking group such as β-alanine or 5-aminovaleric acid bound to a residue (e.g., gamma residue) of a first polyamide and to the carboxy-tail of a second polyamide. As such, two or more polyamides may be linked, forming a tandemly-linked polyamide. Such a polyamide is said to be tandemly-linked or a tandem-linked polyamide.

Rules for the recognition of linear polyamide:DNA complexes have been reported (Urbach & Dervan, supra). These rules indicate that an Im linkable unit within a linear polyamide favors all four Watson-Crick duplex DNA basepairs (i.e., A•T, T•A, G•C and C•G), whereas β-alanine and Py favor A•T and T•A basepairs. Without wishing to be bound by theory, given the high affinity of polyamides for their target sites as characterized by dissociation constants of nanomolar to picomolar (Dervan, 2001, Bioorgan. Med. Chem. 9:2215-2235; White et al., 1998, Nature (London) 391:468-471; Turner et al., 1998, J. Am. Chem. Soc. 120:6219-6226), linear β-alanine linked polyamides can be envisaged to act as a thermodynamic "sink" and lock expanded oligonucleotide repeat sequences into a duplex B-type DNA conformation. Such a binding event disfavors duplex unpairing, which is necessary for formation of, for example, triplex and sticky DNA. Alternatively, polyamides may relieve heterochromatin-mediated repression by opening the chromatin domain containing the target gene (e.g., frataxin gene) (Janssen et al., 2000b, Mol. Cell 6:101301924). Importantly, polyamides bound within coding regions of genes do not necessarily block transcriptional elongation (Gottesfeld et al., 2002, J. Mol. Biol. 121:249-263; Shinohara et al., 2004, J. Am. Chem. Soc. 126:5113-5118; Dickinson et al., 2004, Chem. Biol. 11:1583-1594). Thus, polyamides have the potential to relieve transcription repression at expanded oligonucleotide repeat sequences.

Methods for designing a polyamide that selectively binds to a DNA sequence of interest, and specific polyamides that specifically bind to certain DNA sequences, are discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are incorporated herein by reference in their entirety.

In general, polyamides of the present invention may be synthesized by solid phase methods using compounds such as Boc-protected 3-methoxypyrrole, imidazole, pyrrole aromatic amino acids, and alkylated derivatives thereof, which are cleaved from the support by aminolysis, deprotected (e.g., with sodium thiophenoxide), and purified by reverse-phase HPLC, as well known in the art. The identity and purity of the polyamides may be verified using any of a variety of analytical techniques available to one skilled in the art such as $^1$H-NMR, analytical HPLC, and/or matrix-assisted laser-desorption ionization time-of-flight mass spectrometry (MALDI-TOF MS-monoisotropic). A tail-polyamide of the invention, in certain embodiments, may also comprise a protective group useful for purposes of polyamide synthesis, in certain other embodiments, a tail-polyamide does not comprise a protective group. Useful protective groups are known to those of skill in the art.

The aliphatic functionalities of linkable units can be provided, for example, by condensation of β-alanine or dimethylaminopropylamine during synthesis of the polyamide by methods well known in the art. Linkable units are typically supplied as amino acids, desamino acids, or descarboxy amino acids prior to amide bond formation by condensation methods well known in the art to form linking amide groups. The term "amino acid" refers to an organic molecule containing both an amino group ($NH_2$) and a carboxylic acid (COOH). The term "desamino" refers to an amino acid from which the amino functionality has been removed. The term "descarboxy" refers to an amino acid from which the carboxylic acid functionality has been removed. The term "chemical probe" refers to chemical functionalities having properties that facilitate location and identification of polyamides functionalized (i.e., covalently bonded) by such chemical probes. A chemical probe does not include fluorescein. Methods of conjugating chemical probes to polyamides of the invention are well known in the art.

Methods for the synthesis of polyamides, including protective groups, and polyamide structures, motifs and modifications, are further discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are incorporated herein by reference in their entirety.

5.3 Tail-Polyamides of the Current Invention

A tail-polyamide of the invention comprises a polyamide, a linker and an end-group. In certain embodiments, in a tail-polyamide of the invention, an end-group is attached to a linker and the linker is attached to a polyamide. Any end-group, linker and polyamide may be combined to result in a tail-polyamide of the invention. In certain embodiments, a linker of a tail-polyamide of the invention is attached to a polyamide at the C-terminus of the polyamide, at the C-terminal unit of the polyamide, at the N-terminus of the polyamide, at the N-terminal unit of the polyamide, or at the turn region of a hairpin polyamide. In certain embodiments, a tail-polyamide of the current invention has one or more (e.g., 2, 3, 4, 5 or more) hairpins, H-pins, overlaps, slips, cyclical motifs, tandem motifs, and/or extended polyamide motifs.

Tail-polyamides may be synthesized by any method known in the art, including methods discussed herein. Methods of synthesizing organic compounds that are useful in synthesizing a tail-polyamide of the invention are discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos.

20060270727; 20060025429; 20060019972; 20060014163; 20050026174, and in references discussed in any one of these patents and patent applications. All of these patents and patent applications, and references discussed therein, are incorporated herein by reference in their entirety.

A tail-polyamides of the present invention is capable of binding double stranded (i.e., duplex) DNA at a specific sequence (i.e., the target DNA sequence or target sequence or target site) with high affinity and selectivity. A recitation of a sequence of DNA herein contemplates the recited single-stranded DNA, the complementary (i.e., Watson-Crick) sequence, and the duplex molecule comprising the recited and complementary strands of DNA.

As used herein, "subnanomolar affinity" means binding that is characterized by a dissociation constant, $K_d$, of less than 1 nM, as measured by DNase I footprint titration. In certain preferred embodiments, a tail-polyamide of the present invention is characterized by subnanomolar binding affinity for the target DNA sequence for said tail-polyamide. As used herein, the "selectivity" of the binding of a tail-polyamide or polyamide to a DNA sequence is the ratio of the dissociation constant, $K_d$, as measured by DNase I footprint titration, when binding the tail-polyamide or polyamide to a mismatch DNA sequence divided by the corresponding dissociation constant when binding the tail-polyamide or polyamide to the target DNA sequence. In certain preferred embodiments, tail-polyamides of the present invention are characterized by a selectivity of about 5 or greater, more preferably a selectivity of greater that about 10.

In certain preferred embodiments, a tail-polyamide of the invention has at least 20-fold (more preferably about 100-fold) greater affinity for a target site than for a site differing from the target site by two amino acids. Preferably, a conjugate will interact with its target nucleotide base pair sequence with an affinity, as measured by DNase footprint titration, of less than about 100 nM, preferably less than about 10 nM, more preferably less than about 1.0 nM, even more preferably less than about 0.1 nM. Thus, the conjugates of the invention have substantially the same binding affinity and specificity as the polyamide.

In certain embodiments, a tail-polyamide of the invention has a binding affinity $K_a$ for its target site that is greater than $5 \times 10^8$ M$^{-1}$, preferably greater than $10^9$ M$^{-1}$, more preferably greater than $10^{10}$ M$^{-1}$. The reduction in affinity of a tail-polyamide of the invention to a site with a single mismatch when compared to its target site, in certain embodiments, is at least 3 fold, at least 5 fold, at least 10 fold, at least 20 fold, or at least 100 fold or more.

The affinity of a tail-polynucleotide of the invention can be determined by any method known in the art and as discussed herein.

Methods for the synthesis of polyamides are further discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are incorporated herein by reference in their entirety.

A tail-polyamide of the invention, in certain embodiments, can be examined to determine its affinity for its target DNA sequence and at mismatched and random sites, if desired. The affinity can be determined using DNase footprint analysis, as discussed herein. A tail-polyamide of the invention, in certain embodiments, can also be examined to determine its ability to modulate gene expression, for example, by using the hypoxia response element or another DNA sequence element known to be involved in regulating the expression of a gene. For example, a tail-polyamide may be administered to cells in culture at varying concentrations (e.g., at 0.2 µM, 0.5 µM, 1 µM, 2 µM, 5 µM, 10 µM, and 25 µM) and the expression of a gene that depends on the target site for the tail-polyamide may be determined by measuring levels of mRNA (messenger RNA) compared to mRNA levels in the absence of the tail-polyamide. The analysis may be carried out, for example, as discussed in the examples below. An analysis of a tail-polyamide's ability to modulate gene expression may be carried out in different cell types, for example, as described in Edelson et al., 2004, Nucleic Acids Res. 32:2802-2818. Other methods to analyze a polyamide's ability to modulate gene expression include the use of luciferase, protein quantitation, observing morphological and/or phenotypic changes, which are known to those of skill in the art.

Methods for the analysis of polyamides' ability to bind DNA and to modulate gene expression are further discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are incorporated herein by reference in their entirety.

5.4 Tail-Polyamides of the Current Invention as Research Tools

A tail-polyamide of the invention, in certain embodiments, may be used as a research tool. For example, a tail-polyamide of the invention may be used to modulate the expression of genes involved in a disease in cell culture or in an animal, for example, by down-regulating a gene so that the cells or the animal exhibits one or more traits of the disease. Following such modulation, a drug candidate may be tested in the cell culture and/or the animal to determine if the drug candidate is capable of compensating for the effects of gene modulation.

In certain other embodiments, a tail-polyamide may be used to test the effectiveness of analytical techniques in a cell and/or an animal, for example by modulating gene expression and by testing the technique's ability to detect the effects thereof.

5.5 Therapeutic Applications of Tail-Polyamides of the Current Invention

A tail-polyamide of the current invention, in certain embodiments, may be used in the treatment or prevention of disease in humans, animals and/or plants. It is contemplated that these compounds may be used independently or in conjunction with inactive excipients or active ingredients. As used herein, the term "agent" refers to compounds of the invention or compositions thereof comprising active and/or inactive ingredients.

In certain embodiments, tail-polyamides of the invention may be used to modulate the expression of a variety of target genes, including any gene which is implicated in the manifestation or propagation of a disease state. For instance, expression of viral genes may be inhibited using DNA-binding polymers of the invention. Exemplary viral genes include HIV, HTLV, HPV, and HSV related genes. A tail-polyamide of the invention, in certain embodiments, may be used to decrease the expression of an oncogene. Aberrant expression of various oncogenes has been implicated in the manifestation of abnormal cellular proliferation. Representative oncogenes which expression may be modulated by a tail-polyamide of the invention include v-sis, int 2, KS3, HST, int-, EGFR, v-fms, v-kit, v-ros, MET, TRK, NEU, RET, sea, Dbl, Ost, Tiam-1, Vav, Lbc, H-RAS, K-RAS, N-RAS, gsp, gip, v-crk, SRC, v-yes, v-fgr, v-fps, v-fes, BCR/ABL, ros, v-mos, v-raf, pim-1, cot (ser/thr), v-myc, N-MYC, L-MYC, v-myb, v-fos, v-jun, v-ski, v-rel, v-ets, and v-erbA. Accordingly, tail-polyamides of the instant invention may be administered to a subject for the treatment or amelioration of cancer. "Treating" as used herein refers to alleviation of at least one symptom associated with cancer, or halt of further progression or worsening of such symptom, or prevention or prophylaxis of cancer.

A tail-polyamide of the invention, in certain embodiments, may delivered to a patient in any way known in the art. The particular delivery mode selected will depend upon the particular tail-polyamide selected, the condition being treated, the severity of the condition, whether the treatment is therapeutic or prophylactic, and the dosage required for efficacy. Therapeutic delivery of tail-polyamides of the invention may be practiced using any mode of administration that is medically acceptable, meaning any mode that produces effective levels of the active compounds without causing clinically unacceptable adverse effects. Any dosage forms containing effective amounts are well within the bounds of routine experimentation and therefore, well within the scope of the instant invention. A therapeutically effective dose may vary depending upon the route of administration and dosage form. The administration may, for example, be oral, intraperitoneal, intra-cavity such as rectal or vaginal, transdermal, topical, nasal, inhalation, mucosal, interdermal, or parenteral routes. The term "parenteral" includes subcutaneous, intravenous, intramuscular, or infusion. Intravenous or intramuscular routes may not be particularly suitable for long term therapy and prophylaxis. In certain embodiments, however, it may be appropriate to administer the agent in a continuous infusion every several days, or once a week, or every several weeks, or once a month. Intravenous or intramuscular routes may be preferred in emergency situations. Oral administration may be used for prophylactic treatment because of the convenience to the patient as well as the dosing schedule. Likewise, sustained release devices as described herein may be useful in certain embodiments for prophylactic or post surgery treatment, for example.

Direct administration of a tail-polyamide of the present invention to a designated site may be preferred for some methods provided herein. For example, treatment with a tail-polyamide via topical administration in and around affected areas may be performed. In still other embodiments, a tail-polyamide may be delivered by injection directly into the tissue with, for example, a biopsy needle and syringe.

Systemic administration may be preferred in some instances such as, for example, if the subject is known to have or is suspected of having metastases. In this embodiment, all tumor sites, whether primary or secondary, may receive the tail-polyamide. Systemic delivery may be accomplished through for example, oral or parenteral administration. Inhalation may be used in either systemic or local delivery, as described below.

A tail-polyamide of the invention, in certain embodiments, is administered in therapeutically effective amounts. A therapeutically effective amount is an amount sufficient to delay the onset of, inhibit the progression of, or halt altogether the particular condition being treated. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. A therapeutically effective dose results in amelioration of at least one undesirable symptom. It is preferred generally that a maximum dose be used, that is, the highest safe dose according to sound medical judgment.

Dosing amounts, dosing schedules, routes of administration and the like can be selected so as to affect bio-activity of the present compounds. Such determinations are routine and well known to one of ordinary skill in the art.

A therapeutically effective amount typically varies from 0.01 mg/kg (weight of tail-polyamide over weight of patient) to about 1000 mg/kg, preferably from about 0.1 mg/kg to about 200 mg/kg, and most preferably from about 0.2 mg/kg to about 20 mg/kg, in one or more dose administrations daily, for one or more days. In some embodiments, a tail-polyamide is administered for more than 7 days, more than 10 days, more than 14 days, or more than 20 days. In still other embodiments, a tail-polyamide is administered over a period of weeks, or months. In still other embodiments, a tail-polyamide is delivered on alternate days. For example, the tail-polyamide is delivered every two days, or every three days, or every four days, or every five days, or every six days, or every week, or every month.

A tail-polyamide of the invention, in certain embodiments, is administered in prophylactically effective amounts. In these embodiments, a tail-polyamide is administered in an amount effective to prevent the development of an abnormal or undesirable condition or disease. For example, in connection with methods directed towards treating subjects having a condition characterized by abnormal mammalian cell proliferation, an effective amount to inhibit proliferation would be an amount sufficient to reduce or halt altogether the abnormal mammalian cell proliferation so as to slow or halt the development of or the progression of a cell mass such as, for example, a tumor. As used in the embodiments, "inhibit" embraces all of the foregoing.

For example, in connection with methods directed to inhibition of mammalian cell proliferation, a therapeutically effective amount will be an amount necessary to extend the dormancy of micrometastases or to stabilize any residual primary tumor cells following surgical or drug therapy.

Compositions presented herein may include DNA-binding polymers of the invention in combination with any standard physiologically and/or pharmaceutically acceptable carrier known in the art. The term "pharmaceutically acceptable carrier" as used herein means one or more compatible solid or liquid fillers, diluents or encapsulating substances which are suitable for administration to a subject. The term "carrier" denotes an organic or inorganic ingredient, natural or synthetic, which with the DNA-binding polymer is combined to facilitate delivery of the composition. The components of the pharmaceutical compositions also are capable of being co-mingled with the molecules of the present invention, and with each other, in a manner so as to not substantially impair the desired pharmaceutical efficacy. Pharmaceutically acceptable further means a non-toxic material that is compatible with a biological system such as a cell, cell culture, tissue, or organism. The particular carrier may vary depending on the route of therapeutic delivery.

Pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by intranasal administration, by transmucosal administration, by rectal administration, or subcutaneous administration as well as intrathecal, intravenous, intramuscular, intraperitoneal, intranasal, intraocular or intraventricular injection. The compound or DNA-binding polymers of the instant invention can also be administered in a local rather than a systemic fashion, such as injection as a sustained release formulation. The following dosage forms are given by way of example and should not be construed as limiting the instant invention.

Compositions suitable for parenteral administration conveniently comprise a sterile aqueous preparation of the agent, which is preferably isotonic with the blood of the recipient. This aqueous preparation may be formulated according to known methods using suitable dispersing or wetting compounds and suspending compounds. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found, for example, in "Remington's Pharmaceutical Sciences" Mack Publishing Co., New Jersey (1991), which is incorporated herein by reference.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating compounds, and inert gases and the like. The pharmaceutical compositions may conveniently be presented in unit dosage form and may be prepared by any of the methods well-known in the art of pharmacy.

Compositions suitable for oral administration may be presented as discrete units, such as capsules, tablets, lozenges, each containing a predetermined amount of the agent. Other compositions include suspensions in aqueous liquids or non-aqueous liquids such as a syrup, elixir or an emulsion. Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

Compositions may comprise a biocompatible microparticle or implant that is suitable for implantation. Biocompatible and biodegradable polymeric matrix materials may also be added. The polymeric matrix may be used to achieve sustained release of the agent in a subject. DNA-binding polymers of the invention may be encapsulated or dispersed within a biocompatible and biodegradable polymeric matrix. The polymeric matrix can be in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular or pulmonary surface. The matrix composition also can be selected not to degrade, but rather, to release by diffusion over an extended period of time.

Both non-biodegradable and biodegradable polymeric matrices can be used to deliver the agents of the invention to the subject. Such polymers may be natural or synthetic polymers. Synthetic polymers are preferred. The polymer is selected based on the period of time over which release is desired, generally in the order of a few hours to a year or longer. The polymer optionally is in the form of a hydrogel that can absorb up to about 90% of its weight in water and further, optionally is cross-linked with multi-valent ions or other polymers.

Exemplary synthetic polymers which can be used include: polycarbonates, polyalkylenes, polyalkylene glycols, polyalkylene oxides, polyalkylene terpthalates, poly-vinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone. Examples of non-biodegradable polymers include ethylene vinyl acetate, poly(meth)acrylic acid, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers may also be included in the present compositions. Examples of such bioadhesive polymers include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Compositions of the present invention may be formulated as timed release, delayed release, or sustained release delivery systems. Such systems can avoid the need for repeated administrations of the agent of the invention, increasing convenience to the subject and the physician. Many types of release delivery systems are available and known to those of ordinary skill in the art. They include the above-described polymeric systems, as well as polymer base systems such as poly(lactide-glycolide), polyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,675,189 and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be used in the treatment of chronic conditions, such as the suspected presence of dormant metastases. Long-term release, are used herein, means that the implant is constructed and arranged to deliver therapeutic levels of the active ingredient for at least 30 days, at least 60 days and more preferably for several months. Long-term sustained release implants are well-known to those of ordinary skill in the art and include some of the release systems described above.

For oral, buccal, and sublingual administration, powders, suspensions, granules, tablets, pills, capsules, gelcaps, and caplets are acceptable as solid dosage forms. These can be prepared, for example, by mixing one or more DNA-binding polymers of the instant invention, or pharmaceutically acceptable salts or tautomers thereof, with at least one additive or excipient such as a starch or other additive. Suitable additives or excipients are sucrose, lactose, cellulose, sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethylcellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents, or perfuming agents. Additionally, dyestuffs or pigments may be added for identification. Tablets and pills may be further treated with suitable coating materials known in the art.

As noted above, suspensions may include oils. Such oils include, but are not limited to, peanut oil, sesame oil, cottonseed oil, corn oil and olive oil. Suspension preparations may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For intranasal administration (e.g., to deliver compounds to the brain), or administration by inhalation (e.g., to deliver compounds through the lungs), the pharmaceutical formulations may be a solution, a spray, a dry powder, or aerosol containing any appropriate solvents and optionally other compounds such as, but not limited to, stabilizers, antimicrobial agents, antioxidants, pH modifiers, surfactants, bioavailability modifiers and combinations of these. Examples of intranasal formulations and methods of administration can be found in WO 01/41782, WO 00133813, WO 91/97947, U.S. Pat. Nos. 6,180,603, and 5,624,898. A propellant for an aerosol formulation may include compressed air, nitrogen, carbon dioxide, or a hydrocarbon based low boiling solvent. The compound or DNA-binding polymers of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or diluents include sterilized water, Ringer's solution, or an isotonic aqueous saline solution. For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more DNA-binding polymers of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

Compositions of the present invention embrace pharmaceutically acceptable salts of DNA-binding polymers of the invention. Pharmaceutically acceptable salts include a salt with an inorganic base, organic base, inorganic acid, organic acid, or basic or acidic amino acid. As salts of inorganic bases, the invention includes, for example, salts of alkali metals (such as sodium or potassium) and alkaline earth metals (such as calcium and magnesium or aluminum, and ammonia). As salts of organic bases, the invention includes, for example, salts of trimethylamine, triethylamine, pyridine, picoline, ethanolamine, diethanolamine, triethanolamine. As salts of inorganic acids, the instant invention includes, for example, salts of hydrochloric acid, hydroboric acid, nitric acid, sulfuric acid, and phosphoric acid. As salts of organic acids, the instant invention includes, for example, salts of formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid.

The present invention is further illustrated by the following examples, which are not intended to be limiting in any way whatsoever.

EXAMPLES

Example 1

Improved Nuclear Localization of DNA-Binding Polyamides 1.1 Abstract

Regulation of endogenous genes by DNA-binding polyamides requires effective nuclear localization. Previous work employing confocal microscopy to study uptake of fluorophore-labeled polyamides has demonstrated the difficulty of predicting a priori the nuclear uptake of a given polyamide. The data suggest that dye identity influences uptake sufficiently such that a dye-conjugate cannot be used as a proxy for unlabeled analogs. Polyamides capable of nuclear localization unaided by fluorescent dyes are desirable due to size and other limitations of fluorophores. Recently, a polyamide-fluorescein conjugate targeted to the hypoxia response element (HRE) was found to inhibit vascular endothelial growth factor (VEGF) expression in cultured HeLa cells. The current study used inhibition of VEGF expression as a biological read-out for effective nuclear localization of HRE-targeted polyamides. We synthesized a focused library of non-fluorescent, HRE-targeted polyamides in which the C-terminus 'tail' has been systematically varied. Members of this library were found to bind the HRE with affinities comparable or superior to that of the fluorescein-labeled analog. Although most library members demonstrate modest or no biological activity, two non-fluorescent polyamides are reported with activity rivaling that of the previously reported fluorescein-labeled polyamide. We also obtained data showing that promoter occupancy by HIF-1, the transcription factor that binds the HRE, is inhibited by HRE-targeted polyamides.

1.2 Introduction

Polyamides containing N-methylimidazole (Im) and N-methylpyrrole (Py) comprise a class of programmable DNA-binding ligands capable of binding to a broad repertoire of DNA sequences with affinities and specificities comparable to those of natural DNA-binding proteins (1, 2). Sequence specificity is programmed by side-by-side pairings of the heterocyclic amino acids in the minor groove of DNA: Im/Py distinguishes G●C from C●G; Py/Py binds both A●T and T●A; and 3-chlorothiophene/N-methylpyrrole (Ct/Py) prefers T●A over A●T at the N-terminus position (3-5). The use of polyamides to modulate the expression of selected genes through interaction with transcriptional machinery could have applications in biology and human medicine (1, 2). Regulation of endogenous genes by DNA-binding small molecules requires cellular uptake and nuclear localization (6-9), chromatin accessibility (10, 11) and site-specific interactions with gene promoters sufficient to interfere with specific transcription factor-DNA interfaces (12-15).

The use of confocal microscopy to visualize subcellular localization of fluorophore-labeled molecules is a convenient method to study uptake and trafficking of polyamides in living cells (6-9). Nuclear localization of more than 100 hairpin polyamide-fluorophore conjugates in several human cell lines has been examined using this method (8, 9). Py/Im content, number and location of positive and negative charges, presence of a β-alanine residue at the C-terminus, choice of fluorophore, linker composition and attachment point have been shown to influence nuclear localization of polyamide-fluorophore conjugates (8, 9). Although a significant number of eight-ring hairpin-polyamides with fluorescein at the C-terminus were shown to have good nuclear uptake in 10 cell lines, this complexity makes it difficult to predict a priori the subcellular distribution of a particular polyamide-fluorophore conjugate. Efficient nuclear localization of a fluorophore conjugate is not necessarily predictive for non-fluorescent analogs. Screening polyamides for a biological effect dependent on nuclear localization is a viable approach for the assessment of nuclear uptake and does not require incorporation of an optical tag. As polyamides are studied in model systems of greater biological complexity, molecules that can access the nuclei of cells without the use of fluorescent dyes are desirable.

Polyamide-fluorescein conjugate 1 (FIG. 1) was designed to bind the sequence 5'-ATACGT-3' within the hypoxia response element (HRE) in the vascular endothelial growth factor (VEGF) enhancer. It was found to bind its target site with an affinity of $6.3 \times 10^9$ M$^{-1}$, disrupt hypoxia-inducible factor 1 (HIF-1) binding to the HRE in vitro, enter the nuclei of HeLa cells, and inhibit hypoxia-induced VEGF mRNA and protein production in cultured HeLa cells (FIG. 2A-C) (16). A control polyamide 2 designed to bind the DNA sequence 5'-WGGWCW-3' (where W denotes an A or T) also exhibited nuclear localization, but had a modest effect on VEGF expression. Independently, the DNA-binding antibiotic echinomycin, which binds 5'-ACGT-3', was found to inhibit VEGF expression in U251 cells (17, 18). The finding that two molecules of different structure bind the same HRE sequence 5'-TACGT-3' and exhibit similar biological effects on hypoxia-driven gene expression validates the concept of using small molecules to interfere with protein-DNA interfaces.

The current study utilizes the inhibition of hypoxia-induced VEGF expression as a biological read-out for nuclear localization of polyamides targeted to the HRE. As a control, we show that a polyamide-fluorescein conjugate 3 that targets the HRE but exhibits poor nuclear localization in HeLa cells due to a non-optimal linker (8) has a limited effect on hypoxia-induced VEGF expression. We synthesized a focused library of polyamides with an identical core sequence that targets the HRE while varying C-terminus tail moieties. The C-terminus was chosen as the site of chemical variation in our library, as subtle modifications to this area were previously found to influence nuclear localization of polyamide-fluorophore conjugates (8, 9). The polyamides generated in this study retain high-binding affinity and specificity to the target site. Synthesized as a control group was a library of 'mismatch' polyamides with identical C-terminus modifications but a different core targeted to the DNA sequence 5'-WGGWCW-3', which is not found at the VEGF HRE. The majority of polyamides from both libraries failed to inhibit hypoxia-induced VEGF expression. We identified, however, two non-fluorescent polyamides with biological activity and binding affinities and specificities comparable to those of polyamide-fluorescein conjugate 1.

1.3 Materials and Methods 1.3.1 Synthesis of Polyamides

Polyamides were synthesized by solid phase methods on Kaiser oxime resin (Nova Biochem) except polyamide 3, which was synthesized on Boc-β-alanine-PAM-resin (Peptides International) (19, 20). Fluorescein-labeled polyamides 1-3 were prepared as described previously (16). Polyamides 4-8 and 16-20 were cleaved from resin using the appropriate amine and purified by reverse-phase HPLC. For the synthesis of 9-15 and 21-27, the polyamide was first cleaved with 3,3'-diamino-N-methyl-dipropylamine and purified by reverse-phase HPLC. The designated acid was activated with PyBOP (Nova Biochem) and coupled to the polyamide in dimethylformamide and N,N-diisopropylethylamine to yield the final product after reverse-phase HPLC purification. The purity and identity of all polyamides were verified by analytical HPLC and MALDI-TOF MS.

1.3.2 Confocal Microscopy

Microscopy of live, unfixed cells was performed as described previously (8, 9). Briefly, cells were plated on glass-bottom culture dishes for 24 h prior to overnight incubation with 2 μM polyamide. Imaging was performed on a Zeiss LSM 5 Pascal inverted laser scanning microscope.

1.3.3 Determination of DNA-Binding Affinities and Sequence Specificities

Quantitative DNase I footprint titration experiments were used to determine polyamide-binding affinities ($K_a$) to the 5'-ATACGT-3' sequence within the HRE of the VEGF promoter. These experiments were performed using the 5'-$^{32}$P-labeled 197 bp PCR amplification product of the plasmid pGL2-VEGF-Luc isolated by non-denaturing gel electrophoresis (16, 21). Quantitative DNase I footprint titration experiments were conducted as reported previously (21).

1.3.4 Measurement of Hypoxia-Induced Relative VEGF mRNA

Cells were plated in 24-well plates at a density of 15-20×$10^3$ cells per well (30-40×$10^3$ cells/ml). Polyamides were added to adhered cells in solutions of cell media at the appropriate concentration and allowed to incubate with the cells for 48 h. Then, hypoxic induction of gene expression was chemically induced by adding deferoxamine (DFO) to 300 μM for an additional 16 h (22, 23). Cells were harvested, RNA isolated, cDNA synthesized and quantitative real-time RT-PCR conducted as described previously (16). Briefly, RNA was isolated using the RNeasy kit (Qiagen), cDNA synthesized using Powerscript (BD Biosciences) and quantitative real-time RT-PCR performed using SYBR Green PCR Master Mix (Applied Biosystems) on an ABI 7300 instrument. VEGF expression was measured relative to β-glucuronidase (GUSB) as an endogenous control. Statistical analyses of results were determined using three independent biological replicates. The primer sequences used for VEGF and GUSB are available upon request. HeLa cells were purchased from ATCC and U251 cells were received as a gift from Dr Giovanni Melillo of the National Cancer Institute.

Assays represented in FIGS. 11 and 12 were carried out as follows. U251 cells were plated in 24-well plates at a density of 20–30×$10^3$ cells per well (40–60×$10^3$ cells/ml) in RPMI (ATCC) supplemented with 5% FBS (Irvine Scientific). After 24 hours, polyamides were added to the adhered cells in cell media solutions at the appropriate concentration (0.5 μM and 1 μM) and incubated with the cells for 48 hours. Hypoxic induction of gene expression was chemically induced by adding DFO to 300 μM for an additional 16 hours. Isolation of RNA and subsequent cDNA synthesis were as previously described (19). Briefly, RNA was isolated using the RNeasy kit (Qiagen), cDNA synthesized using Superscript Reverse transcriptase (Invitrogen) and quantitative real-time RT-PCR performed using SYBR Green PCR Master Mix (Applied Biosystems) on an ABI 7300 instrument. Target gene mRNA was measured relative to β-glucuronidase as an endogenous control. Primer employed were: VEGF, L 5'-AGGGCA-GAATCATCACGAAG-3' (SEQ ID NO: 4), R 5'-GGG-TACTCC TGGAAGATGTCC-3' (SEQ ID NO:5); β-glucuronidase, L 5'-CTCATTTGGAATTTTGCCGATT-3' (SEQ ID NO:6), R 5'-CCGAGTGAAGATCCCCTTTTTA-3' (SEQ ID NO:47).

1.3.5 Chromatin Immunoprecipitation

Cells were plated on 15 cm diameter culture dishes and left to attach overnight. Polyamides were incubated with the cells for 48 h, and the cells were incubated for an additional 16 h after the addition of DFO to a final concentration of 300 μM. Cells were then treated with 1% formaldehyde for 10 min. Chromatin was isolated and sheared. HIF-1 antibodies (Novus Biologicals) were used to immunoprecipitate HIF-1 bound DNA fragments. After crosslink reversal, PCRs using primers flanking the HRE of VEGF were used to assess enrichment of bound fragments as compared to mock-precipitated (no antibody) controls. PCRs were monitored either using SYBR Green PCR Master Mix (Applied Biosystems) on an ABI 7300 instrument, or directly visualized using gel electrophoresis.

1.4 Results 1.4.1 Confocal Microscopy of Polyamide-Fluorophore Conjugates 1-3

Cellular uptake of polyamide-fluorescein conjugates 1-3 (FIG. 1) was examined by confocal microscopy in live, unfixed HeLa cells (FIG. 2B). These data demonstrate that polyamide-FITC conjugates 1 and 2, targeted to 5'-WTWCGW-3' and 5'-WGGWCW-3', respectively, both localize in the nucleus of HeLa cells. In contrast, polyamide conjugate 3, also targeted to 5'-WTWCGW-3' but with a β-alanine residue at the C-terminus, is largely extracellular.

1.4.2 Suppression of Hypoxia-Inducible Transcription in Cell Culture by Polyamide-Fluorophore Conjugates 1-3

Induction of VEGF mRNA by the hypoxia mimetic DFO in the presence of polyamides 1-3 in HeLa cells was measured by quantitative real-time RT-PCR (FIG. 2C). Polyamide 1 inhibits the expression of DFO-induced VEGF mRNA production by ~50%. Polyamides 2 and 3 show diminished biological activity compared to 1. Together, the uptake and gene expression data for 1-3 suggest that a polyamide targeted to the HRE of VEGF must have efficient nuclear uptake in order to inhibit hypoxia-induced expression of VEGF. Chromatin immunoprecipitation experiments in cultured HeLa cells were performed to assess whether changes in VEGF promoter occupancy by HIF-1α were consistent with displacement of this protein by polyamide 1. Chromatin immunoprecipitation assays with anti-HIF1α or mock antibody treatment are consistent with inhibition of HIF-1 binding to the HRE in the presence of polyamide 1 and polyamide 2 to a modest degree (FIG. 2D). In the absence of either polyamide 1 or 2, HIF-1 occupies the VEGF HRE following DFO-induction. HIF-1 occupancy at the VEGF HRE is reduced in cells treated with 1 prior to DFO-induction. Polyamide 2 has a more limited effect.

1.4.3 Non-Fluorescent HRE-Targeted Polyamides

We set out to synthesize a series of non-fluorescent HRE-targeted polyamides (4-15) and their mismatch analogs (16-27; FIG. 3). Polyamides 4-15 can be considered in three groups: 4-8 were designed with minimized tail motifs; 9-12 were designed to probe the functional groups present in fluorescein dyes potentially responsible for the favorable nuclear uptake profile of 1; and 13-15 were biotin conjugates. Polyamides 4 and 5 were designed to have tail moieties resembling the linker region of polyamide-fluorescein conjugate 1. The dimethylaminopropylamine tail present in 5 is often placed at the C-terminus of polyamides used in biophysical studies (1, 2, 24). Polyamide 6 was designed to have a tail group of minimal size. Polyamides 7 and 8 have 2-morpholinoethanamine and 3-morpholinopropan-1-amine tail groups, respectively. A four ring polyamide with a morpholino tail was previously shown to have antibacterial activity in a mouse peritonitis model (25). The next group, polyamides 9-12, was designed to reduce molecular weight while retaining functional groups present in fluorescein and maintaining the linker moiety found in polyamide 1. Polyamides 9-12 are derived from benzoic acid; 11 and 12 each contain a carboxylic acid meta- to the attachment site, and 10 and 12 each have a hydroxyl group meta- to the attachment site. Polyamides 13-15 are polyamide-biotin conjugates. The high affinity of the biotin moiety to streptavidin may be useful for biochemical pull-down experiments. Polyamide 13 retains the linker found in 1-3 while 14 and 15 contain 2- and 3-oxygen PEG linkers, respectively. Polyamides 16-27 were synthesized as mismatch control polyamides for 4-15, respectively.

1.4.4 Binding Affinities and Specificities

Polyamides 4-15, designed to bind the 5'-ATACGT-3' HRE-binding site, share the same hairpin polyamide core as polyamides 1 and 3 but have different C-terminus tail groups. The DNA-binding affinities of 4-15 for the HRE of VEGF were measured by quantitative DNase I footprint titrations using a 5'-$^{32}$P-labeled PCR amplification product of the plasmid pGL2-VEGF-Luc, which contains the VEGF HRE. Polyamide conjugate 1 was previously found to have $K_a=6.3\times10^9$ M$^{-1}$ at this site (16). Polyamides 4-15 were footprinted (FIGS. 4 and 8), and the $K_a$ values obtained range from 4.4 (±1.7)×10$^9$ for 15 to 7.7 (±0.9)×10$^{10}$ for 4 (Table 1).

TABLE 1

| Binding affinities (M-1) for polyamides 4-15 | |
| --- | --- |
| Polyamide | 5'-TACGTG-3' |
| 4 | 7.7 (±0.9) × 10$^{10}$ |
| 5 | 6.2 (±1.2) × 10$^{10}$ |
| 6 | 2.5 (±0.3) × 10$^{10}$ |
| 7 | 4.0 (±0.9) × 10$^{10}$ |
| 8 | 3.8 (±0.5) × 10$^{10}$ |
| 9 | 1.5 (±0.6) × 10$^{10}$ |
| 10 | 2.1 (±0.4) × 10$^{10}$ |
| 11 | 2.6 (±0.4) × 10$^{10}$ |
| 12 | 1.1 (±0.2) × 10$^{10}$ |
| 13 | 7.2 (±1.1) × 10$^9$ |

TABLE 1-continued

| Binding affinities (M-1) for polyamides 4-15 | |
| --- | --- |
| Polyamide | 5'-TACGTG-3' |
| 14 | 4.8 (±1.9) × 10$^9$ |
| 15 | 4.4 (±1.7) × 10$^9$ |

Equilibrium association constants reported are mean values from three DNase I footprint titration experiments; standard deviations are shown in parenthese.

With the exception of 15, the values obtained are all higher than that measured for 1. Polyamides 4-15 retain good specificity for the 5'-ATACGT-3' HRE-binding site, although a modest degree of non-specific binding is observed at high concentrations for polyamides 4, 5, 7, 8 and 10. Modifications to the tail moiety did not significantly abrogate high-binding affinity and specificity.

1.4.5 Screening for Suppression of Hypoxia-Inducible Transcription by Polyamides 4-27 in HeLa Cells Induction of VEGF mRNA by the hypoxia mimetic DFO in HeLa cells in the presence of polyamides 4-15 was measured by quantitative real-time RT-PCR and compared to that of polyamide 1 (FIG. 5). Polyamides 5, 6 and 8 showed modest inhibition of induced VEGF expression and polyamides 4 and 7 showed no difference relative to the untreated, induced control. Mismatch polyamides 16-19 showed no difference in VEGF mRNA relative to the untreated, induced control. Polyamide 20 showed a modest effect (FIG. 9).

Polyamides 9 and 10 had a modest effect on induced VEGF expression, whereas 11 and 12 inhibited induced VEGF expression comparably to polyamide 1. Control polyamides 23 and 24 had a reduced effect as compared with their match congeners 11 and 12 (FIG. 6). HeLa cell growth was not inhibited by 11, 12, 23 or 24 at 1 µM (FIG. 10).

Polyamides 13-15 had a modest effect on induced VEGF expression. An appreciable difference between relative VEGF mRNA levels was seen in cells treated with biotin conjugates 13 and 14 and their mismatch congeners 25 and 26 (FIG. 9). It is noted that cells treated with polyamides 25 and 26 had VEGF expression slightly higher than that of the untreated, induced control.

1.4.6 Suppression of Hypoxia-Inducible Transcription by Polyamides in U251 Cells The effects of HRE targeted polyamides 1 and 11 and control polyamides 2 and 23 were tested in U251 cells, which express a higher level of VEGF than HeLa cells (FIG. 7). Uptake of optically tagged polyamides 1 and 2 was examined by confocal microscopy in live, unfixed U251 cells dosed with 2 µM of 1 or 2 (FIG. 7A). Induction of VEGF mRNA in the presence of polyamides 1 and 11 was inhibited dose dependently (FIG. 7B). Polyamide 2 had minimal effect on VEGF expression at 0.2 µM. However, at 1 µM, polyamide 2 had a moderate effect, though still less than that of its match congener 1. Polyamide 23 had a more modest effect than its match congener 11 at both 0.2 and 1 µM. We also undertook chromatin immunoprecipitation experiments in U251 cells to assess changes in VEGF promoter occupancy by HIF-1α in the presence of 1, 2, 11 and 23 (FIG. 7C). Chromatin immunoprecipitation assays with anti-HIF1α or mock antibody treatment are consistent with decreased occupancy of HIF-1α at the VEGF HRE in the presence of polyamides 1 and 11 at 1 µM. Polyamide 23 has a more modest effect compared with that of its match congener 11. At the concentration tested (1 µM), polyamide 2 has an effect statistically similar, though slightly less than that of 1. This is not unexpected; 2 also showed some inhibition of VEGF mRNA at this concentration. PCR amplification at an irrelevant locus in the coding region of GUSB showed minimal enrichment (~1- to 1.5-fold over background) for polyamide-treated and control samples (data not shown).

The effects of HRE targeted polyamides 4, 11 and 28-38 and control polyamides 16, 23 and 39-49 (FIG. 11) were tested in U251 cells and the results are shown in FIG. 12.

1.5 Discussion

Previous studies on fluorophore-labeled polyamides have revealed several parameters that affect cellular trafficking of these molecules, including number of heterocyclic ring pairs, relative Py/Im content and sequence, and choice of fluorophore and attachment site (8, 9). Among fluorophores considered, the protonation state of fluorescein is pH sensitive, while those of tetramethylrhodamine and BODIPY™ (boron-dipyrromethene) are not. In previous work, nuclear localization of polyamide 2 in HeLa cells was ablated when the cells were grown in glucose- and sodium pyruvate-free media, but subsequently restored when normal growth media were added (8). This suggests that for some polyamides, nuclear localization is energy dependent. Many fluorophore-polyamide conjugates that exhibit a punctate, cytoplasmic staining pattern co-localize with LysoTracker, a lysosomal stain. Verapamil, a calcium channel and P-glycoprotein efflux pump inhibitor, was shown to facilitate nuclear uptake of a BODIPY™-polyamide conjugate otherwise sequestered within cytoplasmic vesicles (7). Some polyamides with minimal nuclear localization, e.g. 3, localize mostly in the extracellular space. Nevertheless, the fact that many eight-ring hairpin polyamide-fluorophore conjugates do localize in the nuclei of live cells is encouraging.

The inhibition of induced VEGF expression in the presence of polyamide 1, which binds the VEGF HRE, is an important proof-of-principle experiment for the use of designed DNA-binding ligands to modulate the expression of specific sets of genes. Moving ahead, anticipated experiments include studies in mammalian model systems to account for biodistribution, availability and metabolism of polyamides. Toward this end, we have attempted to identify polyamides capable of nuclear localization but of simpler structures and lower molecular weights than dye conjugates. The inhibition of induced VEGF expression with HRE-targeted polyamide 1, but not 2, which targets a different DNA sequence or 3, which exhibits considerably less nuclear localization, demonstrates the viability of VEGF inhibition as a proxy for nuclear localization of polyamides that bind the HRE.

The ability to interrogate polyamide cellular uptake and nuclear localization by affecting expression of an endogenous inducible gene enables exploration of the nuclear uptake profiles of non-fluorescent tail moieties. The quantitative real-time RT-PCR data presented show that removal of the fluorescein dye (polyamide 4) and step-wise ablation of the linker moiety (polyamides 5 and 6) diminish the biological activity of these compounds as compared with polyamide 1 in this system. The $K_a$ values measured for 4-6 are between 4- and 12-fold higher than that measured for the parent polyamide 1 on the same DNA sequence. Similarly, the binding affinities of N-alkylaminemorpholino tail polyamides 7 and 8 are ~6-fold higher than that of the parent polyamide 1 for the same binding site, but only modest biological activities are observed.

Data generated from cultured HeLa cells treated with polyamides 9-12 were more encouraging. These compounds were designed to probe contributions of the alcohol and carboxylic acid groups of fluorescein to the cellular uptake and nuclear localization observed for 1. This was done by synthesizing a focused series of polyamides composed of an amide-bond linked benzene ring containing four possible permutations of alcohol and/or carboxylic acid substituents at the meta-positions. Polyamides 9-12 demonstrated good sequence specificities and binding affinities greater than that of 1. Polyamide conjugates of benzoic acid and 3-hydroxy benzoic acid, 9 and 10, respectively, show a modest degree of biological activity, but those conjugated to either isophthalic acid or 5-hydroxy isophthalic acid, 11 and 12, respectively, demonstrate a biological effect similar to that observed for the parent polyamide 1. These results suggest that the presence of the carboxylic acid group on the benzene ring is a positive determinant of nuclear localization in this system.

Biotin conjugates 13-15 differ in the identity of the linker moiety and were of interest due to the potential utility of these conjugates for pull-down experiments. The binding affinities measured by quantitative DNase I footprint titration experiments for these conjugates were similar to that of the parent polyamide 1. By quantitative real-time RT-PCR, polyamides 13-15 all demonstrated modest biological activities and the results do not suggest strong differences in activities based on linker identity. The modest activities of the biotin conjugates, which might reflect a moderate degree of nuclear uptake, are neither encouraging nor dismissive of potential applications of these conjugates.

Our working hypothesis regarding VEGF inhibition by polyamides is through direct interactions with the DNA-HIF-1 interface at the HRE that prevents HIF-1 binding, most likely by an allosteric mechanism. To explore this model further, we used chromatin immunoprecipitation to assess HIF-1 occupancy at the VEGF HRE under hypoxia-induced conditions in HeLa cells in the presence and absence of match (and mismatch) polyamides with variable C-terminus tails. Antibodies against HIF-1α were found to enrich fragments of DNA containing the VEGF HRE after DFO-induction. This enrichment was reduced in samples treated with polyamide 1 and, to a lesser extent, polyamide 2. We also undertook experiments in U251 cells, which express VEGF more robustly and have previously been used as a model cell line for studying hypoxia-induced VEGF expression (17).

Polyamide-fluorescein conjugates 1 and 2 localize in the nucleus of U251 cells. Induction of VEGF mRNA in the presence of polyamides 1, 2, 11 and 23 at 0.2 and 1 μM in U251 cells was measured by quantitative real-time RT-PCR. Polyamide 1 showed significant inhibition at both concentrations. Interestingly, at 1 μM polyamide 2 showed inhibition greater than that measured in HeLa cells but still significantly less than 1. Polyamide 11 exhibits dose-dependent inhibition of VEGF similar to that measured in HeLa cells, while 23 showed modest activity at both concentrations comparable to that measured in HeLa cells. Chromatin immunoprecipitation of HIF-1α from U251 cells treated with HRE-targeted polyamides 1 and 11 and mismatch polyamides 2 and 23 shows that enrichment of HIF-1α bound DNA fragments containing the VEGF HRE after DFO induction is inhibited by pre-treatment with polyamides 1 and 11, and to a lesser extent 2 and 23. This is generally consistent with a mechanism whereby polyamides 1 and 11 exert their effect by preventing HIF-1 binding to the cognate HRE. This is also consistent with DNase I footprint titrations and gel shift assays in vitro (16).

This report identifies two polyamides, 11 and 12, with non-fluorescent moieties at the C-terminus that bind the VEGF HRE that have biological activity similar to that of the fluorescein-polyamide conjugate 1 known to localize in the nucleus. Both polyamides retain an amide-linked benzene ring with a carboxylic acid meta- to the attachment point and are similar in structure to the proximal portion of fluorescein. Work is ongoing to synthesize a second series of polyamides designed to examine the role of the aromatic ring and the carboxylic acid functional group in aiding nuclear localization. As the mechanism of polyamide uptake and nuclear localization continues to be elucidated, it is currently unclear whether the biological activity of 11 and 12 is due to improved ability to buffer the wide range of pH values that may be encountered in the cell (e.g. lysosomes), improved nuclear localization resulting in an increased effective polyamide concentration at the DNA, or decreased efflux of polyamide from the cell perhaps through one or several ATP-dependent drug efflux pumps (26, 27).

1.6 References

1. Dervan, P. B. and Edelson, B. S. (2003) Recognition of the DNA minor groove by pyrrole-imidazole polyamides *Curr. Opin. Struct. Biol,* 13, 284-299.
2. Dervan, P. B., Poulin-Kerstien, A. T., Fechter, E. J., Edelson, B. S. (2005) Regulation of gene expression by synthetic DNA-binding ligands *Top. Curr. Chem,* 253, 1-31.
3. White, S., Szewczyk, J. W., Turner, J. M., Baird, E. E., Dervan, P. B. (1998) Recognition of the four Watson-Crick base pairs in the DNA minor groove by synthetic ligands *Nature,* 391, 468-471.
4. Kielkopf, C. L., Baird, E. E., Dervan, P. D., Rees, D. C. (1998) Structural basis for G•C recognition in the DNA minor groove *Nature Struct. Biol,* 5, 104-109.
5. Foister, S., Marques, M. A., Doss, R. M., Dervan, P. B. (2003) Shape selective recognition of T-A base pairs by hairpin polyamides containing N-terminal 3-methoxy (and 3-chloro) thiophene residues *Bioorg. Med. Chem,* 11, 4333-4340.
6. Belitsky, J. M., Leslie, S. J., Arora, P. S., Beerman, T. A., Dervan, P. B. (2002) Cellular uptake of N-methylpyrrole/N-methylimidazole polyamide-dye conjugates *Bioorg. Med. Chem,* 10, 3313-3318.
7. Crowley, K. S., Phillion, D. P., Woodard, S. S., Schweitzer, B. A., Singh, M., Shabany, H., Burnette, B., Hippenmeyer, P., Heitmeier, M., Bashkin, J. K. (2003) Controlling the intracellular localization of fluorescent polyamide analogues in cultured cells *Bioorg. Med. Chem. Lett,* 13, 1565-1570.
8. Best, T. P., Edelson, B. S., Nickols, N. G., Dervan, P. B. (2003) Nuclear localization of pyrrole-imidazole polyamide-fluorescein conjugates in cell culture *Proc. Natl. Acad. Sci. USA,* 100, 12063-12068.
9. Edelson, B. S., Best, T. P., Olenyuk, B., Nickols, N. G., Doss, R. M., Foister, S., Heckel, A., Dervan, P. B. (2004) Influence of structural variation on nuclear localization of DNA-binding polyamide-fluorophore conjugates *Nucleic Acids Res,* 32, 2802-2818.
10. Suto, R. K., Edayathumangalam, R. S., White, C. L., Melander, C., Gottesfeld, J. M., Dervan, P. B., Luger, K. (2003) Crystal structures of nucleosome core particles in complex with minor groove DNA-binding ligands *J. Mol. Biol,* 326, 371-380.
11. Dudouet, B., Burnett, R., Dickinson, L. A., Wood, M. R., Melander, C., Belitsky, J. M., Edelson, B., Wurtz, N., Briehn, C., Dervan, P. B., et al. (2003) Accessibility of nuclear chromatin by DNA binding polyamides *Chem. Biol,* 10, 859-867.
12. Gottesfeld, J. M., Neely, L., Trauger, J. W., Baird, E. E., Dervan, P. B. (1997) Regulation of gene expression by small molecules *Nature,* 387, 202-205.
13. Dickinson, L. A., Gulizia, R. J., Trauger, J. W., Baird, E. E., Mosier, D. E., Gottesfeld, J. M., Dervan, P. B. (1998) Inhibition of RNA polymerase II transcription in human cells by synthetic DNA-binding ligands *Proc. Natl. Acad. Sci. USA,* 95, 12890-12895.
14. Nguyen-Hackley, D. H., Ramm, E., Taylor, C. M., Joung, J. K., Dervan, P. B., Pabo, C. O. (2004) Allosteric inhibition of zinc-finger binding in the major groove of DNA by minor-groove binding ligands *Biochemistry,* 43, 3880-3890.
15. Wurtz, N. R., Pomerantz, J. L., Baltimore, D., Dervan, P. B. (2002) Inhibition of DNA binding by NF-kappa B with pyrrole-imidazole polyamides *Biochemistry,* 41, 7604-7609.
16. Olenyuk, B. Z., Zhang, G. J., Klco, J. M., Nickols, N. G., Kaelin, W. G., Dervan, P. B. (2004) Inhibition of vascular endothelial growth factor with a sequence-specific hypoxia response element antagonist *Proc. Natl. Acad. Sci. USA,* 101, 16768-16773.
17. Kong, D. H., Park, E. J., Stephen, A. G., Calvani, M., Cardellina, J. H., Monks, A., Fisher, R. J., Shoemaker, R. H., Melillo, G. (2005) Echinomycin, a small-molecule inhibitor of hypoxia-inducible factor-1 DNA-binding activity *Cancer Res,* 65, 9047-9055.
18. Vandyke, M. M. and Dervan, P. B. (1984) Echinomycin binding-sites on DNA *Science,* 225, 1122-1127.
19. Baird, E. E. and Dervan, P. B. (1996) Solid phase synthesis of polyamides containing imidazole and pyrrole amino acids *J. Am. Chem. Soc,* 118, 6141-6146.
20. Belitsky, J. M., Nguyen, D. H., Wurtz, N. R., Dervan, P. B. (2002) Solid-phase synthesis of DNA binding polyamides on oxime resin *Bioorg Med. Chem,* 10, 2767-2774.
21. Trauger, J. W. and Dervan, P. B. (2001) Footprinting methods for analysis of pyrrole-imidazole polyamide/DNA complexes *Methods Enzymol,* 340, 450-466.
22. Wood, S. M. and Ratcliffe, P. J. (1997) Mammalian oxygen sensing and hypoxia inducible factor-1 *Int. J. Biochem. Cell Biol,* 29, 1419-1432.
23. Bianchi, L., Tacchini, L., Cairo, G. (1999) HIF-1-mediated activation of transferrin receptor gene transcription by iron chelation *Nucleic Acids Res,* 27, 4223-4227.
24. Dervan, P. B. (2001) Molecular recognition of DNA by small molecules *Bioorg. Med. Chem,* 9, 2215-2235.
25. Kaizerman, J. A., Gross, M. L., Ge, Y. G., White, S., Hu, W. H., Duan, J. X., Baird, E. E., Johnson, K. W., Tanaka, R. D., Moser, H. E., et al. (2003) DNA binding ligands targeting drug-resistant bacteria: structure, activity, and pharmacology *J. Med. Chem,* 46, 3914-3929.
26. Juliano, R. L. and Ling, V. (1976) Surface glycoprotein modulating drug permeability in Chinese-hamster ovary cell mutants *Biochim. Biophys. Acta,* 455, 152-162.
27. Ueda, K., Cardarelli, C., Gottesman, M. M., Pastan, I. (1987) Expression of a full-length cDNA for the human Mdr1 gene confers resistance to colchicine, doxorubicin, and vinblastine *Proc. Natl. Acad. Sci. USA,* 84, 3004-3008.

Example 2

Modulating Hypoxia-Inducible Transcription by Disrupting HIF-1-DNA Interface 2.1 Abstract Transcription mediated by hypoxia inducible factor (HIF-1) contributes to tumor angiogenesis and metastasis but is also involved in activation of cell-death pathways and normal physiological processes. Given the complexity of HIF-1 signaling it could be advantageous to target a subset of HIF-1 effectors rather than the entire pathway. We compare the genome-wide effects of three molecules that each interfere with the HIF-1-DNA interaction: a polyamide targeted to the hypoxia response element (HRE), siRNA targeted to HIF-1α, and echinomycin, a DNA-binding natural product with a similar but less specific sequence preference than the polyamide. The polyamide affects a subset of hypoxia-induced genes consistent with its binding site preferences. For comparison, HIF-1α siRNA and echinomycin each affect the expression of nearly every gene induced by hypoxia. Remarkably, the total number of genes affected by either polyamide or HIF-1α siRNA over a range of thresholds is comparable. The data show that polyamides can be used to affect a subset of a pathway regulated by a transcription factor. In addition, this study offers a unique comparison of three complementary approaches towards exogenous control of endogenous gene expression.

2.2 Introduction

Exogenous chemical and biological methods to control directly expression of selected endogenous genes could have broad implications for human medicine. Towards this goal, a number of technological approaches are currently being investigated. Polydactyl zinc finger proteins are a programmable class of DNA binding proteins capable of sequence-specific binding (1, 2). These designed proteins have been used to inhibit expression of target genes (3), and transcriptional activator domain-zinc finger conjugates have been used to activate expression of target genes (4). The RNA-interference pathway can be used to regulate gene expression at the post-transcriptional level (5). siRNA and shRNA molecules enlist cellular machinery to degrade selected mRNA targets (6, 7). RNAi technology has been highly effective in achieving potent and specific knock-down of target mRNAs and is now widely used to probe target gene function (8). However, bioavailability and delivery of zinc finger proteins and siRNA to targets in humans could be an obstacle to their therapeutic application and continues to receive considerable attention (8). Cell-permeable small molecules that modulate protein-protein or protein-DNA interactions offer another approach to the control of endogenous gene regulation. Screening small molecule and natural product libraries for a desired effect can identify candidate molecules with high likelihoods of possessing drug-like bioavailability; drawbacks include the need to screen anew for each target protein-protein or protein-DNA interaction. Polyamides containing N-methylimidazole (Im) and N-methylpyrrole (Py) are a class of programmable DNA-binding small molecules previously used to disrupt protein-DNA interactions in a sequence-specific manner in cell culture (9, 10).

Controlling the transcriptional activity of hypoxia inducible factor (HIF-1), a heterodimer of HIF-1α and HIF-1β (ARNT), is a clinically relevant goal (11-14). HIF-1 is the principal mediator of the adaptive cellular response to hypoxia (15). Under normoxic conditions, HIF-1α is specifically hydroxylated by an iron-dependent proline hydroxylase, ubiquitinated by the von Hippel-Lindau (VHL) tumor suppressor protein-ubiquitin ligase protein complex, and degraded by the proteosome (16). Iron chelators, such as deferoxamine (DFO), can be used to mimic hypoxia in cell culture (16). Through interaction with co-activators p300/CBP, HIF-1 directly activates the expression of at least 100 genes involved in cellular and tissue adaptation to hypoxia (13), including pro-angiogenic factors such as vascular endothelial growth factor (VEGF), glycolytic enzymes, extra-cellular matrix remodeling enzymes, and genes involved in both pro-survival and death pathways (11). HIF-1 activation by the hypoxic microenvironment of solid tumors, or by deactivating mutations in VHL, contribute to an aggressive phenotype of increased cell proliferation, invasion, metastasis, and drug resistance (11). Given the complexity of HIF-1 signaling in cellular survival and death pathways, and its critical role in physiological processes in normal tissues, it could be advantageous to target a subset of HIF-1 effectors rather than the entire pathway (13).

In important proof of principle experiments, introduction of siRNA against HIF-2α to VHL$^{-/-}$ renal carcinoma cells was sufficient to abrogate tumor formation by these cells in mice (17). Screening for small molecules capable of disrupting the HIF-1-p300 interaction identified chetomin, a natural product that binds p300 that was shown to inhibit expression of HIF-1 regulated genes and exhibit anti-tumor activity in a mouse model (18). In an effort to inhibit directly HIF-1-DNA binding, a hairpin polyamide was designed to bind the sequence 5'-ATACGT-3' found in the VEGF HRE. This polyamide bound its target site and prevented HIF-1-DNA binding in a sequence specific manner, and inhibited hypoxia-induced expression of VEGF and several other HIF-1 regulated genes in cultured cells without the use of transfection agents (19, 20). Melillo and colleagues screened a library of small molecules for inhibition of HIF-1 mediated transcription in a cell-based assay and identified the natural product echinomycin, a DNA-binding bisintercalator (21). Echinomycin binds the four base pair sequence 5'-NCGN-3' found in the consensus HRE 5'-NACGTG-3' and inhibited expression of VEGF in cultured cells (22).

To establish a benchmark of comparison for the global effects of polyamides, we compare the genome-wide effects on U251 cells induced with DFO of a polyamide targeted to the HRE sequence 5'-WTWCGW-3', echinomycin, and siRNA targeted against HIF-1α. siRNA-mediated destruction of HIF-1α mRNA establishes a maximum level of inhibition that can be achieved for HIF-1 target genes through disruption of the HIF-1-HRE interaction. Nearly all transcripts induced by DFO are inhibited by both HIF-1α siRNA and echinomycin. Polyamide 11.1 (FIG. 13) inhibits only a subset of these genes, and shows a preference for genes containing HREs of the sequence 5'-(T/A)ACGTG-3', consistent with this molecule's predicted binding preferences. Remarkably, the total number of genes affected by either polyamide 11.1 or HIF-1α siRNA over a range of thresholds is comparable. We show that HIF-1 occupancy at the HREs of two genes affected by polyamide 11.1 is reduced in the presence of the polyamide, while HIF-1 occupancy at the HREs of two unaffected genes is unchanged. We also show that a polyamide that binds a site immediately 5' to the VEGF HRE inhibits induced expression of VEGF but not of FLT1, a HIF-1 target gene lacking this flanking site.

Figure 14A:
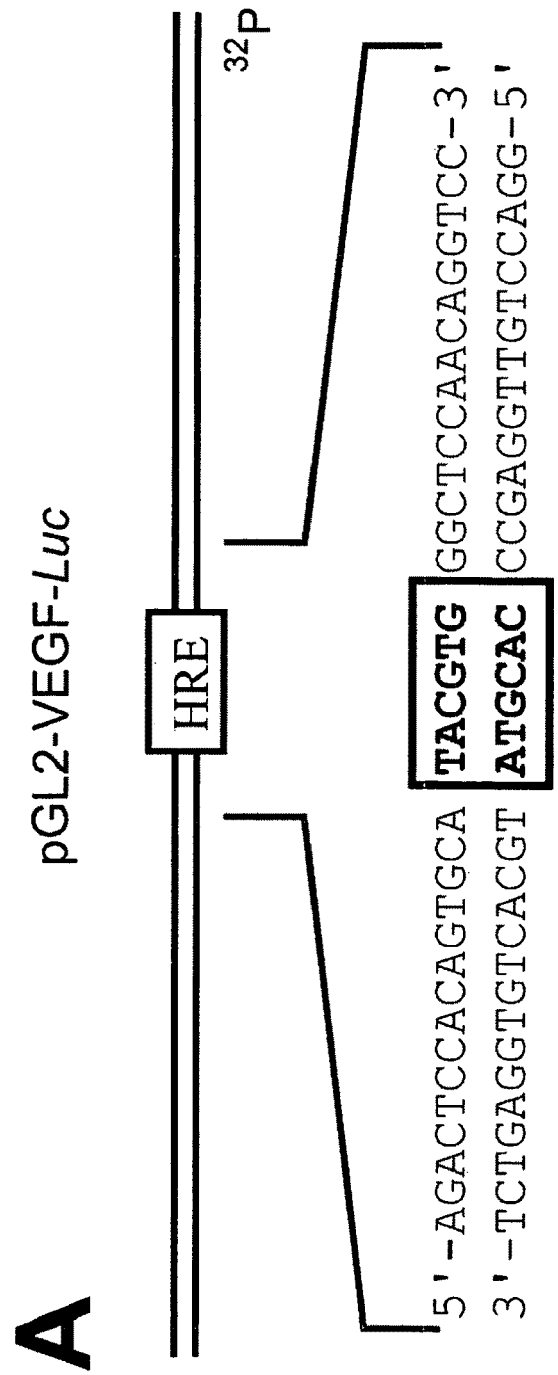
Figure 14B:
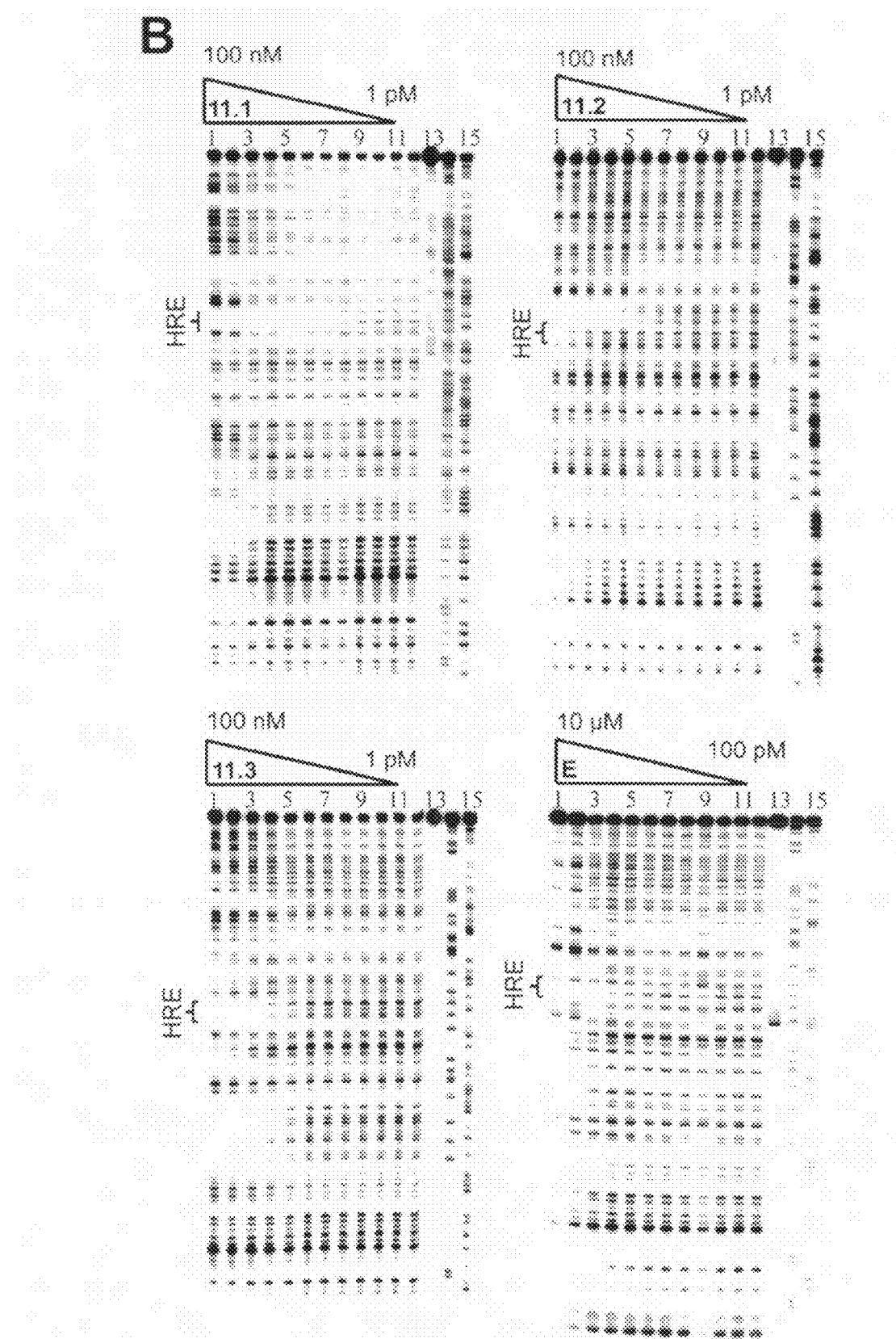

2.3 Results and Discussion 2.3.1 Binding of Polyamide 11.1, 11.2, 11.3 and Echinomycin at the VEGF and FLT1 HREs Polyamide sequence specificity is programmed by side-by-side pairings of heterocyclic amino acids in the minor groove of DNA: Im/Py distinguishes G•C from C•G; Py/Py binds both A•T and T•A; 3-chlorothiophene/N-methylpyrrole (Ct/Py) prefers T•A at the N-terminus position (23-25). Polyamide 11.1 and echinomycin are expected to bind at the VEGF HRE sequence 5'-TACGTG-3'. Polyamide 11.2 is expected to bind the sequence 5'-AGTGCA-3' immediately 5' to the VEGF promoter HRE. HRE-mismatch control polyamide 11.3 targets the sequence 5'-WGGWCW-3', which is not found near the VEGF HRE. (FIG. 13) The DNA-binding affinities of 11.2, 11.3 and echinomycin for the VEGF HRE were measured by quantitative DNase I footprint titrations using a 5' $^{32}$P-labeled PCR amplification product of the plasmid pGL2-VEGF-Luc containing the VEGF HRE (FIGS. 14A and B). Polyamide 11.1 was previously found to bind the VEGF HRE ($K_a$=2.6 (±0.4)×10$^{10}$ M$^{-1}$) (20). For ease of comparison, a footprinting gel of 11.1 is included. Polyamide 11.2 binds the site 5'-AGTGCA-3' immediately 5' to the VEGF HRE ($K_a$=3.2 (+0.6)×10$^9$ M$^{-1}$). Echinomycin binds the VEGF HRE ($K_a$=8.4 (±2.1)×10$^6$ M$^{-1}$). Polyamide 11.3 binds the VEGF HRE ($K_a$=8.0 (±1.0)×10$^8$ M$^{-1}$), and approximately 35 basepairs 3' of the HRE, most likely two 5'-WG-WCW-3' sites ($K_a$=7.6 (±1.0)×10$^8$ M$^{-1}$).

Figure 14C:
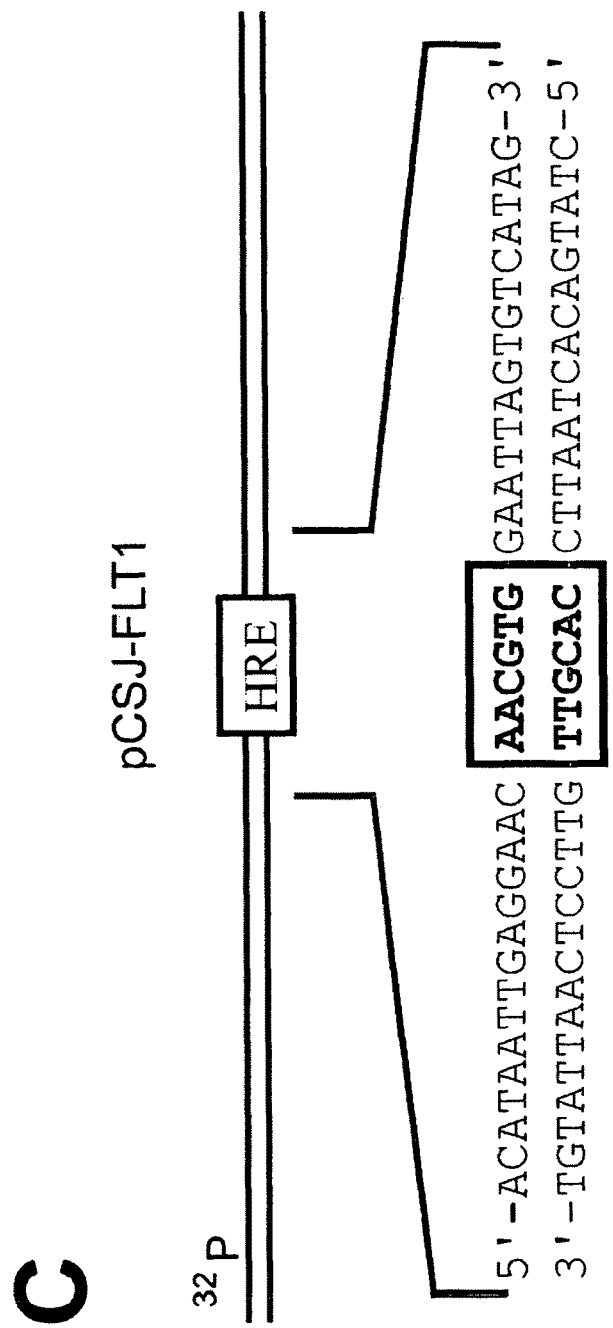
Figure 14D:
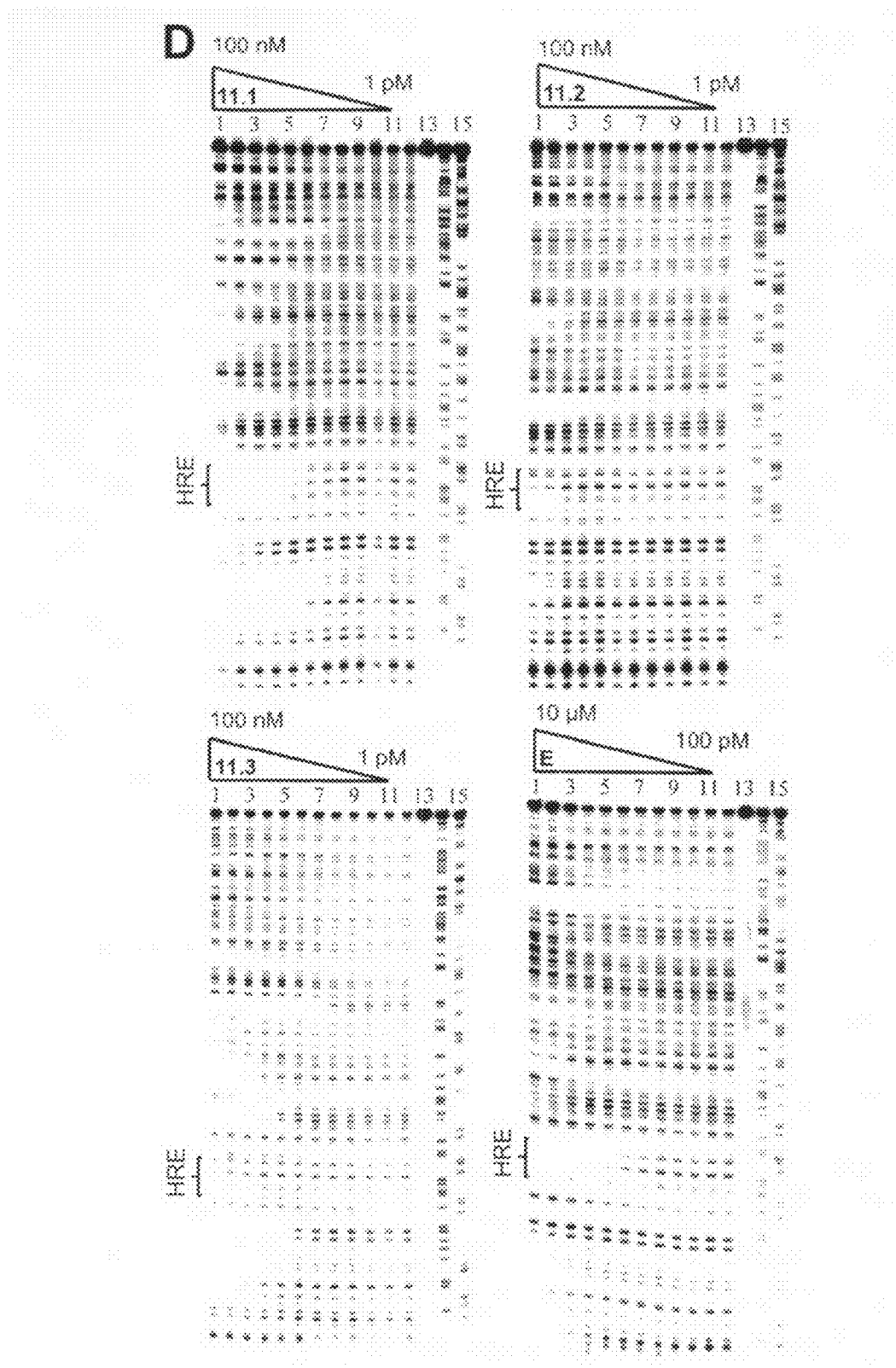

The DNA-binding affinities of 11.1, 11.2, 11.3 and echinomycin for the HRE of FLT1 were measured by quantitative DNase I footprint titrations using a 5' $^{32}$P-labeled PCR amplification product of the plasmid pCSJ-FLT1 (FIGS. 14C and D). Although formally targeted to the sequence 5'-WTWCGW-3', polyamide 11.1 would be expected to bind 5'-CAACGT-3', albeit with a moderate decrease in affinity (25). The sequence preference of a Ct/Py pair for T•A is approximately 4-fold over A•T, but 50-fold over a G•C (25). Polyamide 11.1 binds the FLT1 HRE ($K_a$=2.7 (+0.2)×10$^9$ M$^{-1}$). Polyamide 11.2 binds the FLT1 HRE ($K_a$=2.2 (±0.8)×10$^8$ M$^{-1}$). Echinomycin binds the FLT1 HRE ($K_a$=2.9 (±0.7)×10$^7$ M$^{-1}$). Polyamide 11.3 does not bind the FLT1 HRE with a measurable $K_a$, but was observed to bind a 5'-AGACA-3' site 16 basepairs 5' to the FLT1 HRE ($K_a$=2.7 (±0.4)×10$^9$ M$^{-1}$).

2.3.2 Suppression of Induced VEGF and FLT1 Expression

HIF-1 induces VEGF expression by binding to the 5'-TACGTG-3' HRE located approximately 950 base pairs upstream of the transcription start site (26, 27). The effect on induced VEGF expression by siRNA silencing of HIF-1α mRNA establishes a theoretical maximum level of inhibition through disruption of HIF-1-DNA binding. HIF-1α mRNA was reduced by approximately 95% in the presence of HIF-1α siRNA, but was minimally affected by polyamides 11.1, 11.2 or echinomycin under induced conditions (FIG. 15). A mismatch control siRNA did not reduce HIF-1α mRNA. Polyamides 11.1 and 11.2 (1 μM) and HIF-1α siRNA had similar effects on induced VEGF expression; treatment inhibited most of the increase in VEGF mRNA following DFO treatment, but not to levels below that observed for non-induced controls (FIG. 15A). As previously reported, 100 nM echinomycin potently inhibits VEGF expression to levels below the non-induced control (21). HRE-mismatch control polyamide 11.3, which binds the HRE with a much reduced affinity relative to 11.1, had a more modest effect on VEGF mRNA levels. It is also possible that the modest but measurable effect of polyamide 11.3 on VEGF expression could be due to interference with other protein-DNA interactions elsewhere in the promoter or enhancer of VEGF, or is due to secondary effects from direct effects on other genes. A mismatch control siRNA had a limited effect on VEGF mRNA levels.

Induction of FLT1 (VEFG receptor type 1) is mediated by HIF-1 binding to the 5'-AACGTG-3' HRE in the FLT1 promoter (28). Polyamide 11.1 and HIF-1α siRNA both inhibited FLT1 expression following DFO induction (FIG. 15B). Echinomycin reduced FLT1 expression to below that of the non-induced control. Polyamides 11.2 and 11.3 had minimal effect. A mismatch control siRNA also had a limited effect on FLT1 mRNA levels. Given the relative binding affinities of polyamide 11.1 and echinomycin, it may be surprising that 1 μM of polyamide 11.1 is necessary to inhibit VEGF and FLT1 expression comparably to HIF-1α siRNA, while 100 nM echinomycin reduces their expression to sub-basal levels. The structure of double-helical DNA is not greatly perturbed by minor groove-binding hairpin polyamides (23); echinomycin-DNA binding causes local unwinding and lengthening of the DNA helix, which might account for its greater potency in these experiments (29, 30). Polyamide-intercalator conjugates have been shown to unwind DNA in a sequence-specific fashion and to improve the ability of a polyamide to inhibit binding of several DNA-binding proteins in vitro (31, 32). Attempts to use polyamide-intercalator conjugates to target the VEGF HRE have not been successful due to poor nuclear uptake.

The ability to target DNA sequences flanking critical protein-DNA binding sites while maintaining productive inhibition of protein-DNA binding expands the repertoire of such interactions amenable to inhibition by polyamides. In a similar approach, Kageyama et al. showed that polyamides targeted to sequences flanking the VEGF HRE could inhibit VEGF expression (33). Polyamides targeted to flanking sites have previously successfully inhibited protein-DNA binding in the cases of TATA-binding protein and LEF-1 (34). It should be noted that minor groove-binding polyamides and some major groove-binding proteins co-occupy DNA sequences in some cases (35).

2.3.3 Microarray Analysis of Gene Expression

One potential limitation to the use of hairpin-polyamides for gene regulation is binding site size and specificity for match versus mismatch sites, which may result in prohibitively large numbers of affected genes. To examine this, the global effects of polyamide treatment on hypoxia-induced gene expression were measured using Affymetrix Human Genome U133 Plus 2.0 Arrays containing oligonucleotide sequences representing more than 50,000 transcripts. To establish a benchmark for comparison, the effects of HIF-1α siRNA and echinomycin were also measured. Experiments were conducted in triplicate, and gene expression levels normalized to DFO-treated controls. Cells not treated with DFO were normalized to DFO-treated controls.

Polyamide 11.1 (1 μM) affected expression of 2,284 transcripts by more than 2-fold (p≦0.01) (Table 2). At the same threshold, HIF-1α siRNA affected 3,190 transcripts and echinomycin (100 nM) affected 10,906.

TABLE 2

Number of transcripts affected (p ≦ 0.01).

| | Treatment | | | |
|---|---|---|---|---|
| | — | R | E | 11.1 |
| | DFO | | | |
| | − | + | + | + |
| up-regulated (fold change ≧ 2.0) | 662 | 1,380 | 3,480 | 709 |
| down-regulated (fold change ≦ −2.0) | 1,480 | 1,810 | 7,426 | 1,575 |
| up-regulatd (fold change ≧ 4.0) | 62 | 122 | 413 | 57 |
| down-regulated (fold change ≦ −4.0) | 296 | 356 | 4,133 | 336 |

R, HIF-1α siRNA;
E, echinomycin;
11.1, polyamide.

In all cases, a majority of affected genes were down-regulated. For comparison, DFO treatment alone affected expression of 2,142 transcripts (4.6% of interrogated transcripts), with a majority up-regulated. Clustering analysis was performed to identify similarities in the expression profiles between the different treatments (FIG. 16). The expression profile of cells treated with HIF-1α siRNA is similar to that of cells not treated with DFO under the conditions of the analysis; the expression profiles of echinomycin-treated and polyamide-treated cells are less similar to each other and to the other treatments. Analysis of transcripts affected by both 11.1 and HIF-1α siRNA shows that 395 and 150 transcripts are commonly down- and up-regulated, respectively, at least 2-fold (p≦0.01). A similar analysis of transcripts affected by both 11.1 and echinomycin shows that 731 and 112 transcripts are commonly down- and up-regulated, respectively. Analysis of transcripts affected by both siRNA and echinomycin shows that 1140 and 443 transcripts are commonly down- and up-regulated, respectively. A side-by-side, genome-wide expression analysis of fluorescein-tagged analogs of polyamides 11.1 and 11.3 in DFO-induced cells was previously reported (19), and found that a majority of genes were uniquely affected by each polyamide, with a number of genes commonly affected, under the conditions of the experiments. It is not entirely unsurprising that there is some overlap in genes affected by polyamides targeted to different DNA sequences, given that we do not have a full understanding of all DNA sequences involved in the direct or indirect regulation of a given gene.

We find that DFO induced the expression of a set of 297 transcripts by at least 4-fold ($p \leq 0.01$) (FIG. 16B). Of this set, 69 were inhibited by polyamide 11.1 (designated as 1 in FIG. 16) by at least 2-fold ($p \leq 0.01$). For comparison, HIF-1α siRNA inhibited 244, and echinomycin 263 of the 297 DFO-induced transcripts. It is not known what proportion of these affected transcripts are direct HIF-1 targets. To examine more closely the effects of polyamide 11.1, HIF-1α siRNA, and echinomycin on transcripts induced directly by HIF-1, we examined a limited set of 31 transcripts consisting of previously identified direct HIF-1 targets that were induced at least 1.5-fold ($p \leq 0.01$) by DFO in this experiment (FIG. 16C) (28, 36-45) Nearly all 31 transcripts in this set were down-regulated by HIF-1α siRNA. In most cases, the expression was reduced to levels observed in cells untreated with DFO. Echinomycin treatment resulted in down-regulation of all 31 transcripts. For some genes, including VEGF, expression was reduced to levels far below those of the siRNA-treated cells and non-induced controls. Polyamide 11.1 inhibited the expression of 14 of these but displayed minimal effect on the others.

The HRE sequences for these genes, where known, are displayed in Table 3.

TABLE 3

HIF-1 induced genes affected by HIF-1α siRNA (R), echinomycin (E, 100 nM), 11.1 (1 µM), and 11.3 (1 µM).

| | HRE(s) (5' to 3') | R | E | 11.1 | 11.3 |
|---|---|---|---|---|---|
| TFRC | agcgTACGTGcctc (SEQ ID NO: 8) | -2.0 | -2.3 | 1.1 | 1.4 |
| PKFB3 | gcggGACGTGacgc (SEQ ID NO: 9) gacgCACGTGggca (SEQ ID NO: 10) | -5.5 | -82.0 | 1.0 | 1.0 |
| LDHA | ggcgGACGTGcggg (SEQ ID NO: 11) ctcaCACGTGggtt (SEQ ID NO: 12) | -1.7 | -4.4 | 1.3 | 1.1 |
| BNIP3 | gccgCACGTGccac (SEQ ID NO: 13) | -9.4 | -6.0 | 1.3 | 1.0 |
| EGLN3 | gggcTACGTGcaga (SEQ ID NO: 14) | -5.3 | -33.6 | 1.0 | -1.1 |
| EGLN1 | ggtgTACGTGcaga (SEQ ID NO: 15) | -3.4 | -19.8 | 1.1 | 1.0 |
| PGK1 | gtgaGACGTGcggc (SEQ ID NO: 16) tgccGACGTGcgct (SEQ ID NO: 17) | -5.4 | -3.3 | -1.2 | 1.0 |
| CA9 | gctgTACGTGcatt (SEQ ID NO: 18) | -89.0 | -9.4 | -2.1 | -1.1 |
| VEGF | tgcaTACGTGggct (SEQ ID NO: 19) | -3.4 | -34.0 | -2.0 | -1.3 |
| FLT1 | gaacAACGTGgaat (SEQ ID NO: 20) | -2.2 | -4.7 | -2.0 | -1.1 |
| EDN1 | aggcAACGTGcagc (SEQ ID NO: 21) | -3.5 | -31.0 | -2.5 | 1.3 |

Quantitative real-time RT-PCR was used to confirm the effects of polyamides 11.1, 11.3, echinomycin, and siRNA treatments on these 11 genes. RT-PCR confirms that siRNA and echinomycin reduced expression of all genes in this set. Polyamide 11.1 significantly affected 4 genes in this set. Polyamide 11.3 had a modest but measurable effect on VEGF expression, but little effect on the expression of all the others. Chromatin immunoprecipitation was used to measure HIF-1 occupancy at the HREs of VEGF and carbonic anhydrase IX (CA9), which were both affected by polyamide 11.1, and PGK1, which was unaffected (FIG. 17). HIF-1α occupancy at the VEGF HRE was decreased by HIF-1α siRNA, echinomycin, and polyamide 11.1, but less so by treatment with HRE-mismatch polyamide 11.3. HIF-1 occupancy at the carbonic anhydrase IX locus was also decreased by HIF-1α siRNA, echinomycin, and polyamide 11.1, but was unaffected by 11.3. HIF-1 occupancy at PGK1 was markedly decreased by siRNA, but minimally affected by polyamide 11.1 or 11.3.

Surprisingly, echinomycin did not appear to affect HIF-1 occupancy at this locus. It is interesting to note that all of the genes affected by polyamide 11.1 displayed in Table 1 have HREs that fall within the sequence 5'-(T/A)ACGTG-3', consistent with the expected DNA binding preferences for this molecule.

2.3.4 Conclusions and Significance.

In this experiment, polyamide 11.1 (1 µM) affected expression of 2,284 transcripts by more than 2-fold ($p \leq 0.01$), which represents less than 5% of transcripts assayed. A search of the publicly available human genome for the sequence 5'-WTWCGW-3' finds 1,876,480 potential match sites for polyamide 11.1. This corresponds to an average of one binding site every 1,600 base pairs. The proportion of these sites accessible to polyamide binding in the context of heterochromatin in vivo is currently unknown. Additionally, data from in vitro transcription experiments suggest that polyamides noncovalently bound within the coding region of a gene would not interfere with RNA polymerase activity at that locus (34). It would thus not be surprising if a significant fraction of polyamide-DNA binding events in a cell do not directly affect gene expression. In parallel to this, global analysis of transcription factor binding to chromatin in vivo has shown occupancy at promoters and enhancers without associated changes in gene expression at that locus (46).

Interestingly, polyamide 11.1 (1 µM) affected the expression of fewer genes than HIF-1α siRNA under the conditions of the experiment. A direct comparison in genomic specificity between polyamide and siRNA cannot be drawn from these limited data because a large proportion of the genes affected by siRNA are likely a result of silencing the target gene, HIF-1α, rather than off-target effects involving post-transcriptional silencing of mRNA using the RNA interference pathway (47). If we eliminate from the total number of transcripts affected by the HIF-1α siRNA (2-fold, $p \leq 0.01$) all transcripts affected by treatment with DFO alone (1.5-fold, $p \leq 0.01$) we are left with 1,523 affected transcripts. A similar treatment of the data for polyamide 11.1 results in 1,626 affected transcripts. It should also be noted that for most HIF-1 regulated genes affected by both polyamide and siRNA, inhibition by the polyamide was more modest than siRNA, suggesting incomplete abrogation of HIF-1 DNA binding by the polyamide. Approximately 23% of the 297 transcripts induced by DFO were inhibited by polyamide 11.1. For genes where the functional HRE has been identified, the effects of treatment with polyamide 11.1 or echinomycin are, thus far, consistent with the expected binding preferences of these molecules.

HIF-1 is frequently overactive in tumors, and a number of direct targets in the HIF-1 pathway have become points of clinical intervention (48). Bevacizumab, an anti-VEGF antibody, and sorafenib and sunitinib, tyrosine kinase inhibitors with activity against the VEGF receptors, have shown some promise in clinical trials as cancer therapeutics (49-51). Echinomycin had been previously brought to the clinic as a cancer therapeutic in phase I and II trials (52), based on observations that echinomycin exhibits potent anti-proliferative effects on several tumor-derived cell lines (52, 53). However, survival benefit was not established (52). In light of recent work by Melillo and colleagues, re-examination of the clinical use of echinomycin in tumor types expected to be highly sensitive to HIF-1 activity may be justified (21).

The induction of pro-angiogenic, proliferative, metastatic, and glycolytic genes by HIF-1 are established as contributing to the cancer phenotype (11). Genes that promote cell death, such as BNIP3 and NIX (BNIP3L), are also induced by hypoxia through HIF-1 (54). In this sense, HIF-1 plays dual roles in the survival and death pathways of tumor cells (12). A functional separation of these targets of HIF-1 at the level of HIF-1-DNA binding might have clinical relevance (12). Given sufficient knowledge of the particular regulatory sequences involved, one could, in principle, design a polyamide or cocktail of polyamides to affect a selected subset of target genes in the HIF-1 pathway, making use of the programmability of polyamide recognition for targeting particular HREs and flanking sequences. The utility of polyamides as regulators of hypoxia-induced gene expression awaits continued study in small animal models of HIF-1 activity.

2.4 Methods 2.4.1 Synthesis of Polyamides

Polyamides were synthesized by solid-phase methods on Kaiser oxime resin (Nova Biochem), cleaved from resin with 3,3'-diamino-N-methyl-dipropylamine and purified by reverse-phase HPLC (55). Isophthalic acid was activated with PyBOP (Nova Biochem) and conjugated to the polyamides as previously described (20). Purity and identity of polyamides were assessed by HPLC, UV-visible spectroscopy, and MALDI-ToF MS.

2.4.2 Determination of DNA-Binding Affinities and Sequence Specificities

Quantitative DNase I footprint titration experiments were used to measure the binding affinities of polyamides 11.1, 11.2, 11.3, and echinomycin on 5' $^{32}$P-labeled fragments of pGL2-VEGF-Luc and pCSJ-FLT1 containing promoter sequences containing the HREs of VEGF and FLT1, respectively. Quantitative DNase I footprint titration experiments were conducted as reported previously (56).

2.4.2 Measurement of Hypoxia-Induced Gene Expression

U251 cells were plated in 24-well plates at a density of $20-30 \times 10^3$ cells per well ($40-60 \times 10^3$ cells/ml) in RPMI (ATCC) supplemented with 5% FBS (Irvine Scientific). After 24 hours, polyamides were added to the adhered cells in cell media solutions at the appropriate concentration and incubated with the cells for 48 hours. Hypoxic induction of gene expression was chemically induced by adding DFO to 300 pM for an additional 16 hours. When appropriate, echinomycin was added two hours prior to DFO stimulation. Isolation of RNA and subsequent cDNA synthesis were as previously described (19). When appropriate, HIF-1α siRNA (HIF-1α validated stealth duplex, Invitrogen) or mismatch control siRNA with similar GC content (Invitrogen) was transfected 48 hours prior to RNA isolation. Transfection of siRNA was achieved using Lipofectamine 2000 (Invitrogen) according to manufacturer's protocols. Quantitative real-time RT-PCR was performed using SYBR Green PCR Master Mix (Applied Biosystems) on an ABI 7300 instrument. Target gene mRNA was measured relative to β-glucuronidase as an endogenous control. Primer employed were: VEGF, L 5'AGGGCAGAATCATCACGAAG-3' (SEQ ID NO:22), R 5'-GGGTACTCC TGGAAGATGTCC-3' (SEQ ID NO:23); β-glucuronidase, L 5'-CTCATTTGGAATTTTGCCGATT-3' (SEQ ID NO:24), R 5'-CCGAGTGAAGATCCCCTTTTTA-3' (SEQ ID NO:25); FLT1, L 5'-CAGCAACATGGGAAA-CAGAAT-3' (SEQ ID NO:26), R 5'-TAGAGTCAGCCA-CAACCAAGG-3' (SEQ ID NO:27).

2.4.3 Chromatin Immunoprecipitation

U251 cells were plated in 15 cm diameter plates and left to attach overnight. Media, time course, DFO, polyamide, echinomycin, and siRNA treatments were as described above. After the 16 hour DFO treatment, cells were treated with 1% formaldehyde for 10 minutes. Chromatin was isolated and sheared. HIF-1α antibodies (Novus Biologicals) were used to immunoprecipitate HIF-1-bound DNA fragments. After crosslink reversal, PCRs using primers targeted to the regions of interest were used to assess enrichment of bound fragments as compared to mock-precipitated (no antibody) controls. PCRs were monitored either using SYBR Green PCR Master Mix (Applied Biosystems) on an ABI 7300 instrument, or directly visualized using gel electrophoresis. The following primers were used: VEGF, L 5'-CCTTTGGGTTTTGC-CAGA-3' (SEQ ID NO:28), R 5'-CCAAGTTTGTG-GAGCTGA-3' (SEQ ID NO:29); CA9, L 5'-AAAAGGGCGCTCTGTGAGT-3' (SEQ ID NO:30), R 5'-GCTGACTGTGGGGTGTCC-3' (SEQ ID NO:31); PGK1, L 5'-CCCCTAAGTCGGGAAGGTT-3' (SEQ ID NO:32), R 5'-GTCCGTCTGCGAGGGTACTA-3' (SEQ ID NO:33).

2.4.4 Analysis of Gene Expression with Oligonucleotide Microarrays

U251 cells were plated in 12-well plates at a density of $40-60 \times 10^3$ cells per well. Media, time course, DFO, polyamide, echinomycin, and siRNA treatments were as described above. RNA was isolated as previously described. Further sample preparation for microarray experiments was carried out at the Millard and Muriel Jacobs Gene Expression Facility at Caltech. Labeled mRNA was hybridized to Affymetrix Human 133 arrays according to established protocols. Gene expression was analyzed using Resolver (Rosetta Biosoftware, Seattle).

2.4.5 Accession Codes

Data have been deposited in NCBIs Gene Expression Omnibus (GEO, http://www.ncbi.nlm.gov/geo/), accessible through GEO Series accession number GSE7535.

2.5 References

1. Blancafort, P., Segal, D. J., and Barbas, C. F. (2004) Designing transcription factor architectures for drug discovery, *Mol. Pharmacol.* 66, 1361-1371.
2. Beerli, R. R., and Barbas, C. F. (2002) Engineering polydactyl zinc-finger transcription factors, *Nat. Biotechnol.* 20, 135-141.
3. Beerli, R. R., Segal, D. J., Dreier, B., and Barbas, C. F. (1998) Toward controlling gene expression at will: Specific regulation of the erbB-2/HER-2 promoter by using polydactyl zinc finger proteins constructed from modular building blocks, *Proc. Natl. Acad. Sci. U S. A.* 95, 14628-14633.
4. Liu, P. Q., Rebar, E. J., Zhang, L., Liu, Q., Jamieson, A. C., Liang, Y. X., Qi, H., Li, P. X., Chen, B. L., et al. (2001) Regulation of an endogenous locus using a panel of designed zinc finger proteins targeted to accessible chromatin regions—Activation of vascular endothelial growth factor A, *J. Biol. Chem.* 276, 11323-11334.
5. Fire, A., Xu, S. Q., Montgomery, M. K., Kostas, S. A., Driver, S. E., and Mello, C. C. (1998) Potent and specific genetic interference by double-stranded RNA in *Caenorhabditis elegans*, *Nature* 391, 806-811.
6. Meister, G., and Tuschl, T. (2004) Mechanisms of gene silencing by double-stranded RNA, *Nature* 431, 343-349.
7. Mello, C. C., and Conte, D. (2004) Revealing the world of RNA interference, *Nature* 431, 338-342.
8. Hannon, G. J., and Rossi, J. J. (2004) Unlocking the potential of the human genome with RNA interference, *Nature* 431, 371-378.
9. Dervan, P. B., and Edelson, B. S. (2003) Recognition of the DNA minor groove by pyrrole-imidazole polyamides, *Curr. Opin. Struct. Biol.* 13, 284-299.
10. Nickols, N. G., and Dervan, P. B. (2007) Suppression of androgen receptor-mediated gene expression by a sequence-specific DNA-binding polyamide, *Proc. Natl. Acad. Sci. U.S.A.* 104, 10418-10423.
11. Semenza, G. L. (2003) Targeting HIF-1 for cancer therapy, *Nat. Rev. Cancer* 3, 721-732.
12. Zhou, J., Schmid, T., Schnitzer, S., and Brune, B. (2006) Tumor hypoxia and cancer progression, *Cancer Lett.* 237, 10-21.
13. Pouyssegur, J., Dayan, F., and Mazure, N. M. (2006) Hypoxia signalling in cancer and approaches to enforce tumour regression, *Nature* 441, 437-443.
14. Melillo, G. (2006) Inhibiting hypoxia-inducible factor 1 for cancer therapy, *Molecular Cancer Research* 4, 601-605.
15. Semenza, G. L. (2000) HIF-1 and human disease: one highly involved factor, *Genes Dev.* 14, 1983-1991.
16. Ivan, M., Kondo, K., Yang, H. F., Kim, W., Valiando, J., Ohh, M., Salic, A., Asara, J. M., Lane, W. S., et al. (2001) HIF alpha targeted for VHL-mediated destruction by proline hydroxylation: Implications for O-2 sensing, *Science* 292, 464-468.
17. Zimmer, M., Doucette, D., Siddiqui, N., and Iliopoulos, O. (2004) Inhibition of hypoxia-inducible factor is sufficient for growth suppression of VHL-/- tumors, *Molecular Cancer Research* 2, 89-95.
18. Kung, A. L., Zabludoff, S. D., France, D. S., Freedman, S. J., Tanner, E. A., Vieira, A., Cornell-Kennon, S., Lee, J., Wang, B. Q., et al. (2004) Small molecule blockade of transcriptional coactivation of the hypoxia-inducible factor pathway, *Cancer Cell* 6, 33-43.
19. Olenyuk, B. Z., Zhang, G. J., Klco, J. M., Nickols, N. G., Kaelin, W. G., and Dervan, P. B. (2004) Inhibition of vascular endothelial growth factor with a sequence-specific hypoxia response element antagonist, *Proc. Natl. Acad. Sci. U.S.A.* 101, 16768-16773.
20. Nickols, N. G., Jacobs, C. S., Farkas, M. E., and Dervan, P. B. (2007) Improved nuclear localization of DNA-binding polyamides, *Nucleic Acids Res.* 35, 363-370.
21. Kong, D. H., Park, E. J., Stephen, A. G., Calvani, M., Cardellina, J. H., Monks, A., Fisher, R. J., Shoemaker, R. H., and Melillo, G. (2005) Echinomycin, a small-molecule inhibitor of hypoxia-inducible factor-1 DNA-binding activity, *Cancer Res.* 65, 9047-9055.
22. Van Dyke, M. M., and Dervan, P. B. (1984) Echinomycin Binding-Sites on DNA, *Science* 225, 1122-1127.
23. Kielkopf, C. L., Baird, E. E., Dervan, P. D., and Rees, D. C. (1998) Structural basis for G•C recognition in the DNA minor groove, *Nat. Struct. Biol.* 5, 104-109.
24. White, S., Szewczyk, J. W., Turner, J. M., Baird, E. E., and Dervan, P. B. (1998) Recognition of the four Watson-Crick base pairs in the DNA minor groove by synthetic ligands, *Nature* 391, 468-471.
25. Foister, S., Marques, M. A., Doss, R. M., and Dervan, P. B. (2003) Shape selective recognition of T•A base pairs by hairpin polyamides containing N-terminal 3-methoxy (and 3-chloro) thiophene residues, *Bioorg Med. Chem.* 11, 4333-4340.
26. Liu, Y. X., Cox, S. R., Morita, T., and Kourembanas, S. (1995) Hypoxia Regulates Vascular Endothelial Growth-Factor Gene-Expression in Endothelial-Cells—Identification of a 5'-Enhancer, *Circ. Res.* 77, 638-643.
27. Forsythe, J. A., Jiang, B. H., Iyer, N. V., Agani, F., Leung, S. W., Koos, R. D., and Semenza, G. L. (1996) Activation of vascular endothelial growth factor gene transcription by hypoxia-inducible factor 1, *Mol. Cell. Biol.* 16, 4604-4613.
28. Gerber, H. P., Condorelli, F., Park, J., and Ferrara, N. (1997) Differential transcriptional regulation of the two vascular endothelial growth factor receptor genes—Flt-1, but not Flk-1/KDR, is up-regulated by hypoxia, *J. Biol. Chem.* 272, 23659-23667.

29. Waring, M. J., and Wakelin, L. P. G. (1974) Echinomycin—Bifunctional Intercalating Antibiotic, *Nature* 252, 653-657.
30. Low, C. M. L., Drew, H. R., and Waring, M. J. (1984) Sequence-Specific Binding of Echinomycin to DNA—Evidence for Conformational-Changes Affecting Flanking Sequences, *Nucleic Acids Res.* 12, 4865-4879.
31. Fechter, E. J., and Dervan, P. B. (2003) Allosteric inhibition of protein-DNA complexes by polyamide-intercalator conjugates, *J. Am. Chem. Soc.* 125, 8476-8485.
32. Fechter, E. J., Olenyuk, B., and Dervan, P. B. (2004) Design of a sequence-specific DNA bisintercalator, *Angew. Chem.-Int. Edit.* 43, 3591-3594.
33. Kageyama, Y., Sugiyama, H., Ayame, H., Iwai, A., Fujii, Y., Huang, L. E., Kizaka-Kondoh, S., Hiraoka, M., and Kihara, K. (2006) Suppression of VEGF transcription in renal cell carcinoma cells by pyrrole-imidazole hairpin polyamides targeting the hypoxia responsive element, *Acta Oncol.* 45, 317-324.
34. Dickinson, L. A., Gulizia, R. J., Trauger, J. W., Baird, E. E., Mosier, D. E., Gottesfeld, J. M., and Dervan, P. B. (1998) Inhibition of RNA polymerase II transcription in human cells by synthetic DNA-binding ligands, *Proc. Natl. Acad. Sci. U.S.A.* 95, 12890-12895.
35. Oakley, M. G., Mrksich, M., and Dervan, P. B. (1992) Evidence That a Minor Groove-Binding Peptide and a Major Groove-Binding Protein Can Simultaneously Occupy a Common Site on DNA, *Biochemistry* 31, 10969-10975.
36. Tacchini, L., Bianchi, L., Bernelli-Zazzera, A., and Cairo, G. (1999) Transferrin receptor induction by hypoxia—HIF-1-mediated transcriptional activation and cell-specific post-transcriptional regulation, *J. Biol. Chem.* 274, 24142-24146.
37. Lok, C. N., and Ponka, P. (1999) Identification of a functional hypoxia-response element in the transferrin-receptor gene, *Exp. Hematol.* 27, 91-91.
38. Fukasawa, M., Tsuchiya, T., Takayama, E., Shinomiya, N., Uyeda, K., Sakakibara, R., and Seki, S. (2004) Identification and characterization of the hypoxia-responsive element of the human placental 6-phosphofructo-2-kinase/fructose-2,6-bisphosphatase gene, *J. Biochem.* 136, 273-277.
39. Obach, M., Navarro-Sabate, A., Caro, J., Kong, X. G., Duran, J., Gomez, M., Perales, J. C., Ventura, F., Rosa, J. L., et al. (2004) 6-phosphofructo-2-kinase (pfkfb3) gene promoter contains hypoxia-inducible factor-1 binding sites necessary for transactivation in response to hypoxia, *J. Biol. Chem.* 279, 53562-53570.
40. Semenza, G. L., Jiang, B. H., Leung, S. W., Passantino, R., Concordet, J. P., Maire, P., and Giallongo, A. (1996) Hypoxia response elements in the aldolase A, enolase 1, and lactate dehydrogenase A gene promoters contain essential binding sites for hypoxia-inducible factor 1, *J. Biol. Chem.* 271, 32529-32537.
41. Semenza, G. L., Roth, P. H., Fang, H. M., and Wang, G. L. (1994) Transcriptional Regulation of Genes Encoding Glycolytic-Enzymes by Hypoxia-Inducible Factor-1, *J. Biol. Chem.* 269, 23757-23763.
42. Pescador, N., Cuevas, Y., Naranjo, S., Alcaide, M., Villar, D., Landazuri, M., and Del Peso, L. (2005) Identification of a functional hypoxia-responsive element that regulates the expression of the egl nine homologue 3 (egln3/phd3) gene, *Biochem. J.* 390, 189-197.
43. Willam, C., Nicholls, L. G., Ratcliffe, P. J., Pugh, C. W., and Maxwell, P. H. (2004) The prolyl hydroxylase enzymes that act as oxygen sensors regulating destruction of hypoxia inducible factor alpha, *Advances in Enzyme Regulation*, 44, 75-92.
44. Grabmaier, K., de Weijert, M. C. A., Verhaegh, G. W., Schalken, J. A., and Oosterwijk, E. (2004) Strict regulation of CAIX(G250/MN) by HIF-1 alpha in clear cell renal cell carcinoma, *Oncogene* 23, 5624-5631.
45. Hu, J., Discher, D. J., Bishopric, N. H., and Webster, K. A. (1998) Hypoxia regulates expression of the endothelin-1 gene through a proximal hypoxia-inducible factor-1 binding site on the antisense strand, *Biochem. Biophys. Res. Commun.* 245, 894-899.
46. Zhang, X. M., Odom, D. T., Koo, S. H., Conkright, M. D., Canettieri, G., Best, J., Chen, H. M., Jenner, R., Herbolsheimer, E., et al. (2005) Genome-wide analysis of cAMP-response element binding protein occupancy, phosphorylation, and target gene activation in human tissues, *Proc. Natl. Acad. Sci. U.S.A.* 102, 4459-4464.
47. Jackson, A. L., Bartz, S. R., Schelter, J., Kobayashi, S. V., Burchard, J., Mao, M., Li, B., Cavet, G., and Linsley, P. S. (2003) Expression profiling reveals off-target gene regulation by RNAi, *Nat. Biotechnol.* 21, 635-637.
48. Cohen, H. T., and McGovern, F. J. (2005) Renal-cell carcinoma, *N. Engl. J. Med.* 353, 2477-2490.
49. Escudier, B., Eisen, T., Stadler, W. M., Szczylik, C., Oudard, S., Siebels, M., Negrier, S., Chevreau, C., Solska, E., et al. (2007) Sorafenib in advanced clear-cell renal-cell carcinoma, *N. Engl. J. Med.* 356, 125-134.
50. Motzer, R. J., Hutson, T. E., Tomczak, P., Michaelson, M. D., Bukowski, R. M., Rixe, O., Oudard, S., Negrier, S., Szczylik, C., et al. (2007) Sunitinib versus interferon alfa in metastatic renal-cell carcinoma, *N. Engl. J. Med.* 356, 115-124.
51. Yang, J. C., Haworth, L., Sherry, R. M., Hwu, P., Schwartzentruber, D. J., Topalian, S. L., Steinberg, S. M., Chen, H. X., and Rosenberg, S. A. (2003) A randomized trial of bevacizumab, an anti-vascular endothelial growth factor antibody, for metastatic renal cancer, *N. Engl. J. Med.* 349, 427-434.
52. Foster, B. J., Clagettcarr, K., Shoemaker, D. D., Suffness, M., Plowman, J., Trissel, L. A., Grieshaber, C. K., and Leylandjones, B. (1985) Echinomycin—the 1st Bifunctional Intercalating Agent in Clinical-Trials, *Invest. New Drugs* 3, 403-410.
53. May, L. G., Madine, M. A., and Waring, M. J. (2004) Echinomycin inhibits chromosomal DNA replication and embryonic development in vertebrates, *Nucleic Acids Res.* 32, 65-72.
54. Kothari, S., Cizeau, J., McMillan-Ward, E., Israels, S. J., Bailes, M., Ens, K., Kirshenbaum, L. A., and Gibson, S. B. (2003) BNIP3 plays a role in hypoxic cell death in human epithelial cells that is inhibited by growth factors EGF and IGF, *Oncogene* 22, 4734-4744.
55. Belitsky, J. M., Nguyen, D. H., Wurtz, N. R., and Dervan, P. B. (2002) Solid-phase synthesis of DNA binding polyamides on oxime resin, *Bioorg. Med. Chem.* 10, 2767-2774.
56. Trauger, J. W., and Dervan, P. B. (2001) Footprinting methods for analysis of pyrrole-imidazole polyamide/DNA complexes, *Methods Enzymol.* 340, 450-466.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims. All publications, including patent documents and scientific articles, referred to in this application and the bibliography and attachments are incorporated by reference in their entirety for all purposes to the same extent as if each individual publication were individually incorporated by reference. The article "a" as used herein means one or more unless indicated otherwise. All headings are for the convenience of the reader and should not be used to limit the meaning of the text that follows the heading, unless so specified.

What is claimed is:

1. A polyamide-tail conjugate comprising a tail linked to a polyamide, wherein said polyamide is capable of binding DNA with an affinity of less than 100 nM, and wherein said tail comprises a linker and an end-group, and
   (a) wherein said linker is a $C_{2-12}$ alkyl or has a structure of $(R_1(CR_2R_3)hR_4)i$;
      where $R_1$ and $R_4$ are independently selected from NH and O;
      where $R_2$ and $R_3$ are independently selected from H, OH, F, Cl, Br, I, $NO_2$, $NH_2$, $CF_jH_k$, $OCF_jH_k$, COOH, $CONH_2$, CONR'R''; where R' and R'' are independently selected from H, methyl, ethyl, $CF_jH_k$, $C_2F_nH_m$, F, Cl, Br, I, CN, $CF_3$, $CCl_3$, $CBr_3$, $Cl_3$, $NO_2$, $COOCF_jH_k$, $(OPO_3)^{2-}$, $OCOCH_3$, $OCOCF_jH_k$, OMe, OEt, $OCF_jH_k$, $NH_2$, $NR_6R_7$; where $R_6$ and $R_7$ may be H or $C_{1-3}$ alkyl; and where j+k=3, n+m=5, and n or m may be 0; and
      where h and i are independently selected from any integer from 1 to 4;
   (b) wherein said end-group is selected from the group consisting of isophthalic acid; phthalic acid; terephthalic acid; morpholine; N,N-dimethylbenzamide; N,N-bis(trifluoromethyl)benzamide; fluorobenzene; (trifluoromethyl)benzene; nitrobenzene; phenyl acetate; phenyl 2,2,2-trifluoroacetate; phenyl dihydrogen phosphate; 2H-pyran; 2H-thiopyran; benzoic acid; isonicotinic acid; and nicotinic acid; where one, two or three ring members in any of these end-group candidates may be independently substituted with C, N, S or O; and
      where any one, two, three, four or five of the hydrogens bound to the ring may be substituted with $R_5$, wherein $R_5$ may be independently selected for any substitution from H, OH, F, Cl, Br, I, $NO_2$, $NH_2$, $CF_jH_k$, $OCF_jH_k$, COOH, $CONH_2$; CONR'R''; where R' and R'' need not be the same group and can be H, methyl, ethyl, $CF_jH_k$, $C_2F_nH_m$, F, Cl, Br, I, CN, $CF_3$, $CCl_3$, $CBr_3$, $Cl_3$, $NO_2$, $COOCF_jH_k$, $(OPO_3)^{2-}$, $OCOCH_3$, $OCOCF_jH_k$, OMe, OEt, $OCF_jH_k$, $NH_2$, $NR_6R_7$; where $R_6$ and $R_7$ may be H or $C_{1-3}$ alkyl; and where j+k=3, n+m=5, and n or m may be 0.

2. The polyamide-tail conjugate of claim 1, wherein said polyamide has a formula of $X_1X_2 \ldots X_m\text{-L-}X_{(m+1)} \ldots X_{(2m-1)}X_{2m}$, where X is a linkable unit, L is a linking element, and m is an integer from 1 to 10.

3. The polyamide-tail conjugate of claim 1, wherein said conjugate has at least 20-fold greater affinity for a target site than for a site differing from said target site by base pairs.

4. The polyamide-tail conjugate of claim 1, wherein said conjugate has about 100-fold greater affinity for a target site than for a site differing from said target site by two base pairs.

5. The polyamide-tail conjugate of claim 1, wherein said conjugate further comprises a pharmaceutically acceptable carrier.

6. The polyamide-tail conjugate of claim 1, wherein said polyamide is selected from the group consisting of a hairpin polyamide, a H-pin polyamide, an overlapped polyamide, a slipped polyamide, a cyclic polyamide, a tandem polyamide, and an extended polyamide.

7. The polyamide-tail conjugate of claim 1, wherein said polyamide is selected from the group consisting of a hairpin polyamide, a H-pin polyamide, an overlapped polyamide, a slipped polyamide, a cyclic polyamide, a tandem polyamide, and an extended polyamide.

8. A polyamide-tail conjugate comprising a tail linked to a polyamide, wherein said polyamide is capable of binding DNA with an affinity of less than 100 nM, and wherein said tail comprises a linker and an end-group, and
   (a) wherein said linker is a $C_{2-12}$ alkyl;
   (b) wherein said end-group is a benzyl, wherein one, two or three carbons may be substituted by N, S or O; and wherein a hydrogen may be substituted with OH, F, Cl, Br, I, $NO_2$, $NH_2$, $CF_jH_k$, $OCF_jH_k$, COOH, $CONH_2$; CONR'R''; where R' and R'' need not be the same group and can be H, methyl, ethyl, $CF_jH_k$, $C_2F_nH_m$, F, Cl, Br, I, CN, $CF_3$, $CCl_3$, $CBr_3$, $Cl_3$, $NO_2$, $COOCF_jH_k$, $(OPO_3)^{2-}$, $OCOCH_3$, $OCOCF_jH_k$, OMe, OEt, $OCF_jH_k$, $NH_2$, $NR_6R_7$; where $R_6$ and $R_7$ may be H or $C_{1-3}$ alkyl; and where j+k=3, n+m=5, and n or m may be 0.

9. The polyamide-tail conjugate of claim 8, wherein said end-group is selected from the group consisting of isophthalic acid; phthalic acid; terephthalic acid; benzamide; morpholine; N,N-dimethylbenzamide; N,N-bis(trifluoromethyl) benzamide; fluorobenzene; (trifluoromethyl)benzene; nitrobenzene; methyl benzoate; phenyl acetate; phenyl 2,2,2-trifluoroacetate; phenyl dihydrogen phosphate; 2H-pyran; 2H-thiopyran; benzoic acid; isonicotinic acid; and nicotinic acid.

10. The polyamide-tail conjugate of claim 8, wherein said polyamide has a formula of $X_1X_2 \ldots X_m\text{-L-}X_{(m+1)} \ldots$ $X_{(2m-1)}X_{2m}$, where X is a linkable unit, L is a linking element, and m is an integer from 1 to 10.

11. The polyamide-tail conjugate of claim 8, wherein said conjugate has at least 20-fold greater affinity for a target site than for a site differing from said target site by base pairs.

12. The polyamide-tail conjugate of claim 8, wherein said conjugate has about 100-fold greater affinity for a target site than for a site differing from said target site by two base pairs.

13. The polyamide-tail conjugate of claim 8, wherein said conjugate further comprises a pharmaceutically acceptable carrier.

14. The polyamide-tail conjugate of claim 8, wherein said polyamide is selected from the group consisting of a hairpin polyamide, a H-pin polyamide, an overlapped polyamide, a slipped polyamide, a cyclic polyamide, a tandem polyamide, and an extended polyamide.

15. A polyamide-tail conjugate comprising a tail linked to a polyamide, wherein said polyamide is capable of binding DNA with an affinity of less than 100 nM, and wherein said tail comprises a linker and an end-group, and
   (a) wherein said linker is selected from the group consisting of compound L1, L2, L3, L4, L5, L6, L7 and L8; and wherein each n may be independently selected from 0-8;
   (b) wherein said end-group is a benzyl, wherein one, two or three carbons may be substituted by N, S or O; and wherein a hydrogen may be substituted with OH, F, Cl, Br, I, $NO_2$, $NH_2$, $CF_jH_k$, $OCF_jH_k$, COOH, $CONH_2$; CONR'R"; where R' and R" need not be the same group and can be H, methyl, ethyl, $CF_jH_k$, $C_2F_nH_m$, F, Cl, Br, I, CN, $CF_3$, $CCl_3$, $CBr_3$, $Cl_3$, $NO_2$, $COOCF_jH_k$, $(OPO_3)^{2-}$, $OCOCH_3$, $OCOCF_jH_k$, OMe, OEt, $OCF_jH_k$, $NH_2$, $NR_6R_7$; where $R_6$ and $R_7$ may be H or $C_{1-3}$ alkyl; and where j+k=3, n+m=5, and n or m may be 0.

16. The polyamide-tail conjugate of claim 15, wherein said end-group is selected from the group consisting of isophthalic acid; phthalic acid; terephthalic acid; benzamide; morpholine; N,N-dimethylbenzamide; N,N-bis(trifluoromethyl)benzamide; fluorobenzene; (trifluoromethyl)benzene; nitrobenzene; methyl benzoate; phenyl acetate; phenyl 2,2,2-trifluoroacetate; phenyl dihydrogen phosphate; 2H-pyran; 2H-thiopyran; benzoic acid; isonicotinic acid; and nicotinic acid.

17. The polyamide-tail conjugate of claim 15, wherein said polyamide has a formula of $X_1X_2 \ldots X_m\text{-L-}X_{(m+1)} \ldots X_{(2m-1)}X_{2m}$, where X is a linkable unit, L is a linking element, and m is an integer from 1 to 10.

18. The polyamide-tail conjugate of claim 15, wherein said conjugate has at least 20-fold greater affinity for a target site than for a site differing from said target site by base pairs.

19. The polyamide-tail conjugate of claim 15, wherein said conjugate has about 100-fold greater affinity for a target site than for a site differing from said target site by two base pairs.

20. The polyamide-tail conjugate of claim 15, wherein said conjugate further comprises a pharmaceutically acceptable carrier.

* * * * *